United States Patent
Narra et al.

(10) Patent No.: US 12,001,648 B2
(45) Date of Patent: *Jun. 4, 2024

(54) USER INTERFACES FOR LOGGING USER ACTIVITIES

(71) Applicant: Apple Inc., Cupertino, CA (US)

(72) Inventors: Aneesha Narra, Belmont, CA (US);
Justin P. Dobson, Sunnyvale, CA (US);
Ottavia Golfetto, Cupertino, CA (US);
Shonn P. Hendee, Los Gatos, CA (US);
Rajiv B. Kumar, San Jose, CA (US);
Tal Lorberbaum, Mountain View, CA (US); Ron D. Lue-Sang, Fremont, CA (US); Divya Nag, San Jose, CA (US);
Andrew Plummer, Palo Alto, CA (US);
Heather R. Schneck, Cupertino, CA (US); Ryan D. Shelby, Mountain View, CA (US); Jonathan C. Stemmle, San Mateo, CA (US); Connie V. Tung, Berkeley, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/952,053

(22) Filed: Sep. 23, 2022

(65) Prior Publication Data

US 2023/0020517 A1    Jan. 19, 2023

Related U.S. Application Data

(63) Continuation of application No. 16/953,781, filed on Nov. 20, 2020, now Pat. No. 11,698,710.

(Continued)

(51) Int. Cl.
*G06F 3/04817*  (2022.01)
*G06F 3/0482*   (2013.01)
*G06F 11/34*    (2006.01)

(52) U.S. Cl.
CPC ........ *G06F 3/04817* (2013.01); *G06F 3/0482* (2013.01); *G06F 11/3438* (2013.01); *G06F 11/3476* (2013.01)

(58) Field of Classification Search
CPC .......................... G06F 3/04817; G06F 3/0482
See application file for complete search history.

(56) References Cited

U.S. PATENT DOCUMENTS 5,515,344 A    5/1996  Ng
5,642,731 A    7/1997  Kehr
(Continued)

FOREIGN PATENT DOCUMENTS

CA    2815518 A1    5/2012
CN    1752973 A     3/2006
(Continued)

OTHER PUBLICATIONS

Applicant-Initiated Interview Summary received for U.S. Appl. No. 16/851,451, dated Nov. 29, 2022, 4 pages.
(Continued)

*Primary Examiner* — Mong-Shune Chung
(74) *Attorney, Agent, or Firm* — DLA Piper LLP (US)

(57) ABSTRACT

The present disclosure generally relates to logging user activities during a subset of a recurring time period. In some embodiments, based on received physiological data, a computer system enables logging of one or more user activities to be performed during a subset of a recurring time period. In some embodiments, based on performance of the one or more user activities during a subset of a recurring time period, a computer system enables logging of one or more user activities to be performed during a subset of a recurring time period for a predetermined period of time.

33 Claims, 30 Drawing Sheets

Related U.S. Application Data

(60) Provisional application No. 63/072,889, filed on Aug. 31, 2020.

(56) References Cited

U.S. PATENT DOCUMENTS

| | | | |
|---|---|---|---|
| 6,416,471 B1 | 7/2002 | Kumar et al. | |
| 6,600,696 B1 | 7/2003 | Lynn | |
| 6,705,972 B1 | 3/2004 | Takano et al. | |
| 6,950,839 B1 | 9/2005 | Green et al. | |
| 7,128,693 B2 | 10/2006 | Brown et al. | |
| 7,166,078 B2 | 1/2007 | Saini et al. | |
| 7,739,148 B2 | 6/2010 | Suzuki et al. | |
| 8,321,006 B1 | 11/2012 | Snyder et al. | |
| 8,475,339 B2 | 7/2013 | Hwang et al. | |
| 8,676,170 B2 | 3/2014 | Porrati et al. | |
| 8,725,527 B1 | 5/2014 | Kahn et al. | |
| 8,758,262 B2 | 6/2014 | Rhee et al. | |
| 8,784,115 B1 | 7/2014 | Chuang | |
| 8,888,707 B2 | 11/2014 | Shirasaki et al. | |
| 9,026,927 B2 | 5/2015 | Brumback et al. | |
| 9,224,291 B2 * | 12/2015 | Moll-Carrillo | G06F 3/04842 |
| 9,579,060 B1 | 2/2017 | Lisy et al. | |
| 9,589,445 B2 * | 3/2017 | White | G16H 40/63 |
| 9,672,715 B2 | 6/2017 | Roberts et al. | |
| 9,712,629 B2 | 7/2017 | Molettiere et al. | |
| 9,721,066 B1 * | 8/2017 | Funaro | G16H 40/63 |
| 9,730,621 B2 | 8/2017 | Cohen et al. | |
| 9,801,562 B1 | 10/2017 | Host-Madsen | |
| 9,808,206 B1 | 11/2017 | Zhao et al. | |
| 9,813,642 B1 | 11/2017 | Chen et al. | |
| 9,940,682 B2 | 4/2018 | Hoffman et al. | |
| 10,004,451 B1 | 6/2018 | Proud | |
| 10,150,002 B2 | 12/2018 | Kass et al. | |
| 10,175,781 B2 | 1/2019 | Karagozler et al. | |
| 10,226,195 B2 | 3/2019 | Briante et al. | |
| 10,254,911 B2 | 4/2019 | Yang | |
| 10,275,262 B1 | 4/2019 | Bull et al. | |
| 10,339,830 B2 | 7/2019 | Han et al. | |
| 10,365,811 B2 | 7/2019 | Robinson et al. | |
| 10,576,327 B2 * | 3/2020 | Kim | G16H 40/63 |
| 10,592,088 B2 | 3/2020 | Robinson et al. | |
| 10,602,964 B2 | 3/2020 | Kerber | |
| 10,635,267 B2 | 4/2020 | Williams | |
| 10,674,942 B2 | 6/2020 | Williams et al. | |
| 10,762,990 B1 | 9/2020 | Schilling et al. | |
| 10,764,700 B1 | 9/2020 | Felton | |
| 10,796,549 B2 | 10/2020 | Roberts et al. | |
| 11,107,580 B1 | 8/2021 | Felton et al. | |
| 2001/0039503 A1 | 11/2001 | Chan et al. | |
| 2002/0095292 A1 | 7/2002 | Mittal et al. | |
| 2003/0126114 A1 | 7/2003 | Tedesco | |
| 2003/0130867 A1 | 7/2003 | Coelho et al. | |
| 2003/0181291 A1 | 9/2003 | Ogawa | |
| 2003/0191609 A1 | 10/2003 | Bernardi et al. | |
| 2003/0200483 A1 | 10/2003 | Sutton | |
| 2003/0216971 A1 | 11/2003 | Sick et al. | |
| 2003/0226695 A1 | 12/2003 | Mault | |
| 2004/0017300 A1 | 1/2004 | Kotzin et al. | |
| 2004/0034288 A1 | 2/2004 | Hennessy et al. | |
| 2004/0077958 A1 | 4/2004 | Kato et al. | |
| 2004/0190729 A1 | 9/2004 | Yonovitz et al. | |
| 2004/0193069 A1 | 9/2004 | Takehara | |
| 2004/0236189 A1 | 11/2004 | Hawthorne et al. | |
| 2005/0010117 A1 | 1/2005 | Agutter et al. | |
| 2005/0027208 A1 | 2/2005 | Shiraishi et al. | |
| 2005/0075214 A1 | 4/2005 | Brown et al. | |
| 2005/0079905 A1 * | 4/2005 | Martens | A63B 71/0686 463/1 |
| 2005/0149362 A1 | 7/2005 | Peterson et al. | |
| 2005/0187794 A1 | 8/2005 | Kimak | |
| 2005/0228735 A1 | 10/2005 | Duquette | |
| 2005/0244013 A1 | 11/2005 | Battenberg et al. | |
| 2005/0272564 A1 | 12/2005 | Pyles et al. | |
| 2006/0074863 A1 | 4/2006 | Kishore et al. | |
| 2006/0094969 A1 | 5/2006 | Nissila | |
| 2006/0098109 A1 | 5/2006 | Ooki | |
| 2006/0106741 A1 | 5/2006 | Janarthanan | |
| 2006/0136173 A1 | 6/2006 | Case, Jr. et al. | |
| 2006/0149144 A1 | 7/2006 | Lynn et al. | |
| 2006/0152372 A1 | 7/2006 | Stout | |
| 2006/0182287 A1 | 8/2006 | Schulein et al. | |
| 2006/0205564 A1 | 9/2006 | Peterson | |
| 2006/0235319 A1 | 10/2006 | Belohlavek et al. | |
| 2006/0274908 A1 | 12/2006 | Choi | |
| 2007/0016440 A1 | 1/2007 | Stroup | |
| 2007/0033066 A1 | 2/2007 | Ammer et al. | |
| 2007/0056727 A1 | 3/2007 | Newman | |
| 2007/0179434 A1 | 8/2007 | Weinert et al. | |
| 2007/0250505 A1 | 10/2007 | Yang et al. | |
| 2007/0250613 A1 | 10/2007 | Gulledge | |
| 2008/0005106 A1 | 1/2008 | Schumacher et al. | |
| 2008/0012701 A1 | 1/2008 | Kass et al. | |
| 2008/0021884 A1 | 1/2008 | Jones et al. | |
| 2008/0058626 A1 | 3/2008 | Miyata et al. | |
| 2008/0133742 A1 | 6/2008 | Southiere et al. | |
| 2008/0146892 A1 | 6/2008 | Leboeuf et al. | |
| 2008/0159547 A1 | 7/2008 | Schuler et al. | |
| 2008/0200312 A1 | 8/2008 | Tagliabue | |
| 2008/0205660 A1 | 8/2008 | Goldstein | |
| 2008/0228045 A1 | 9/2008 | Gao et al. | |
| 2008/0240519 A1 | 10/2008 | Nagamitsu | |
| 2008/0243885 A1 | 10/2008 | Harger et al. | |
| 2008/0300110 A1 | 12/2008 | Smith et al. | |
| 2009/0007596 A1 | 1/2009 | Goldstein et al. | |
| 2009/0052677 A1 | 2/2009 | Smith | |
| 2009/0065578 A1 | 3/2009 | Peterson et al. | |
| 2009/0105552 A1 | 4/2009 | Nishiyama et al. | |
| 2009/0118100 A1 | 5/2009 | Oliver et al. | |
| 2009/0172773 A1 | 7/2009 | Moore | |
| 2009/0180631 A1 | 7/2009 | Michael et al. | |
| 2009/0210078 A1 | 8/2009 | Crowley | |
| 2009/0216556 A1 | 8/2009 | Martin et al. | |
| 2009/0240521 A1 | 9/2009 | Simons et al. | |
| 2009/0245537 A1 | 10/2009 | Morin | |
| 2009/0259134 A1 | 10/2009 | Levine | |
| 2009/0262088 A1 | 10/2009 | Moll-Carrillo et al. | |
| 2009/0267776 A1 | 10/2009 | Glenn et al. | |
| 2009/0287103 A1 | 11/2009 | Pillai | |
| 2009/0287327 A1 | 11/2009 | Hsu et al. | |
| 2009/0290721 A1 | 11/2009 | Goldstein et al. | |
| 2009/0307105 A1 | 12/2009 | Lemay et al. | |
| 2010/0003951 A1 | 1/2010 | Ray et al. | |
| 2010/0010832 A1 | 1/2010 | Boute et al. | |
| 2010/0017489 A1 | 1/2010 | Birnbaum et al. | |
| 2010/0027807 A1 | 2/2010 | Jeon | |
| 2010/0046767 A1 | 2/2010 | Bayley et al. | |
| 2010/0062905 A1 | 3/2010 | Rottler et al. | |
| 2010/0076331 A1 | 3/2010 | Chan et al. | |
| 2010/0094658 A1 | 4/2010 | Mok et al. | |
| 2010/0099539 A1 | 4/2010 | Haataja | |
| 2010/0119093 A1 | 5/2010 | Uzuanis et al. | |
| 2010/0121700 A1 | 5/2010 | Wigder et al. | |
| 2010/0132044 A1 | 5/2010 | Kogan et al. | |
| 2010/0145220 A1 | 6/2010 | van Vliet | |
| 2010/0150378 A1 | 6/2010 | Lee et al. | |
| 2010/0161353 A1 | 6/2010 | Mayaud | |
| 2010/0222645 A1 | 9/2010 | Nadler et al. | |
| 2010/0292600 A1 | 11/2010 | Dibenedetto et al. | |
| 2010/0312138 A1 | 12/2010 | Regas | |
| 2011/0010195 A1 | 1/2011 | Cohn | |
| 2011/0057799 A1 | 3/2011 | Taneff | |
| 2011/0066051 A1 | 3/2011 | Moon et al. | |
| 2011/0071765 A1 | 3/2011 | Yodfat et al. | |
| 2011/0093481 A1 | 4/2011 | Hussam | |
| 2011/0098928 A1 | 4/2011 | Hoffman et al. | |
| 2011/0119088 A1 | 5/2011 | Gunn et al. | |
| 2011/0152656 A1 | 6/2011 | Weinert et al. | |
| 2011/0166631 A1 | 7/2011 | Breining | |
| 2011/0195383 A1 | 8/2011 | Weiss | |
| 2011/0214162 A1 | 9/2011 | Brakensiek et al. | |
| 2011/0218407 A1 | 9/2011 | Haberman et al. | |
| 2011/0245623 A1 | 10/2011 | Chutani et al. | |
| 2011/0307821 A1 | 12/2011 | Martens | |

(56) References Cited

U.S. PATENT DOCUMENTS

| | | |
|---|---|---|
| 2012/0002510 A1 | 1/2012 | Berman, Jr. |
| 2012/0023586 A1 | 1/2012 | Flickner et al. |
| 2012/0029303 A1 | 2/2012 | Shaya |
| 2012/0038651 A1 | 2/2012 | Case et al. |
| 2012/0041767 A1 | 2/2012 | Hoffman et al. |
| 2012/0059664 A1 | 3/2012 | Georgiev et al. |
| 2012/0065480 A1 | 3/2012 | Badilini et al. |
| 2012/0071770 A1 | 3/2012 | Grey et al. |
| 2012/0112908 A1 | 5/2012 | Prykaeri et al. |
| 2012/0116550 A1 | 5/2012 | Hoffman et al. |
| 2012/0185267 A1 | 7/2012 | Kamen et al. |
| 2012/0203124 A1 | 8/2012 | Lim |
| 2012/0215115 A1 | 8/2012 | Takahashi |
| 2012/0232929 A1 | 9/2012 | Experton |
| 2012/0245447 A1 | 9/2012 | Karan et al. |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0065569 A1 | 3/2013 | Leipzig et al. |
| 2013/0072765 A1 | 3/2013 | Kahn et al. |
| 2013/0073933 A1 | 3/2013 | Eppolito |
| 2013/0073960 A1 | 3/2013 | Eppolito et al. |
| 2013/0095459 A1 | 4/2013 | Tran |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0144653 A1 | 6/2013 | Poe et al. |
| 2013/0151285 A1 | 6/2013 | Mclaren et al. |
| 2013/0158416 A1 | 6/2013 | Hatlestad et al. |
| 2013/0191647 A1 | 7/2013 | Ferrara et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0231575 A1 | 9/2013 | Erkkila et al. |
| 2013/0231947 A1 | 9/2013 | Shusterman |
| 2013/0262155 A1 | 10/2013 | Hinkamp |
| 2013/0268398 A1 | 10/2013 | Agami et al. |
| 2013/0274628 A1 | 10/2013 | Fausti et al. |
| 2013/0304510 A1 | 11/2013 | Chen et al. |
| 2013/0304616 A1 | 11/2013 | Raleigh et al. |
| 2013/0317380 A1 | 11/2013 | Liley et al. |
| 2013/0325396 A1 | 12/2013 | Yuen et al. |
| 2013/0325511 A1 | 12/2013 | Neagle et al. |
| 2013/0332286 A1 | 12/2013 | Medelius et al. |
| 2014/0005947 A1 | 1/2014 | Jeon et al. |
| 2014/0019162 A1 | 1/2014 | Skowronski et al. |
| 2014/0037107 A1 | 2/2014 | Marino et al. |
| 2014/0038781 A1 | 2/2014 | Foley et al. |
| 2014/0046926 A1 | 2/2014 | Walton |
| 2014/0073486 A1 | 3/2014 | Ahmed et al. |
| 2014/0081118 A1 | 3/2014 | Reinhold et al. |
| 2014/0088995 A1 | 3/2014 | Damani |
| 2014/0100885 A1 | 4/2014 | Stern |
| 2014/0127996 A1 | 5/2014 | Park et al. |
| 2014/0129007 A1 | 5/2014 | Utter |
| 2014/0129243 A1 | 5/2014 | Utter |
| 2014/0135592 A1 | 5/2014 | Ohnemus et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0184422 A1 | 7/2014 | Mensinger et al. |
| 2014/0189510 A1 | 7/2014 | Ozcan |
| 2014/0197946 A1 | 7/2014 | Park et al. |
| 2014/0200426 A1 | 7/2014 | Taub et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1 | 9/2014 | Yuen |
| 2014/0297217 A1 | 10/2014 | Yuen |
| 2014/0327527 A1 | 11/2014 | Goldstein et al. |
| 2014/0336796 A1 | 11/2014 | Agnew |
| 2014/0344687 A1 | 11/2014 | Durham et al. |
| 2014/0354494 A1 | 12/2014 | Katz |
| 2014/0358012 A1 | 12/2014 | Richards et al. |
| 2014/0371887 A1 | 12/2014 | Hoffman et al. |
| 2015/0057942 A1 | 2/2015 | Self et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0142689 A1 | 5/2015 | Squires |
| 2015/0164349 A1 | 6/2015 | Gopalakrishnan et al. |
| 2015/0179186 A1 | 6/2015 | Swierk et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193217 A1 | 7/2015 | Xiang et al. |
| 2015/0196804 A1 | 7/2015 | Koduri et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0262499 A1 | 9/2015 | Wicka et al. |
| 2015/0286800 A1 | 10/2015 | Kanagala et al. |
| 2015/0287421 A1 | 10/2015 | Benway et al. |
| 2015/0288797 A1 | 10/2015 | Vincent |
| 2015/0288944 A1 | 10/2015 | Nistico et al. |
| 2015/0289823 A1 | 10/2015 | Rack-Gomer et al. |
| 2015/0297134 A1 | 10/2015 | Albert et al. |
| 2015/0324751 A1 | 11/2015 | Orenstein et al. |
| 2015/0347690 A1 | 12/2015 | Keen et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |
| 2016/0000379 A1 | 1/2016 | Pougatchev et al. |
| 2016/0019360 A1 | 1/2016 | Pahwa et al. |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0063215 A1 | 3/2016 | Zamer |
| 2016/0066842 A1 | 3/2016 | Kokkoneva et al. |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0103985 A1 | 4/2016 | Shim et al. |
| 2016/0106398 A1 | 4/2016 | Kuppuswami |
| 2016/0109961 A1 | 4/2016 | Parshionikar |
| 2016/0110523 A1 | 4/2016 | Francois |
| 2016/0132046 A1 | 5/2016 | Beoughter et al. |
| 2016/0132645 A1 | 5/2016 | Charpentier et al. |
| 2016/0135719 A1 | 5/2016 | Von Kraus et al. |
| 2016/0135731 A1 | 5/2016 | Drennan |
| 2016/0150978 A1 | 6/2016 | Yuen et al. |
| 2016/0166181 A1 | 6/2016 | Shennib |
| 2016/0166195 A1 | 6/2016 | Radecka et al. |
| 2016/0174857 A1 | 6/2016 | Eggers et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0210434 A1 | 7/2016 | Al-Sharif |
| 2016/0235325 A1 | 8/2016 | Chou |
| 2016/0235374 A1 | 8/2016 | Miller et al. |

(56) References Cited

U.S. PATENT DOCUMENTS

| | | |
|---|---|---|
| 2016/0249857 A1 | 9/2016 | Choi et al. |
| 2016/0250517 A1 | 9/2016 | Tilvis et al. |
| 2016/0256082 A1 | 9/2016 | Ely et al. |
| 2016/0263435 A1 | 9/2016 | Venkatraman et al. |
| 2016/0270717 A1 | 9/2016 | Luna et al. |
| 2016/0270740 A1 | 9/2016 | Raisoni et al. |
| 2016/0275310 A1 | 9/2016 | Edwards et al. |
| 2016/0275990 A1 | 9/2016 | Vassort |
| 2016/0285985 A1 | 9/2016 | Molettiere et al. |
| 2016/0287177 A1 | 10/2016 | Huppert et al. |
| 2016/0292373 A1 | 10/2016 | Spors et al. |
| 2016/0299769 A1 | 10/2016 | Hunter et al. |
| 2016/0301761 A1 | 10/2016 | Sanchez-Sandoval et al. |
| 2016/0301794 A1 | 10/2016 | Schlakman et al. |
| 2016/0302666 A1 | 10/2016 | Shaya |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0357616 A1 | 12/2016 | Yu et al. |
| 2016/0360100 A1 | 12/2016 | Kim et al. |
| 2016/0360972 A1 | 12/2016 | Kusakabe et al. |
| 2016/0367138 A1 | 12/2016 | Kim et al. |
| 2017/0000348 A1 | 1/2017 | Karsten et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0032168 A1 | 2/2017 | Kim |
| 2017/0039327 A1 | 2/2017 | Bitran et al. |
| 2017/0042485 A1 | 2/2017 | Chung et al. |
| 2017/0043214 A1 | 2/2017 | Higashi |
| 2017/0046024 A1 | 2/2017 | Dascola et al. |
| 2017/0046052 A1 | 2/2017 | Lee et al. |
| 2017/0053542 A1 | 2/2017 | Wilson et al. |
| 2017/0070833 A1 | 3/2017 | Shennib |
| 2017/0071551 A1 | 3/2017 | Jain et al. |
| 2017/0075551 A1 | 3/2017 | Robinson et al. |
| 2017/0084196 A1 | 3/2017 | Nusbaum et al. |
| 2017/0086693 A1 | 3/2017 | Peterson et al. |
| 2017/0091567 A1 | 3/2017 | Wang et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0147197 A1 | 5/2017 | Yang et al. |
| 2017/0150917 A1 | 6/2017 | Brief et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0181678 A1 | 6/2017 | Newberry |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0215811 A1 | 8/2017 | Newberry |
| 2017/0225034 A1 | 8/2017 | Kass et al. |
| 2017/0235443 A1 | 8/2017 | Suzuki |
| 2017/0237694 A1 | 8/2017 | Choudhary et al. |
| 2017/0243508 A1 | 8/2017 | Cheng et al. |
| 2017/0258455 A1 | 9/2017 | Qi |
| 2017/0274149 A1 | 9/2017 | Aeschlimann |
| 2017/0274267 A1 | 9/2017 | Blahnik |
| 2017/0287313 A1 | 10/2017 | Park et al. |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0300643 A1 | 10/2017 | Bezark et al. |
| 2017/0303844 A1 | 10/2017 | Baker et al. |
| 2017/0319184 A1 | 11/2017 | Sano |
| 2017/0329933 A1 | 11/2017 | Brust et al. |
| 2017/0330297 A1 | 11/2017 | Cronin et al. |
| 2017/0332980 A1 | 11/2017 | Fifield et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0032234 A1 | 2/2018 | Michalske |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0055490 A1 | 3/2018 | Lee et al. |
| 2018/0056130 A1 | 3/2018 | Bitran et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0081918 A1 | 3/2018 | Gravenites et al. |
| 2018/0096739 A1 | 4/2018 | Sano |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140927 A1 | 5/2018 | Kito et al. |
| 2018/0154212 A1 | 6/2018 | Park et al. |
| 2018/0157864 A1 | 6/2018 | Tribble et al. |
| 2018/0189077 A1 | 7/2018 | Gupta et al. |
| 2018/0211020 A1 | 7/2018 | Fukuda |
| 2018/0226150 A1 | 8/2018 | Hayter et al. |
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0279885 A1 | 10/2018 | Bulut |
| 2018/0336530 A1 | 11/2018 | Johnson et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0012898 A1 | 1/2019 | Wittrup |
| 2019/0014205 A1 | 1/2019 | Miloseski et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0108908 A1 | 4/2019 | Faulks et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0192086 A1 | 6/2019 | Menon et al. |
| 2019/0206538 A1 | 7/2019 | Xing et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0228847 A1 | 7/2019 | Soli |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0298230 A1 | 10/2019 | Nicholson et al. |
| 2019/0302995 A1 | 10/2019 | Robinson et al. |
| 2019/0336044 A1 | 11/2019 | Williams et al. |

(56) References Cited

U.S. PATENT DOCUMENTS

| | | |
|---|---|---|
| 2019/0336045 A1 | 11/2019 | Williams et al. |
| 2019/0339849 A1 | 11/2019 | Williams et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2020/0000441 A1 | 1/2020 | Lafon et al. |
| 2020/0054931 A1 | 2/2020 | Martin et al. |
| 2020/0069258 A1 | 3/2020 | Grinberg |
| 2020/0100693 A1 | 4/2020 | Velo |
| 2020/0126673 A1 | 4/2020 | Tanabe et al. |
| 2020/0203012 A1 | 6/2020 | Kamath et al. |
| 2020/0214650 A1 | 7/2020 | Lee et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0350052 A1 | 11/2020 | Saint et al. |
| 2020/0356687 A1 | 11/2020 | Salzman et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0068714 A1 | 3/2021 | Crowley et al. |
| 2021/0113137 A1 | 4/2021 | Soli et al. |
| 2021/0204815 A1 | 7/2021 | Koskela et al. |
| 2021/0225482 A1 | 7/2021 | Crowley et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375157 A1 | 12/2021 | Sundstrom et al. |
| 2021/0375450 A1 | 12/2021 | Felton et al. |
| 2022/0066902 A1 | 3/2022 | Narra et al. |
| 2022/0109932 A1 | 4/2022 | Felton et al. |
| 2022/0142515 A1 | 5/2022 | Crowley |
| 2022/0157143 A1 | 5/2022 | Panneer Selvam et al. |
| 2022/0160258 A1 | 5/2022 | Williams et al. |
| 2022/0273204 A1 | 9/2022 | Kamath et al. |
| 2023/0016144 A1 | 1/2023 | Dryer et al. |

FOREIGN PATENT DOCUMENTS

| | | |
|---|---|---|
| CN | 101107619 A | 1/2008 |
| CN | 102448555 A | 5/2012 |
| CN | 102790761 A | 11/2012 |
| CN | 103191557 A | 7/2013 |
| CN | 103403627 A | 11/2013 |
| CN | 103561640 A | 2/2014 |
| CN | 104720765 A | 6/2015 |
| CN | 105260078 A | 1/2016 |
| CN | 105388998 A | 3/2016 |
| CN | 105721667 A | 6/2016 |
| CN | 105980008 A | 9/2016 |
| CN | 106164808 A | 11/2016 |
| CN | 106371816 A | 2/2017 |
| CN | 106415559 A | 2/2017 |
| CN | 106537397 A | 3/2017 |
| CN | 106709235 A | 5/2017 |
| CN | 106725384 A | 5/2017 |
| CN | 107278138 A | 10/2017 |
| CN | 107361755 A | 11/2017 |
| CN | 107454831 A | 12/2017 |
| CN | 107591211 A | 1/2018 |
| CN | 107713981 A | 2/2018 |
| CN | 108604327 A | 9/2018 |
| CN | 109287140 A | 1/2019 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 2005-79814 A | 3/2005 |
| JP | 2006-107134 A | 4/2006 |
| JP | 2008-11865 A | 1/2008 |
| JP | 2010-517725 A | 5/2010 |
| JP | 2010-162297 A | 7/2010 |
| JP | 2010-181280 A | 8/2010 |
| JP | 2011-200575 A | 10/2011 |
| JP | 2012-59264 A | 3/2012 |
| JP | 2012-524640 A | 10/2012 |
| JP | 2012-239808 A | 12/2012 |
| JP | 2013-544140 A | 12/2013 |
| JP | 2015-73590 A | 4/2015 |
| JP | 2015-213686 A | 12/2015 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2016-538926 A | 12/2016 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-523554 A | 8/2018 |
| JP | 2018-191122 A | 11/2018 |
| KR | 10-2002-0060421 A | 7/2002 |
| KR | 10-2008-0051460 A | 6/2008 |
| KR | 10-2012-0023657 A | 3/2012 |
| KR | 10-2013-0093837 A | 8/2013 |
| KR | 10-2013-0111569 A | 10/2013 |
| KR | 10-2013-0111570 A | 10/2013 |
| KR | 10-2015-0115385 A | 10/2015 |
| KR | 10-1594486 B1 | 2/2016 |
| KR | 10-2016-0028351 A | 3/2016 |
| KR | 10-2016-0076264 A | 6/2016 |
| KR | 10-2016-0077199 A | 7/2016 |
| KR | 10-2017-0003608 A | 1/2017 |
| KR | 10-2017-0019040 A | 2/2017 |
| KR | 10-2017-0019745 A | 2/2017 |
| KR | 10-2017-0029014 A | 3/2017 |
| KR | 10-2018-0129188 A | 12/2018 |
| KR | 10-2019-0094795 A | 8/2019 |
| WO | 2001/096986 A2 | 12/2001 |
| WO | 2003/067202 A2 | 8/2003 |
| WO | 2006/046648 A1 | 5/2006 |
| WO | 2008/073359 A2 | 6/2008 |
| WO | 2009/095908 A2 | 8/2009 |
| WO | 2010/028320 A1 | 3/2010 |
| WO | 2010/126825 A1 | 11/2010 |
| WO | 2012/060588 A2 | 5/2012 |
| WO | 2012/061438 A2 | 5/2012 |
| WO | 2012/061440 A2 | 5/2012 |
| WO | 2013/103570 A1 | 7/2013 |
| WO | 2013/109916 A1 | 7/2013 |
| WO | 2014/006862 A1 | 1/2014 |
| WO | 2014/015378 A1 | 1/2014 |
| WO | 2014/207875 A1 | 12/2014 |
| WO | 2015/027133 A1 | 2/2015 |
| WO | 2015/084353 A1 | 6/2015 |
| WO | 2015/153803 A1 | 10/2015 |
| WO | 2015/183828 A1 | 12/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A1 | 11/2016 |
| WO | 2016/207745 A1 | 12/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2017/172046 A1 | 10/2017 |

(56) References Cited

FOREIGN PATENT DOCUMENTS

| WO | 2017/215203 A1 | 12/2017 |
|---|---|---|
| WO | 2018/132507 A1 | 7/2018 |
| WO | 2018/148356 A1 | 8/2018 |
| WO | 2018/213401 A1 | 11/2018 |
| WO | 2019/020977 A1 | 1/2019 |
| WO | 2019/168956 A1 | 9/2019 |

OTHER PUBLICATIONS

Extended European Search Report received for European Patent Application No. 22190169.7, dated Nov. 23, 2022, 11 pages.
Final Office Action received for U.S. Appl. No. 16/888,780, dated Nov. 25, 2022, 10 pages.
Intention to Grant received for European Patent Application No. 20182116.2, dated Nov. 11, 2022, 9 pages.
Invitation to Pay Search Fees received for European Patent Application No. 20746438.9, dated Dec. 2, 2022, 4 pages.
Invitation to Pay Search Fees received for European Patent Application No. 20760607.0, dated Nov. 21, 2022, 3 pages.
Non-Final Office Action received for U.S. Appl. No. 17/031,723, dated Dec. 5, 2022, 27 pages.
Office Action received for Australian Patent Application No. 2021266294, dated Nov. 11, 2022, 3 pages.
Advisory Action received for U.S. Appl. No. 16/144,864, dated Jul. 29, 2019, 6 pages.
Advisory Action received for U.S. Appl. No. 16/143,909, dated Nov. 7, 2019, 5 pages.
Advisory Action received for U.S. Appl. No. 16/143,997, dated Dec. 26, 2019, 7 pages.
Advisory Action received for U.S. Appl. No. 16/144,849, dated Aug. 12, 2019, 5 pages.
Advisory Action received for U.S. Appl. No. 16/144,864, dated Jul. 6, 2020, 6 pages.
Applicant-Initiated Interview Summary received for U.S. Appl. No. 16/138,809, dated Dec. 16, 2020, 7 pages.
Applicant-Initiated Interview Summary received for U.S. Appl. No. 16/138,809, dated Jun. 9, 2020, 4 pages.
Applicant-Initiated Interview Summary received for U.S. Appl. No. 16/143,997, dated Aug. 13, 2020, 3 pages.
Applicant-Initiated Interview Summary received for U.S. Appl. No. 16/143,997, dated May 3, 2021, 4 pages.
Applicant-Initiated Interview Summary received for U.S. Appl. No. 16/144,849, dated Jan. 21, 2020, 6 pages.
Applicant-Initiated Interview Summary received for U.S. Appl. No. 16/144,864, dated Apr. 29, 2020, 4 pages.
Applicant-Initiated Interview Summary received for U.S. Appl. No. 16/144,864, dated Jun. 22, 2020, 3 pages.
Applicant-Initiated Interview Summary received for U.S. Appl. No. 16/249,627, dated Jun. 2, 2021, 5 pages.
Applicant-Initiated Interview Summary received for U.S. Appl. No. 16/249,627, dated Mar. 23, 2022, 3 pages.
Applicant-Initiated Interview Summary received for U.S. Appl. No. 16/249,627, dated Oct. 6, 2021, 4 pages.
Applicant-Initiated Interview Summary received for U.S. Appl. No. 16/584,186, dated Feb. 3, 2020, 4 pages.
Applicant-Initiated Interview Summary received for U.S. Appl. No. 16/586,154, dated Apr. 14, 2021, 4 pages.
Applicant-Initiated Interview Summary received for U.S. Appl. No. 16/586,154, dated Dec. 11, 2020, 5 pages.
Applicant-Initiated Interview Summary received for U.S. Appl. No. 16/586,154, dated Mar. 11, 2020, 4 pages.
Applicant-Initiated Interview Summary received for U.S. Appl. No. 16/586,154, dated Sep. 3, 2021, 4 pages.
Applicant-Initiated Interview Summary received for U.S. Appl. No. 16/851,451, dated Aug. 5, 2022, 3 pages.
Applicant-Initiated Interview Summary received for U.S. Appl. No. 16/880,552, dated Apr. 21, 2021, 3 pages.
Applicant-Initiated Interview Summary received for U.S. Appl. No. 16/880,552, dated Dec. 16, 2020, 6 pages.
Applicant-Initiated Interview Summary received for U.S. Appl. No. 16/880,552, dated Oct. 20, 2020, 6 pages.
Applicant-Initiated Interview Summary received for U.S. Appl. No. 16/880,714, dated Feb. 26, 2021, 5 pages.
Applicant-Initiated Interview Summary received for U.S. Appl. No. 16/888,780, dated Aug. 2, 2022, 4 pages.
Applicant-Initiated Interview Summary received for U.S. Appl. No. 16/894,309, dated Jan. 26, 2021, 3 pages.
Applicant-Initiated Interview Summary received for U.S. Appl. No. 16/894,309, dated Jun. 25, 2021, 4 pages.
Applicant-Initiated Interview Summary received for U.S. Appl. No. 16/907,261, dated Dec. 16, 2020, 6 pages.
Applicant-Initiated Interview Summary received for U.S. Appl. No. 16/907,261, dated Jul. 16, 2021, 10 pages.
Applicant-Initiated Interview Summary received for U.S. Appl. No. 16/907,261, dated Mar. 25, 2021, 2 pages.
Applicant-Initiated Interview Summary received for U.S. Appl. No. 17/031,704, dated Feb. 9, 2021, 3 pages.
Applicant-Initiated Interview Summary received for U.S. Appl. No. 17/031,704, dated Jun. 25, 2021, 3 pages.
Applicant-Initiated Interview Summary received for U.S. Appl. No. 17/031,717, dated Jan. 29, 2021, 5 pages.
Applicant-Initiated Interview Summary received for U.S. Appl. No. 17/031,717, dated May 17, 2021, 5 pages.
Applicant-Initiated Interview Summary received for U.S. Appl. No. 17/031,717, dated Nov. 4, 2021, 5 pages.
Applicant-Initiated Interview Summary received for U.S. Appl. No. 17/031,723, dated Aug. 30, 2022, 4 pages.
Applicant-Initiated Interview Summary received for U.S. Appl. No. 17/031,723, dated Mar. 21, 2021, 5 pages.
Applicant-Initiated Interview Summary received for U.S. Appl. No. 17/031,779, dated Aug. 29, 2022, 2 pages.
Applicant-Initiated Interview Summary received for U.S. Appl. No. 17/031,779, dated Mar. 10, 2022, 2 pages.
Applicant-Initiated Interview Summary received for U.S. Appl. No. 17/041,415, dated Jun. 29, 2022, 2 pages.
Brief Communication regarding Oral Proceedings received for European Patent Application No. 13812320.3, mailed on Sep. 16, 2021, 2 pages.
Brief Communication regarding Oral Proceedings received for European Patent Application No. 20180581.9, mailed on Jan. 26, 2022, 1 page.
Brief Communication regarding Oral Proceedings received for European Patent Application No. 20180581.9, mailed on Nov. 30, 2021, 1 page.
Brief Communication regarding Oral Proceedings received for European Patent Application No. 20180592.6, mailed on Dec. 21, 2021, 1 page.
Brief Communication regarding Oral Proceedings received for European Patent Application No. 20180592.6, mailed on Jan. 26, 2022, 2 pages.
Brief Communication regarding Oral Proceedings received for European Patent Application No. 20182116.2, mailed on Apr. 13, 2022, 3 pages.
Casella Cel Casella, "The Casella dBadge2—World's First Truly Wireless Noise Dosimeter and Airwave App!", Retrieved from URL: <https://www.youtube.com/watch?v=Xvy2fl3cgYo>, May 27, 2015, 3 pages.
Certificate of Examination received for Australian Patent Application No. 2019100222, dated Aug. 29, 2019, 2 pages.
Chatrzarrin Hanieh, "Feature Extraction for the Differentiation of Dry and Wet Cough Sounds", Carleton University, Sep. 2011, 144 pages.
CNET, "Google Fit's automatic activity tracking is getting smarter on Android Wear", Available online at: https://www.youtube.com/watch?v=IttzlCid_d8, May 18, 2016, 1 page.
Cook James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.

(56) References Cited

OTHER PUBLICATIONS

Corrected Notice of Allowance received for U.S. Appl. No. 16/143,909, dated Feb. 20, 2020, 3 pages.
Corrected Notice of Allowance received for U.S. Appl. No. 16/143,909, dated Mar. 18, 2020, 3 pages.
Corrected Notice of Allowance received for U.S. Appl. No. 16/143,959, dated Dec. 13, 2019, 2 pages.
Corrected Notice of Allowance received for U.S. Appl. No. 16/143,997, dated Jul. 2, 2021, 2 pages.
Corrected Notice of Allowance received for U.S. Appl. No. 16/143,997, dated Jun. 4, 2021, 2 pages.
Corrected Notice of Allowance received for U.S. Appl. No. 16/143,997, dated Nov. 16, 2021, 2 pages.
Corrected Notice of Allowance received for U.S. Appl. No. 16/143,997, dated Oct. 21, 2021, 2 pages.
Corrected Notice of Allowance received for U.S. Appl. No. 16/584,186, dated Jul. 31, 2020, 2 pages.
Corrected Notice of Allowance received for U.S. Appl. No. 16/586,154, dated Oct. 27, 2021, 2 pages.
Corrected Notice of Allowance received for U.S. Appl. No. 16/880,552, dated Dec. 22, 2021, 2 pages.
Corrected Notice of Allowance received for U.S. Appl. No. 16/880,552, dated Dec. 23, 2020, 2 pages.
Corrected Notice of Allowance received for U.S. Appl. No. 16/880,552, dated Jul. 7, 2021, 2 pages.
Corrected Notice of Allowance received for U.S. Appl. No. 16/921,312, dated Dec. 7, 2021, 2 pages.
Corrected Notice of Allowance received for U.S. Appl. No. 16/921,312, dated Sep. 24, 2021, 2 pages.
Corrected Notice of Allowance received for U.S. Appl. No. 16/990,846, dated Feb. 9, 2022, 3 pages.
Corrected Notice of Allowance received for U.S. Appl. No. 17/031,704, dated Nov. 2, 2021, 7 pages.
Corrected Notice of Allowance received for U.S. Appl. No. 17/031,717, dated Apr. 15, 2022, 3 pages.
Corrected Notice of Allowance received for U.S. Appl. No. 17/031,717, dated May 19, 2022, 3 pages.
DC Rainmaker, "Garmin Fenix3 New Auto Climb Functionality", Available online at: https://www.youtube.com/watch?v=iuavOSNpVRc, Feb. 19, 2015, 1 page.
Decision on Appeal received for Korean Patent Application No. 10-2019-7025538, mailed on Feb. 24, 2021, 20 pages.
Decision to Grant received for Danish Patent Application No. PA201870379, dated Jul. 5, 2019, 2 pages.
Decision to Grant received for Danish Patent Application No. PA201870600, dated Oct. 17, 2019, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
Decision to Grant received for Danish Patent Application No. PA202070619, dated Aug. 11, 2022, 2 pages.
Decision to Grant received for European Patent Application No. 20180592.6, dated Sep. 1, 2022, 3 pages.
Decision to Refuse received for European Patent Application No. 13812320.3, dated Oct. 14, 2021, 4 pages.
Decision to Refuse received for European Patent Application No. 20180581.9, dated Apr. 13, 2022, 16 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.
European Search Report received for European Patent Application No. 20182116.2, dated Oct. 21, 2020, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 20180581.9, dated Aug. 12, 2020, 9 pages.
Extended European Search Report received for European Patent Application No. 20180592.6, dated Aug. 11, 2020, 10 pages.
Extended European Search Report received for European Patent Application No. 20203526.7, dated Jan. 29, 2021, 13 pages.
Final Office Action received for U.S. Appl. No. 15/167,699, dated Jun. 30, 2017, 8 pages.
Final Office Action received for U.S. Appl. No. 16/138,809, dated Aug. 27, 2020, 24 pages.
Final Office Action received for U.S. Appl. No. 16/143,909, dated Aug. 28, 2019, 20 pages.
Final Office Action received for U.S. Appl. No. 16/143,997, dated Feb. 9, 2021, 16 pages.
Final Office Action received for U.S. Appl. No. 16/143,997, dated Sep. 30, 2019, 16 pages.
Final Office Action received for U.S. Appl. No. 16/144,030, dated Feb. 13, 2020, 11 pages.
Final Office Action received for U.S. Appl. No. 16/144,030, dated Oct. 1, 2019, 13 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
Final Office Action received for U.S. Appl. No. 16/249,627, dated Feb. 14, 2022, 19 pages.
Final Office Action received for U.S. Appl. No. 16/586,154, dated Jul. 6, 2020, 27 pages.
Final Office Action received for U.S. Appl. No. 16/586,154, dated May 24, 2021, 29 pages.
Final Office Action received for U.S. Appl. No. 16/894,309, dated Feb. 24, 2021, 30 pages.
Final Office Action received for U.S. Appl. No. 16/907,261, dated Mar. 18, 2021, 20 pages.
Final Office Action received for U.S. Appl. No. 17/031,704, dated Apr. 1, 2021, 31 pages.
Final Office Action received for U.S. Appl. No. 17/031,717, dated Feb. 24, 2021, 23 pages.
Final Office Action received for U.S. Appl. No. 17/031,723, dated Jul. 12, 2022, 25 pages.
Final Office Action received for U.S. Appl. No. 17/031,779, dated Jul. 14, 2022, 19 pages.
Fitbit App, Available online at: <http://web.archive.org/web/20180114083150/https://www.fitbit.com/au/app>, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
Graphs and Charts, online available at: <https://www.teachervision.com/lesson-planning/graph-chart-teacher-resources, retrieved on Dec. 12, 2018, 4 pages.
Gupta Rajat, "Disable High Volume Warning (no root) in Samsung S7, S8 / Android 7.0", Online available at:<https://www.youtube.com/watch?v=9fKwRBtk-x8>, Retrieved on Nov. 26, 2020; esp. 2:04, Aug. 6, 2017, 1 page.
Haslam Oliver, "Stop Coronavirus in its Tracks by Using This Apple Watch App to Time Hand Washes", Available Online at: <https://www.imore.com/stop-coronavirus-its-tracks-using-apple-watch-app-time-hand-washes>, Mar. 12, 2020, 12 pages.
Intention to Grant received for Danish Patent Application No. PA201870379, dated May 2, 2019, 2 pages.
Intention to Grant received for Danish Patent Application No. PA201870600, dated Jul. 10, 2019, 2 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
Intention to Grant received for Danish Patent Application No. PA202070619, dated Jan. 17, 2022, 2 pages.
Intention to Grant received for European Patent Application No. 20180592.6, dated Apr. 20, 2022, 21 pages.
Intention to Grant received for European Patent Application No. 20182116.2, dated Jun. 2, 2022, 8 pages.

(56) References Cited

OTHER PUBLICATIONS

International Preliminary Report on Patentability received for PCT Patent Application No. PCT/US2013/073188, dated Jun. 16, 2016, 6 pages.
International Preliminary Report on Patentability received for PCT Patent Application No. PCT/US2019/014215, dated Aug. 6, 2020, 14 pages.
International Preliminary Report on Patentability received for PCT Patent Application No. PCT/US2019/019694, dated Sep. 24, 2020, 12 pages.
International Preliminary Report on Patentability received for PCT Patent Application No. PCT/US2019/024570, dated Nov. 19, 2020, 10 pages.
International Preliminary Report on Patentability received for PCT Patent Application No. PCT/US2020/025768, dated Dec. 16, 2021, 8 pages.
International Preliminary Report on Patentability received for PCT Patent Application No. PCT/US2020/035164, dated Dec. 16, 2021, 19 pages.
International Preliminary Report on Patentability received for PCT Patent Application No. PCT/US2020/035462, dated Dec. 16, 2021, 16 pages.
International Preliminary Report on Patentability received for PCT Patent Application No. PCT/US2020/035474, dated Dec. 16, 2021, 11 pages.
International Preliminary Report on Patentability received for PCT Patent Application No. PCT/US2020/042439, dated Jan. 27, 2022, 10 pages.
International Preliminary Report on Patentability received for PCT Patent Application No. PCT/US2020/070280, dated Mar. 17, 2022, 15 pages.
International Search Report and Written Opinion received for PCT Patent Application No. PCT/US2013/073188 dated Feb. 24, 2014, 8 pages.
International Search Report and Written Opinion received for PCT Patent Application No. PCT/US2019/014215, dated Jun. 4, 2019, 17 pages.
International Search Report and Written Opinion received for PCT Patent Application No. PCT/US2019/019694, dated Sep. 2, 2019, 17 pages.
International Search Report and Written Opinion received for PCT Patent Application No. PCT/US2019/024570, dated Aug. 8, 2019, 18 pages.
International Search Report and written Opinion received for PCT Patent Application No. PCT/US2020/025768, dated Aug. 10, 2020, 11 pages.
International Search Report and Written Opinion received for PCT Patent Application No. PCT/US2020/035164, dated Feb. 8, 2021, 26 pages.
International Search Report and Written Opinion received for PCT Patent Application No. PCT/US2020/035462, dated Sep. 11, 2020, 17 pages.
International Search Report and Written Opinion received for PCT Patent Application No. PCT/US2020/035474, dated Nov. 26, 2020, 16 pages.
International Search Report and Written Opinion received for PCT Patent Application No. PCT/US2020/042439, dated Oct. 9, 2020, 14 pages.
International Search Report and Written Opinion received for PCT Patent Application No. PCT/US2020/070280, dated Nov. 30, 2020, 20 pages.
International Search Report and Written Opinion received for PCT Patent Application No. PCT/US2021/035227, dated Oct. 6, 2021, 17 pages.
International Search Report and Written Opinion received for PCT Patent Application No. PCT/US2021/035504, dated Sep. 16, 2021, 12 pages.
International Search Report and Written Opinion received for PCT Patent Application No. PCT/US2021/048568, dated Jan. 7, 2022, 14 pages.

Invitation to Pay Additional Fees and Partial International Search Report received for PCT Patent Application No. PCT/US2019/014215, dated Apr. 12, 2019, 13 pages.
Invitation to Pay Additional Fees and Partial International Search Report received for PCT Patent Application No. PCT/US2020/035164, dated Oct. 16, 2020, 14 pages.
Invitation to Pay Additional Fees received for PCT Patent Application No. PCT/US2019/019694, dated Jul. 10, 2019, 12 pages.
Invitation to Pay Additional Fees received for PCT Patent Application No. PCT/US2020/035474, dated Oct. 2, 2020, 11 pages.
Invitation to Pay Additional Fees received for PCT Patent Application No. PCT/US2020/070280, dated Oct. 7, 2020, 12 pages.
Invitation to Pay Search Fees received for European Patent Application No. 19703582.7, dated Sep. 12, 2022, 3 pages.
Invitation to Pay Search Fees received for European Patent Application No. 19726205.8, dated Feb. 14, 2020, 5 pages.
Liaqat et al., "Challenges with Real-World Smartwatch based Audio Monitoring", WearSys'18, Munich, Germany, Available Online at: <https://doi.org/10.1145/3211960.3211977>, Jun. 10, 2018, 6 pages.
Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Lyles Taylor, "Wear OS Smartwatches are Now Sending Reminders to Wash Your Hands", Available Online at: <https://www.theverge.com/2020/4/14/21221294/google-wear-os-smartwatches-reminders-wash-your-hands>, Apr. 14, 2020, 2 pages.
Megadepot, "Casella dBadge2 Noise Dosimeter", Retrieved from URL: <https://www.youtube.com/watch?v=pHiHLiYCD08>, Jun. 12, 2018, 3 pages.
Minutes of the Oral Proceedings received for European Patent Application No. 20180581.9, mailed on Apr. 13, 2022, 10 pages.
Minutes of the Oral Proceedings received for European Patent Application No. 20180592.6, mailed on Apr. 7, 2022, 10 pages.
Minutes of the Oral Proceedings received for European Patent Application No. 20182116.2, mailed on May 24, 2022, 7 pages.
Moglia et al., "Evaluation of Smartphone Menstrual Cycle Tracking Applications Using an Adapted Applications Scoring System", Obstetrics and Gynecology, vol. 127. No. 6, Jun. 2016, pp. 1153-1160.
Multi-Set Bar Chart, The Data Visualization Catalogue, Available Online at: https://datavizcatalogue.com/methods/multiset_barchart.html, Feb. 8, 2014, 3 pages.
Myflo App, "Functional Medicine Period Tracker and Hormone Balancing App", Available online at <https://web.archive.org/web/20170127104125/https://myflotracker.com/>, Jan. 2017, 14 pages.
Myflo Tutorial, "How to change the start date of your current period", Available online at <https://www.youtube.com/watch?v=uQQ-odIBJB4>, Jan. 23, 2017, 3 pages.
Myflo Tutorial, "Setting and changing the end date of your period", Available online at <https://www.youtube.com/watch?v=UvAA4OgqL3E>, Jan. 23, 2017, 3 pages.
Non-Final Office Action received for U.S. Appl. No. 15/167,699, dated Oct. 21, 2016, 13 pages.
Non-Final Office Action received for U.S. Appl. No. 15/885,448, dated Apr. 16, 2020, 9 pages.
Non-Final Office Action received for U.S. Appl. No. 16/138,809, dated Feb. 28, 2020, 22 pages.
Non-Final Office Action received for U.S. Appl. No. 16/143,909, dated Apr. 19, 2019, 16 pages.
Non-Final Office Action received for U.S. Appl. No. 16/143,959, dated Apr. 17, 2019, 15 pages.
Non-Final Office Action received for U.S. Appl. No. 16/143,997, dated Jul. 27, 2020, 15 pages.
Non-Final Office Action received for U.S. Appl. No. 16/143,997, dated May 21, 2019, 15 pages.
Non-Final Office Action received for U.S. Appl. No. 16/144,030, dated Apr. 12, 2019, 8 pages.
Non-Final Office Action received for U.S. Appl. No. 16/144,030, dated Nov. 5, 2020, 5 pages.
Non-Final Office Action received for U.S. Appl. No. 16/144,849, dated Dec. 31, 2018, 28 pages.

(56) References Cited

OTHER PUBLICATIONS

Non-Final Office Action received for U.S. Appl. No. 16/144,849, dated Sep. 17, 2019, 9 pages.
Non-Final Office Action received for U.S. Appl. No. 16/144,864, dated Dec. 18, 2018, 19 pages.
Non-Final Office Action received for U.S. Appl. No. 16/144,864, dated Jan. 31, 2020, 29 pages.
Non-Final Office Action received for U.S. Appl. No. 16/249,627, dated Aug. 22, 2022, 21 pages.
Non-Final Office Action received for U.S. Appl. No. 16/249,627, dated Aug. 31, 2021, 18 pages.
Non-Final Office Action received for U.S. Appl. No. 16/249,627, dated Mar. 11, 2021, 21 pages.
Non-Final Office Action received for U.S. Appl. No. 16/584,186, dated Dec. 6, 2019, 13 pages.
Non-Final Office Action received for U.S. Appl. No. 16/586,154, dated Dec. 9, 2019, 23 pages.
Non-Final Office Action received for U.S. Appl. No. 16/586,154, dated Dec. 28, 2020, 26 pages.
Non-Final Office Action received for U.S. Appl. No. 16/851,451, dated May 9, 2022, 26 pages.
Non-Final Office Action received for U.S. Appl. No. 16/880,552, dated Feb. 19, 2021, 11 pages.
Non-Final Office Action received for U.S. Appl. No. 16/880,552, dated Jul. 23, 2020, 19 pages.
Non-Final Office Action received for U.S. Appl. No. 16/880,714, dated Oct. 28, 2020, 11 pages.
Non-Final Office Action received for U.S. Appl. No. 16/888,780, dated Apr. 20, 2022, 22 pages.
Non-Final Office Action received for U.S. Appl. No. 16/894,309, dated Oct. 15, 2020, 24 pages.
Non-Final Office Action received for U.S. Appl. No. 16/907,261, dated Sep. 30, 2020, 22 pages.
Non-Final Office Action received for U.S. Appl. No. 16/953,781, dated Jul. 26, 2022, 9 pages.
Non-Final Office Action received for U.S. Appl. No. 16/990,846, dated May 10, 2021, 16 pages.
Non-Final Office Action received for U.S. Appl. No. 17/031,704, dated Dec. 10, 2020, 30 pages.
Non-Final Office Action received for U.S. Appl. No. 17/031,717, dated Nov. 19, 2020, 22 pages.
Non-Final Office Action received for U.S. Appl. No. 17/031,717, dated Sep. 14, 2021, 35 pages.
Non-Final Office Action received for U.S. Appl. No. 17/031,723, dated Jan. 24, 2022, 17 pages.
Non-Final Office Action received for U.S. Appl. No. 17/031,779, dated Feb. 16, 2022, 17 pages.
Non-Final Office Action received for U.S. Appl. No. 17/041,415, dated Mar. 29, 2022, 11 pages.
Notice from the European Patent Office dated Oct. 1, 2007 Concerning Business Methods, Official Journal EPO, available online at <http://archive.epo.org/epo/pubs/oj007/11_07/11_5927.pdf>, Nov. 2007, pp. 592-593.
Notice of Acceptance received for Australian Patent Application No. 2013406817, dated Nov. 21, 2017, 3 pages.
Notice of Acceptance received for Australian Patent Application No. 2018201260, dated Jan. 15, 2020, 3 pages.
Notice of Acceptance received for Australian Patent Application No. 2019210192, dated Dec. 2, 2021, 3 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.
Notice of Acceptance received for Australian Patent Application No. 2020239692, dated Apr. 6, 2022, 3 pages.
Notice of Acceptance received for Australian Patent Application No. 2020239740, dated Feb. 22, 2022, 3 pages.
Notice of Acceptance received for Australian Patent Application No. 2020256382, dated Aug. 3, 2021, 3 pages.
Notice of Acceptance received for Australian Patent Application No. 2020288147, dated Dec. 22, 2021, 3 pages.
Notice of Allowance received for Chinese Patent Application No. 201380081315.7, dated Jan. 4, 2019, 2 pages.
Notice of Allowance received for Chinese Patent Application No. 201910972529.2, dated Sep. 14, 2020, 6 pages.
Notice of Allowance received for Chinese Patent Application No. 202010606407.4, dated Jan. 24, 2022, 2 pages.
Notice of Allowance received for Chinese Patent Application No. 202010618569.X, dated Jan. 7, 2022, 2 pages.
Notice of Allowance received for Japanese Patent Application No. 2018-184532, dated Jan. 17, 2022, 4 pages.
Notice of Allowance received for Japanese Patent Application No. 2019-162293, dated Apr. 9, 2021, 4 pages.
Notice of Allowance received for Japanese Patent Application No. 2020-104679, dated Jan. 4, 2021, 4 pages.
Notice of Allowance received for Japanese Patent Application No. 2020-153166, dated Sep. 13, 2021, 4 pages.
Notice of Allowance received for Japanese Patent Application No. 2020-160023, dated Apr. 11, 2022, 4 pages.
Notice of Allowance received for Japanese Patent Application No. 2020-547369, dated Jul. 16, 2021, 4 pages.
Notice of Allowance received for Japanese Patent Application No. 2020-551585, dated Jul. 22, 2022, 4 pages.
Notice of Allowance received for Japanese Patent Application No. 2020-560883, dated Oct. 29, 2021, 4 pages.
Notice of Allowance received for Japanese Patent Application No. 2021-571467, dated Apr. 11, 2022, 4 pages.
Notice of Allowance received for Korean Patent Application No. 10-2016-7014353, dated Aug. 2, 2018, 3 pages.
Notice of Allowance received for Korean Patent Application No. 10-2018-7032096, dated Dec. 12, 2018, 4 pages.
Notice of Allowance received for Korean Patent Application No. 10-2019-7025538, dated Mar. 10, 2021, 5 pages.
Notice of Allowance received for Korean Patent Application No. 10-2020-7023277, dated Jul. 18, 2022, 5 pages.
Notice of Allowance received for Korean Patent Application No. 10-2020-7026035, dated Aug. 23, 2021, 4 pages.
Notice of Allowance received for Korean Patent Application No. 10-2020-7026391, dated May 11, 2021, 3 pages.
Notice of Allowance received for Korean Patent Application No. 10-2020-7026453, dated May 11, 2021, 3 pages.
Notice of Allowance received for Korean Patent Application No. 10-2021-7038005, dated Dec. 14, 2021, 4 pages.
Notice of Allowance received for Korean Patent Application No. 10-2021-7042504, dated Jan. 17, 2022, 6 pages.
Notice of Allowance received for Korean Patent Application No. 10-2022-7008569, dated May 19, 2022, 5 pages.
Notice of Allowance received for U.S. Appl. No. 15/167,699, dated Oct. 27, 2017, 8 pages.
Notice of Allowance received for U.S. Appl. No. 15/885,448, dated Jun. 16, 2020, 5 pages.
Notice of Allowance received for U.S. Appl. No. 16/138,809, dated Apr. 16, 2021, 11 pages.
Notice of Allowance received for U.S. Appl. No. 16/138,809, dated Jul. 20, 2021, 6 pages.
Notice of Allowance received for U.S. Appl. No. 16/143,909, dated Jan. 21, 2020, 9 pages.
Notice of Allowance received for U.S. Appl. No. 16/143,959, dated Oct. 31, 2019, 10 pages.
Notice of Allowance received for U.S. Appl. No. 16/143,997, dated May 13, 2021, 10 pages.
Notice of Allowance received for U.S. Appl. No. 16/143,997, dated Sep. 30, 2021, 8 pages.
Notice of Allowance received for U.S. Appl. No. 16/144,030, dated Apr. 5, 2021, 8 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Feb. 9, 2021, 13 pages.

(56) References Cited

OTHER PUBLICATIONS

Notice of Allowance received for U.S. Appl. No. 16/144,864, dated Jul. 28, 2020, 27 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/584,186, dated Mar. 24, 2020, 10 pages.
Notice of Allowance received for U.S. Appl. No. 16/586,154, dated Oct. 15, 2021, 8 pages.
Notice of Allowance received for U.S. Appl. No. 16/880,552, dated Dec. 1, 2020, 7 pages.
Notice of Allowance received for U.S. Appl. No. 16/880,552, dated Jul. 23, 2021, 5 pages.
Notice of Allowance received for U.S. Appl. No. 16/880,552, dated May 12, 2021, 7 pages.
Notice of Allowance received for U.S. Appl. No. 16/880,552, dated Nov. 24, 2021, 5 pages.
Notice of Allowance received for U.S. Appl. No. 16/880,714, dated Jun. 9, 2021, 6 pages.
Notice of Allowance received for U.S. Appl. No. 16/880,714, dated Mar. 19, 2021, 7 pages.
Notice of Allowance received for U.S. Appl. No. 16/894,309, dated Feb. 25, 2022, 9 pages.
Notice of Allowance received for U.S. Appl. No. 16/894,309, dated Nov. 5, 2021, 12 pages.
Notice of Allowance received for U.S. Appl. No. 16/907,261, dated Aug. 13, 2021, 8 pages.
Notice of Allowance received for U.S. Appl. No. 16/907,261, dated Sep. 28, 2021, 6 pages.
Notice of Allowance received for U.S. Appl. No. 16/921,312, dated Nov. 29, 2021, 5 pages.
Notice of Allowance received for U.S. Appl. No. 16/921,312, dated Sep. 14, 2021, 9 pages.
Notice of Allowance received for U.S. Appl. No. 16/990,846, dated Jan. 20, 2022, 6 pages.
Notice of Allowance received for U.S. Appl. No. 16/990,846, dated Sep. 22, 2021, 9 pages.
Notice of Allowance received for U.S. Appl. No. 17/031,704, dated Jul. 21, 2021, 10 pages.
Notice of Allowance received for U.S. Appl. No. 17/031,717, dated Jul. 7, 2022, 12 pages.
Notice of Allowance received for U.S. Appl. No. 17/031,717, dated Mar. 16, 2022, 12 pages.
Notice of Allowance received for U.S. Appl. No. 17/031,727, dated Dec. 24, 2020, 12 pages.
Notice of Allowance received for U.S. Appl. No. 17/031,727, dated Jun. 25, 2021, 6 pages.
Notice of Allowance received for U.S. Appl. No. 17/031,727, dated Mar. 12, 2021, 7 pages.
Notice of Allowance received for U.S. Appl. No. 17/041,415, dated Aug. 31, 2022, 7 pages.
Notice of Allowance received for U.S. Appl. No. 17/317,084, dated Aug. 29, 2022, 10 pages.
Office Action received for Australian Patent Application No. 2013406817, dated Aug. 1, 2017, 3 pages.
Office Action received for Australian Patent Application No. 2013406817, dated Nov. 14, 2016, 4 pages.
Office Action received for Australian Patent Application No. 2018201260, dated Feb. 12, 2019, 6 pages.
Office Action received for Australian Patent Application No. 2018201260, dated Jul. 17, 2019, 3 pages.
Office Action received for Australian Patent Application No. 2018201260, dated Sep. 5, 2019, 5 pages.
Office Action received for Australian Patent Application No. 2019100222, dated May 24, 2019, 6 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019210192, dated May 25, 2021, 4 pages.
Office Action received for Australian Patent Application No. 2019210192, dated Sep. 9, 2021, 4 pages.
Office Action received for Australian Patent Application No. 2019222943, dated Oct. 3, 2019, 3 pages.
Office Action received for Australian Patent Application No. 2019234289, dated Jul. 20, 2021, 4 pages.
Office Action received for Australian Patent Application No. 2019234289, dated Mar. 16, 2021, 8 pages.
Office Action received for Australian Patent Application No. 2019234289, dated Nov. 1, 2021, 4 pages.
Office Action received for Australian Patent Application No. 2019234289, dated Nov. 2, 2020, 6 pages.
Office Action received for Australian Patent Application No. 2020230340, dated Mar. 2, 2021, 6 pages.
Office Action received for Australian Patent Application No. 2020230340, dated May 27, 2021, 5 pages.
Office Action received for Australian Patent Application No. 2020230340, dated Nov. 2, 2020, 5 pages.
Office Action received for Australian Patent Application No. 2020230340, dated Oct. 11, 2021, 4 pages.
Office Action received for Australian Patent Application No. 2020239692, dated Jan. 27, 2022, 3 pages.
Office Action received for Australian Patent Application No. 2020239692, dated Jul. 20, 2021, 5 pages.
Office Action received for Australian Patent Application No. 2020239740, dated Jul. 9, 2021, 4 pages.
Office Action received for Australian Patent Application No. 2020239740, dated Sep. 28, 2021, 5 pages.
Office Action received for Australian Patent Application No. 2020256383, dated Jun. 4, 2021, 3 pages.
Office Action received for Chinese Patent Application No. 201380081315.7, dated Aug. 16, 2018, 6 pages.
Office Action received for Chinese Patent Application No. 201380081315.7, dated Mar. 2, 2018, 12 pages.
Office Action received for Chinese Patent Application No. 201910858933.7, dated Aug. 18, 2020, 14 pages.
Office Action received for Chinese Patent Application No. 201910858933.7, dated Dec. 30, 2021, 9 pages.
Office Action received for Chinese Patent Application No. 201910858933.7, dated Jun. 29, 2021, 8 pages.
Office Action received for Chinese Patent Application No. 201910972529.2, dated Jun. 28, 2020, 8 pages.
Office Action received for Chinese Patent Application No. 202010606407.4, dated Jan. 27, 2021, 16 pages.
Office Action received for Chinese Patent Application No. 202010606407.4, dated Jun. 2, 2021, 12 pages.
Office Action received for Chinese Patent Application No. 202010606407.4, dated Nov. 18, 2021, 6 pages.
Office Action received for Chinese Patent Application No. 202010618240.3, dated Dec. 3, 2021, 23 pages.
Office Action received for Chinese Patent Application No. 202010618240.3, dated Mar. 29, 2021, 21 pages.
Office Action received for Chinese Patent Application No. 202010618240.3, dated May 25, 2022, 20 pages.
Office Action received for Chinese Patent Application No. 202010618569.X, dated Mar. 12, 2021, 14 pages.
Office Action received for Chinese Patent Application No. 202010618569.X, dated Sep. 7, 2021, 7 pages.
Office Action received for Chinese Patent Application No. 202011220489.5, dated Apr. 25, 2022, 15 pages.

(56) References Cited

OTHER PUBLICATIONS

Office Action received for Chinese Patent Application No. 202011220489.5, dated Dec. 1, 2021, 19 pages.
Office Action received for Chinese Patent Application No. 202011220489.5, dated Jun. 1, 2021, 12 pages.
Office Action received for Chinese Patent Application No. 202111611270.2, dated May 10, 2022, 16 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870599, dated Dec. 20, 2019, 5 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jan. 14, 2020, 3 pages.
Office Action received for Danish Patent Application No. PA201870601, dated Jun. 25, 2019, 3 pages.
Office Action received for Danish Patent Application No. PA201870602, dated Feb. 5, 2020, 3 pages.
Office Action received for Danish Patent Application No. PA201870602, dated Jun. 26, 2019, 3 pages.
Office Action received for Danish Patent Application No. PA201970534, dated Feb. 16, 2021, 2 pages.
Office Action received for Danish Patent Application No. PA201970534, dated Jun. 29, 2020, 2 pages.
Office Action received for Danish Patent Application No. PA202070335, dated Jun. 11, 2021, 4 pages.
Office Action received for Danish Patent Application No. PA202070335, dated Nov. 17, 2021, 6 pages.
Office Action received for Danish Patent Application No. PA202070395, dated Dec. 15, 2021, 5 pages.
Office Action received for Danish Patent Application No. PA202070619, dated Aug. 27, 2021, 12 pages.
Office Action received for Danish Patent Application No. PA202070619, dated Oct. 14, 2021, 3 pages.
Office Action received for Danish Patent Application No. PA202070620, dated May 10, 2021, 5 pages.
Office Action received for Danish Patent Application No. PA202070620, dated Nov. 19, 2021, 2 pages.
Office Action received for European Patent Application No. 19721883.7, dated Jan. 10, 2020, 4 pages.
Office Action received for European Patent Application No. 19721883.7, dated Jun. 15, 2021, 9 pages.
Office Action received for European Patent Application No. 19721883.7, dated May 28, 2020, 11 pages.
Office Action received for European Patent Application No. 19726205.8, dated Jun. 26, 2020, 9 pages.
Office Action received for European Patent Application No. 20180581.9, dated Apr. 1, 2021, 11 pages.
Office Action received for European Patent Application No. 20180592.6, dated Apr. 1, 2021, 11 pages.
Office Action received for European Patent Application No. 20182116.2, dated May 25, 2021, 9 pages.
Office Action received for European Patent Application No. 20182116.2, dated Nov. 6, 2020, 9 pages.
Office Action received for European Patent Application No. 20203526.7, dated Nov. 23, 2021, 9 pages.
Office Action received for European Patent Application No. 13812320.3, dated Mar. 28, 2018, 7 pages.
Office Action received for Indian Patent Application No. 201617016494, dated Apr. 27, 2020, 7 pages.
Office Action received for Indian Patent Application No. 202014041484, dated Dec. 8, 2021, 8 pages.
Office Action received for Japanese Patent Application No. 2018-184532, dated Mar. 1, 2021, 11 pages.
Office Action received for Japanese Patent Application No. 2019-162293, dated Jan. 31, 2020, 8 pages.
Office Action received for Japanese Patent Application No. 2019-162293, dated Jul. 27, 2020, 9 pages.
Office Action received for Japanese Patent Application No. 2020-104679, dated Sep. 18, 2020, 13 pages.
Office Action received for Japanese Patent Application No. 2020-153166, dated May 31, 2021, 6 pages.
Office Action received for Japanese Patent Application No. 2020-160023, dated Jan. 17, 2022, 11 pages.
Office Action received for Japanese Patent Application No. 2020-547369, dated Apr. 9, 2021, 4 pages.
Office Action received for Japanese Patent Application No. 2020-551585, dated Jan. 6, 2022, 11 pages.
Office Action received for Japanese Patent Application No. 2021-167557, dated Aug. 15, 2022, 5 pages.
Office Action received for Korean Patent Application No. 10-2016-7014353, dated Mar. 21, 2018, 11 pages.
Office Action received for Korean Patent Application No. 10-2019-7025538, dated Aug. 15, 2020, 8 pages.
Office Action received for Korean Patent Application No. 10-2019-7025538, dated Feb. 17, 2020, 12 pages.
Office Action received for Korean Patent Application No. 10-2020-0124134, dated Jul. 28, 2022, 22 pages.
Office Action received for Korean Patent Application No. 10-2020-7023277, dated Jan. 26, 2022, 11 pages.
Office Action received for Korean Patent Application No. 10-2020-7026035, dated Feb. 19, 2021, 13 pages.
Office Action received for Korean Patent Application No. 10-2020-7026391, dated Jan. 27, 2021, 5 pages.
Office Action received for Korean Patent Application No. 10-2020-7026453, dated Jan. 27, 2021, 5 pages.
Office Action received for Korean Patent Application No. 10-2020-7033395, dated Aug. 29, 2022, 11 pages.
Peters Jay, "Samsung's Smartwatches Get a Hand-Washing Reminder and Timer App", Available Online at: <https://www.theverge.com/2020/4/17/21225205/samsung-smartwatch-galaxy-active-hand-washing-timer-reminder-app>, Apr. 17, 2020, 2 pages.
Result of Consultation received for European Patent Application No. 19721883.7, mailed on Oct. 7, 2020, 3 pages.
Result of Consultation received for European Patent Application No. 19726205.8, mailed on Mar. 15, 2021, 19 pages.
Result of Consultation received for European Patent Application No. 20180581.9, mailed on Jan. 21, 2022, 14 pages.
Result of Consultation received for European Patent Application No. 20180592.6, mailed on Jan. 26, 2022, 18 pages.
Rizknows, "TomTom Multisport Cardio Review", Online available at:—https://www.youtube.com/watch?v=WoVCzLrSN9A, Sep. 4, 2015, 1 page.
Schoon Ben, "Wear OS Now Sends a Reminder to Wash Your Hands Every Few Hours", Available Online at: <https://9to5google.com/2020/04/14/wear-os-wash-hands-reminder-coronavirus/>, Apr. 14, 2020, 7 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.
Search Report and Opinion received for Danish Patent Application No. PA201870602, dated Dec. 19, 2018, 8 pages.
Search Report and Opinion received for Danish Patent Application No. PA201970534, dated Sep. 23, 2019, 6 pages.

(56) References Cited

OTHER PUBLICATIONS

Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Search Report and Opinion received for Danish Patent Application No. PA202070619, dated Dec. 2, 2020, 11 pages.
Search Report and Opinion received for Danish Patent Application No. PA202070620, dated Dec. 11, 2020, 9 pages.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online Available at: https://www.youtube.com/watch?v=ZkPptnnXEiQ, Apr. 29, 2017, 2 pages.
Sportstechguides, "Garmin Fenix 5: How to Set Up Run Alerts", Online Available at: https://www.youtube.com/watch?v=gSMwv8vlhB4, May 13, 2017, 2 pages.
Studiosixdigital, "Dosimeter", Retrieved from URL: <https://studiosixdigital.com/audiotools-modules-2/spl-modules/dosimeter.html>, Mar. 3, 2017, 6 pages.
Summons to Attend Oral Proceedings received for European Patent Application No. 13812320.3, mailed on Mar. 12, 2021, 9 pages.
Summons to Attend Oral Proceedings received for European Patent Application No. 19726205.8, mailed on Oct. 29, 2020, 13 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Summons to Attend Oral Proceedings received for European Patent Application No. 20182116.2, mailed on Dec. 21, 2021, 7 pages.
Summons to Attend Oral Proceedings received for European Patent Application No. 20203526.7, mailed on Jun. 23, 2022, 9 pages.
Supplemental Notice of Allowance received for U.S. Appl. No. 16/144,849, dated Mar. 31, 2020, 2 pages.
Supplemental Notice of Allowance received for U.S. Appl. No. 16/880,714, dated Sep. 16, 2021, 2 pages.
Supplemental Notice of Allowance received for U.S. Appl. No. 16/894,309, dated Apr. 8, 2022, 3 pages.
Supplemental Notice of Allowance received for U.S. Appl. No. 16/894,309, dated Dec. 24, 2021, 2 pages.
Supplemental Notice of Allowance received for U.S. Appl. No. 16/894,309, dated Jan. 25, 2022, 2 pages.
Supplemental Notice of Allowance received for U.S. Appl. No. 17/031,727, dated Jan. 15, 2021, 2 pages.
Supplemental Notice of Allowance received for U.S. Appl. No. 17/041,415, dated Sep. 20, 2022, 2 pages.
Supplemental Notice of Allowance received for U.S. Appl. No. 17/317,084, dated Sep. 20, 2022, 2 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at: https://www.youtube.com/watch?v=aixfoCnS0OU, Mar. 19, 2018, 2 pages.
Tech, Kalyani, "I See Some problems in Honor Band 5", Retrieved from: https://www.youtube.com/watch?v=5XPnYJFqajl, May 19, 2020, 1 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Ticks, Smartwatch, "Senbono S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
TomTom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Visual Pace Alarm app, Available Online at: https://apps.garmin.com/en-US/apps/3940f3a2-4847-4078-a911-d77422966c82, Oct. 19, 2016, 1 page.
Weiyu et al., "A Multi-Identities Authentication and Authorization Schema in Cloud Computing", Aug. 20, 2012, pp. 7-10.
Wesley, "Apple Watch Series 1", online available at: http://toolbox.info/blog/archives/1737-unknown.html, May 28, 2015, 5 pages.
Youtube, "Apple Watch Series 3", Online available at: https://www.youtube.com/watch?v=iBPr9gEfkK8, Nov. 21, 2017, 15 pages.
Zlelik, "Garmin Fenix 5 Open Water Swimming Activity Demo", Online Available at: https://www.youtube.com/watch?v=iSVhdvw2dcs, Jun. 9, 2017, 1 page.
Applicant-Initiated Interview Summary received for U.S. Appl. No. 16/953,781, dated Oct. 31, 2022, 12 pages.
Brief Communication Regarding Oral Proceedings received for European Patent Application No. 20746438.9, mailed on Nov. 7, 2022, 1 page.
Notice of Allowance received for U.S. Appl. No. 16/953,781, dated Nov. 9, 2022, 7 pages.
Office Action received for European Patent Application No. 20746438.9, dated Oct. 31, 2022, 7 pages.
Advisory Action received for U.S. Appl. No. 17/031,779, dated Oct. 20, 2022, 5 pages.
Applicant-Initiated Interview Summary received for U.S. Appl. No. 16/249,627, dated Sep. 28, 2022, 4 pages.
Final Office Action received for U.S. Appl. No. 16/851,451, dated Oct. 20, 2022, 31 pages.
Notice of Allowance received for Chinese Patent Application No. 202111611270.2, dated Sep. 21, 2022, 4 pages (1 page of English Translation and 3 pages of Official Copy).
Office Action received for Australian Patent Application No. 2021261861, dated Oct. 14, 2022, 5 pages.
Office Action received for Chinese Patent Application No. 202010618240.3, dated Sep. 21, 2022, 16 pages (9 pages of English Translation and 7 pages of Official Copy).
Office Action received for Chinese Patent Application No. 202210004176.9, dated Sep. 28, 2022, 12 pages (6 pages of English Translation and 6 pages of Official Copy).
Office Action received for Danish Patent Application No. PA202070395, dated Oct. 7, 2022, 4 pages.
Supplemental Notice of Allowance received for U.S. Appl. No. 17/041,415, dated Oct. 13, 2022, 2 pages.
Notice of Allowance received for Japanese Patent Application No. 2021-167557, dated Jan. 27, 2023, 4 pages (1 page of English Translation and 3 pages of Official Copy).
Office Action received for European Patent Application No. 20746438.9, dated Feb. 1, 2023, 9 pages.
Office Action received for European Patent Application No. 20760607.0, dated Feb. 1, 2023, 13 pages.
Applicant-Initiated Interview Summary received for U.S. Appl. No. 17/031,723, dated Jan. 23, 2023, 4 pages.
Brief Communication Regarding Oral Proceedings received for European Patent Application No. 20203526.7, mailed on Jan. 18, 2023, 1 page.
Non-Final Office Action received for U.S. Appl. No. 16/249,627, dated Jan. 19, 2023, 19 pages.
Notice of Allowance received for U.S. Appl. No. 17/031,779, dated Feb. 1, 2023, 11 pages.
Office Action received for Korean Patent Application No. 10-2022-7036381, dated Jan. 6, 2023, 10 pages (5 pages of English Translation and 5 pages of Official Copy).
Supplemental Notice of Allowance received for U.S. Appl. No. 17/317,084, dated Jan. 19, 2023, 2 pages.
Notice of Allowance received for U.S. Appl. No. 17/317,084, dated Jan. 6, 2023, 6 pages.
Office Action received for Australian Patent Application No. 2021261861, dated Jan. 12, 2023, 4 pages.
Office Action received for Australian Patent Application No. 2022202459, dated Jan. 6, 2023, 3 pages.

(56) References Cited

OTHER PUBLICATIONS

Office Action received for Chinese Patent Application No. 201910204981.4, dated Nov. 29, 2022, 14 pages (5 pages of English Translation and 9 pages of Official Copy).
Office Action received for European Patent Application No. 19703582.7, dated Jan. 11, 2023, 11 pages.
International Preliminary Report on Patentability received for PCT Patent Application No. PCT/US2021/035227, dated Dec. 15, 2022, 10 pages.
International Preliminary Report on Patentability received for PCT Patent Application No. PCT/US2021/035504, dated Dec. 15, 2022, 8 pages.
Office Action received for Australian Patent Application No. 2020313970, dated Dec. 22, 2022, 3 pages.
Office Action received for Japanese Patent Application No. 2021-192437, dated Dec. 16, 2022, 4 pages (2 pages of English Translation and 2 pages of Official Copy).
Applicant-Initiated Interview Summary received for U.S. Appl. No. 16/249,627, dated Mar. 1, 2023, 4 pages.
International Preliminary Report on Patentability received for PCT Patent Application No. PCT/US2021/048568, dated Mar. 9, 2023, 11 pages.
Non-Final Office Action received for U.S. Appl. No. 16/851,451, dated Feb. 24, 2023, 28 pages.
Non-Final Office Action received for U.S. Appl. No. 17/337,147, dated Feb. 21, 2023, 15 pages.
Notice of Allowance received for U.S. Appl. No. 16/953,781, dated Feb. 27, 2023, 5 pages.
Office Action received for Australian Patent Application No. 2022201823, dated Mar. 9, 2023, 3 pages.
Office Action received for Australian Patent Application No. 2022204568, dated Mar. 11, 2023, 4 pages.

* cited by examiner

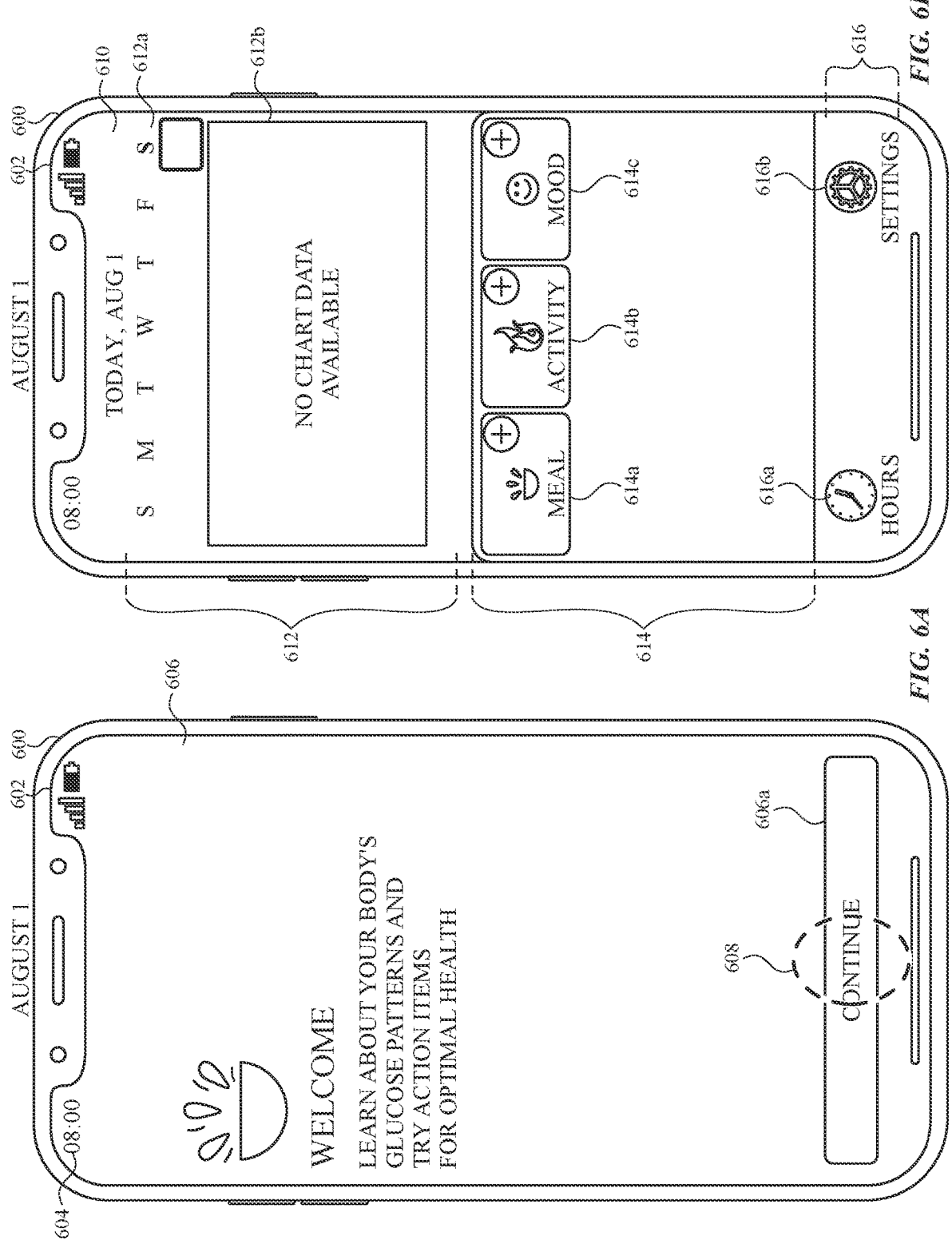

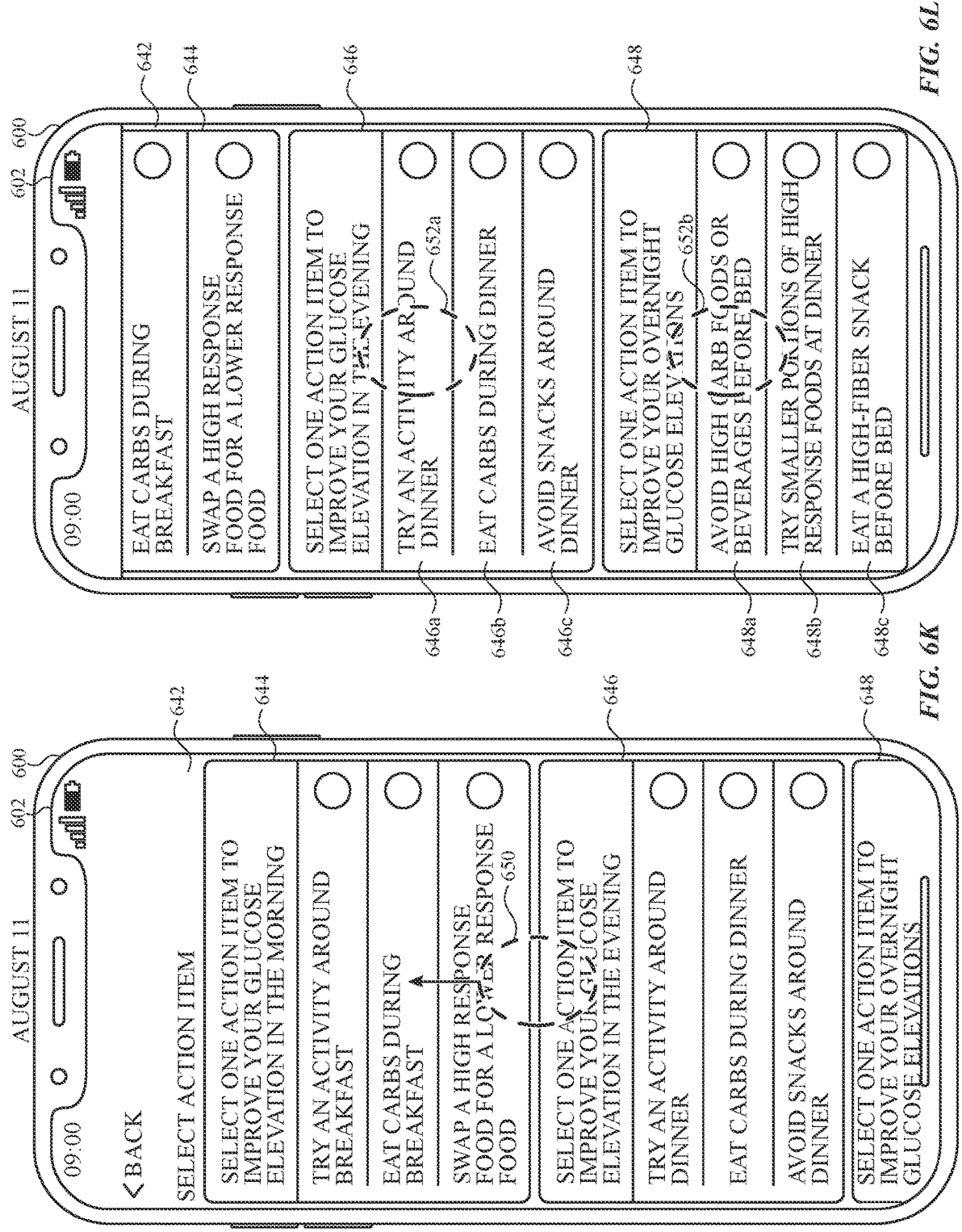

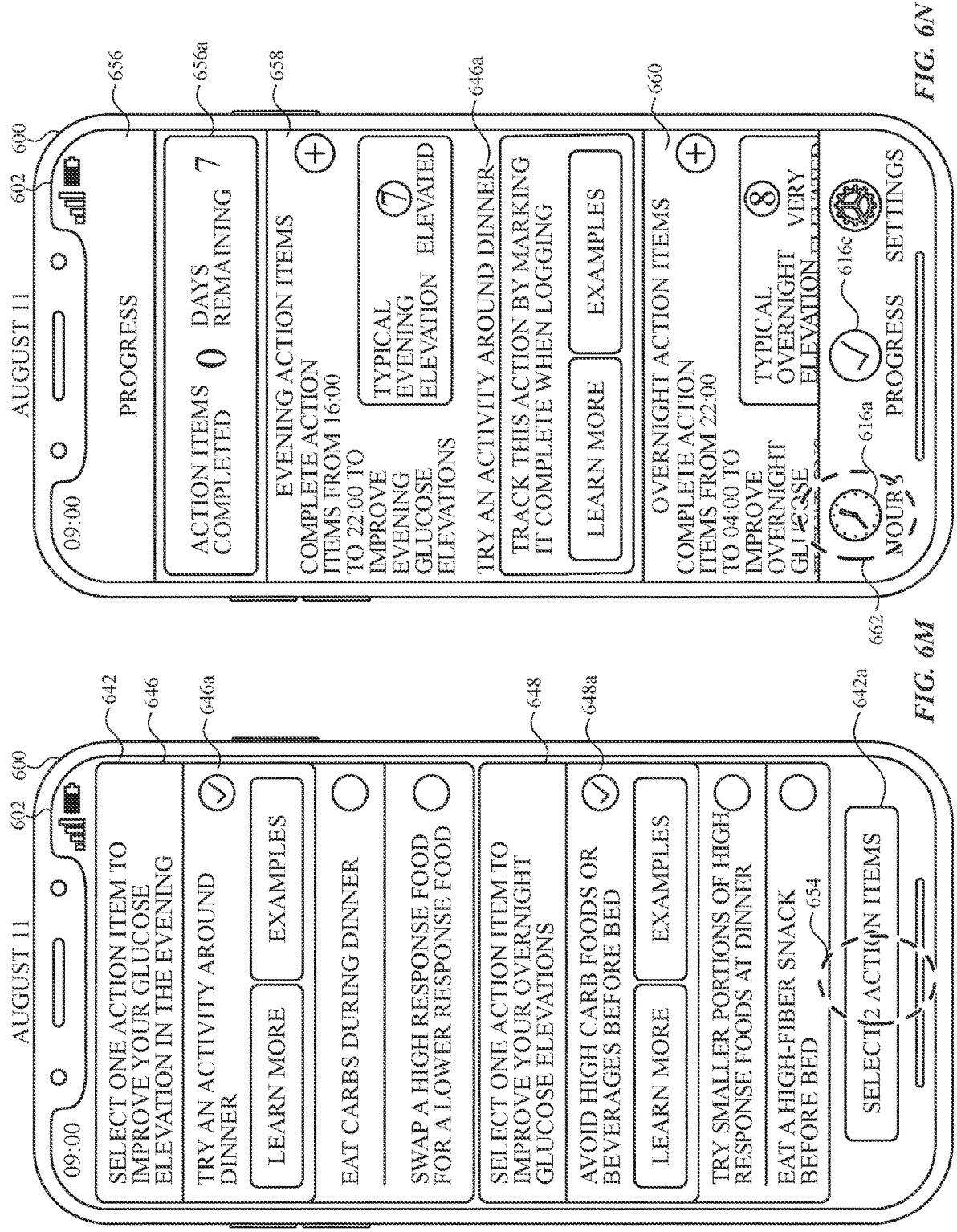

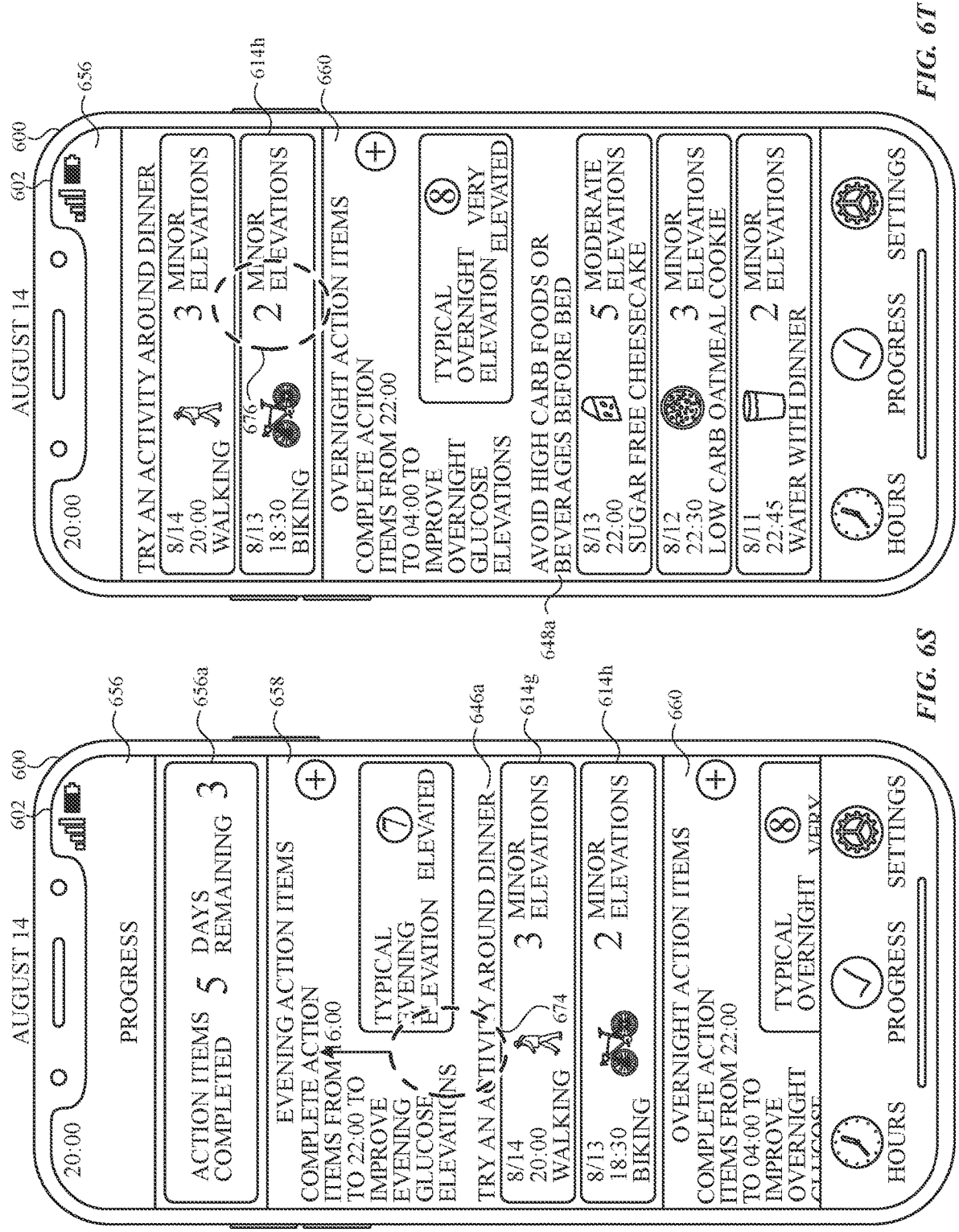

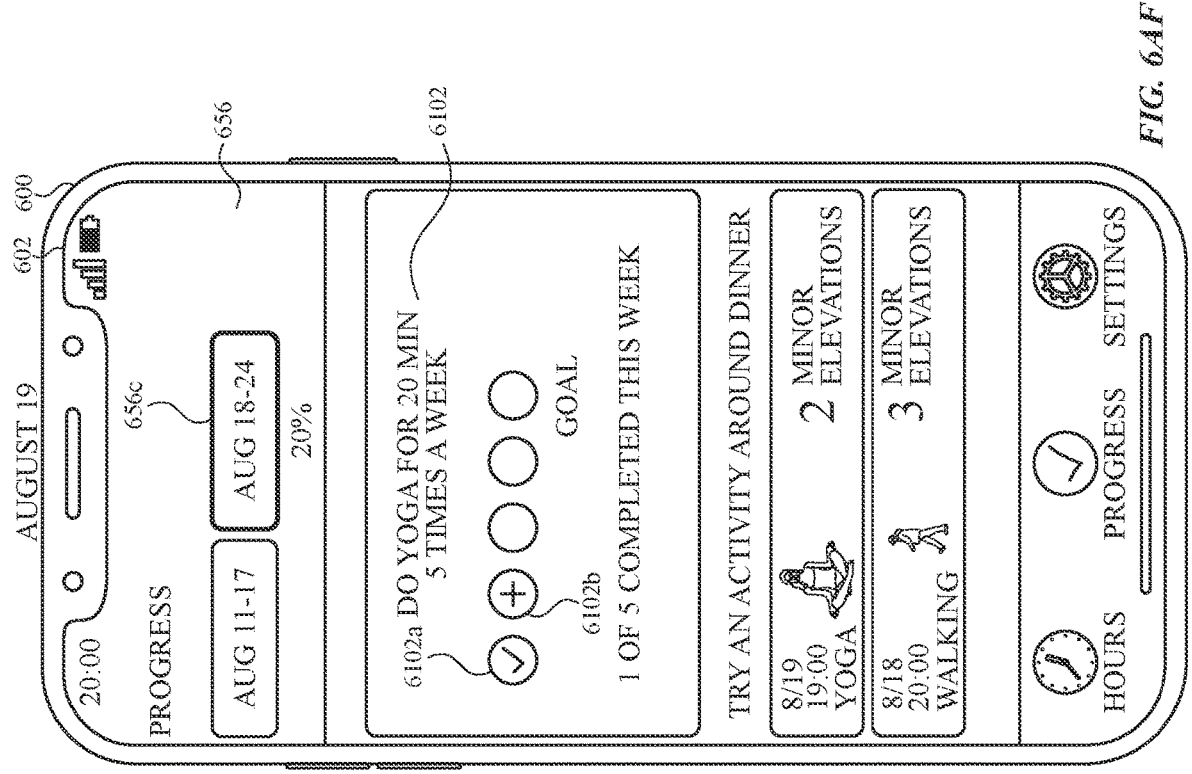
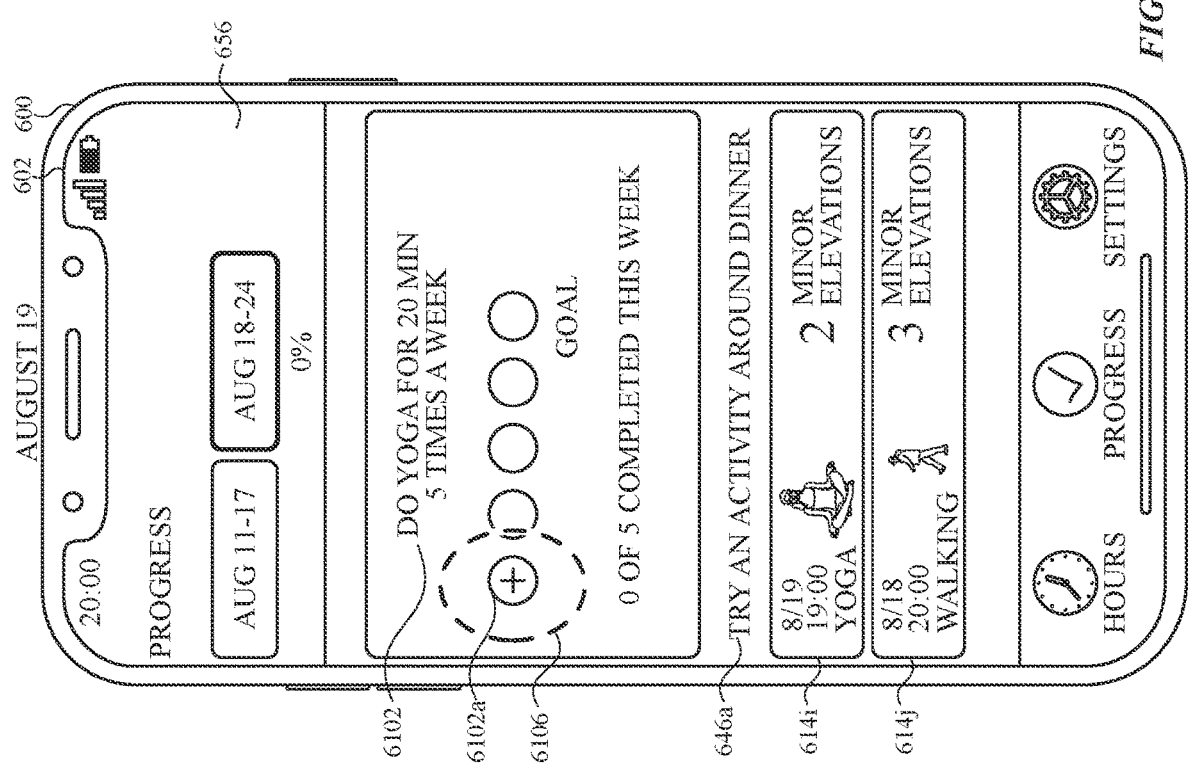
FIG. 6AE
FIG. 6AF

800 ⇘

802
Display, via the display generation component, a goal creation user interface that includes one or more selectable goal creation user interface objects that include:

804
In accordance with a determination that a first type of user activity performed for a first subset of a recurring time period meets a first set of criteria, a first selectable goal creation user interface object that corresponds to the first type of user activity to be performed during the first subset of the recurring time period.

806
In accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period.

808
Wherein the goal creation user interface includes:

810
A set of one or more selectable user interface objects that, when selected, configure a subtype of the first type of user activity.

812
A set of one or more selectable user interface objects that, when selected, configure a time period within the first subset of the recurring time period during which the first type of user activity is to be performed.

814
A set of one or more selectable user interface objects that, when selected, configure a duration for which the first type of user activity is to be performed.

816
A set of one or more selectable user interface objects that, when selected, configure a target number of times that the first type of user activity is to be performed during the first subset of the recurring time period for the predetermined duration of time.

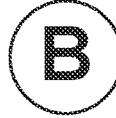

*FIG. 8A*

USER INTERFACES FOR LOGGING USER ACTIVITIES

CROSS-REFERENCE TO RELATED APPLICATIONS

This application is a continuation of U.S. patent application Ser. No. 16/953,781, filed Nov. 20, 2020, entitled "USER INTERFACES FOR LOGGING USER ACTIVITIES," which claims priority to U.S. Provisional Application Ser. No. 63/072,889, filed Aug. 31, 2020, entitled "USER INTERFACES FOR LOGGING USER ACTIVITIES," the contents of which is hereby incorporated by reference in its entirety.

FIELD

The present disclosure relates generally to computer user interfaces, and more specifically to techniques for logging user activities during a subset of a recurring time period.

BACKGROUND

Computer systems can include applications for logging user activities during a subset of a recurring time period. Such systems can receive user input using user interfaces that include one or more graphical elements adapted for use with logging user activities during a subset of a recurring time period.

BRIEF SUMMARY

Some techniques for logging user activities during a subset of a recurring time period using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for logging user activities during a subset of a recurring time period. Such methods and interfaces optionally complement or replace other methods for logging user activities during a subset of a recurring time period. Such methods and interfaces reduce the cognitive burden on a user and produce a more efficient human-machine interface. For battery-operated computing devices, such methods and interfaces conserve power and increase the time between battery charges.

In accordance with some embodiments, a method, performed at a computer system that is in communication with a display generation component and one or more input devices is described. The method includes: displaying, via the display generation component, a task selection user interface with a set of one or more selectable task user interface objects, the set of one or more selectable task user interface objects includes: in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period; while displaying the task selection user interface, receiving, via the one or more input devices, a first set of one or more inputs; and in response to the receiving the first set of one or more inputs: in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a task selection user interface with a set of one or more selectable task user interface objects, the set of one or more selectable task user interface objects includes: in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period; while displaying the task selection user interface, receiving, via the one or more input devices, a first set of one or more inputs; and in response to the receiving the first set of one or more inputs: in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a task selection user interface with a set of one or more selectable task user interface objects, the set of one or more selectable task user interface objects includes: in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period; while displaying the task selection user interface, receiving, via the one or more input devices, a first set of one or more inputs; and in response to the receiving the first set of one or more inputs: in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

In accordance with some embodiments, a computer system is described. The computer system includes: a display generation component; one or more input devices; one or more processors; and memory storing one or more programs configured to be executed by the one or more processors. The one or more programs include instructions for: displaying, via the display generation component, a task selection user interface with a set of one or more selectable task user interface objects, the set of one or more selectable task user interface objects includes: in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period; while displaying the task selection user interface, receiving, via the one or more input devices, a first set of one or more inputs; and in response to the receiving the first set of one or more inputs: in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

In accordance with some embodiments, a computer system, including a display generation component and one or more input devices is described. The computer system also includes: means for displaying, via the display generation component, a task selection user interface with a set of one or more selectable task user interface objects, the set of one or more selectable task user interface objects includes: in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period; means for, while displaying the task selection user interface, receiving, via the one or more input devices, a first set of one or more inputs; and means for, in response to the receiving the first set of one or more inputs: in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

In accordance with some embodiments, a method, performed at a computer system that is in communication with a display generation component and one or more input devices is described. The method includes: displaying, via the display generation component, a goal creation user interface with a set of one or more selectable goal creation user interface objects, the set of one or more selectable goal creation user interface objects includes: in accordance with a determination that a first type of user activity performed for a first subset of a recurring time period meets a first set of criteria, a first selectable goal creation user interface object that corresponds to the first type of user activity to be performed during the first subset of the recurring time period; and in accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period; while displaying the goal creation user interface, receiving a first set of one or more inputs; and in response to the receiving the first set of one or more inputs: in accordance with a determination that the first set of one or more inputs includes an input selecting the first selectable goal creation user interface object, enabling logging of the first type of user activity during the first subset of the recurring time period for a predetermined duration of time; and in accordance with a determination that the first set of one or more inputs includes an input selecting the second selectable goal creation user interface object, enabling logging of the second type of user activity during the second subset of the recurring time period for the predetermined duration of time.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a goal creation user interface with a set of one or more selectable goal creation user interface objects, the set of one or more selectable goal creation user interface objects includes: in accordance with a determination that a first type of user activity performed for a first subset of a recurring time period meets a first set of criteria, a first selectable goal creation user interface object that corresponds to the first type of user activity to be performed during the first subset of the recurring time period; and in accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period; while displaying the goal creation user interface, receiving a first set of one or more inputs; and in response to the receiving the first set of one or more inputs: in accordance with a determination that the first set of one or more inputs includes an input selecting the first selectable goal creation user interface object, enabling logging of the first type of user activity during the first subset of the recurring time period for a predetermined duration of time; and in accordance with a determination that the first set of one or more inputs includes an input selecting the second selectable goal creation user interface object, enabling logging of the second type of user activity during the second subset of the recurring time period for the predetermined duration of time.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a goal creation user interface with a set of one or more selectable goal creation user interface objects, the set of one or more selectable goal creation user interface objects includes: in accordance with a determination that a first type of user activity performed for a first subset of a recurring time period meets a first set of criteria, a first selectable goal creation user interface object that corresponds to the first type of user activity to be performed during the first subset of the recurring time period; and in accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period; while displaying the goal creation user interface, receiving a first set of one or more inputs; and in response to the receiving the first set of one or more inputs: in accordance with a determination that the first set of one or more inputs includes an input selecting the first selectable goal creation user interface object, enabling logging of the first type of user activity during the first subset of the recurring time period for a predetermined duration of time; and in accordance with a determination that the first set of one or more inputs includes an input selecting the second selectable goal creation user interface object, enabling logging of the second type of user activity during the second subset of the recurring time period for the predetermined duration of time.

In accordance with some embodiments, a computer system is described. The computer system includes: a display generation component; one or more input devices; one or more processors; and memory storing one or more programs configured to be executed by the one or more processors. The one or more programs include instructions for: displaying, via the display generation component, a goal creation user interface with a set of one or more selectable goal creation user interface objects, the set of one or more selectable goal creation user interface objects includes: in accordance with a determination that a first type of user activity performed for a first subset of a recurring time period meets a first set of criteria, a first selectable goal creation user interface object that corresponds to the first type of user activity to be performed during the first subset of the recurring time period; and in accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period; while displaying the goal creation user interface, receiving a first set of one or more inputs; and in response to the receiving the first set of one or more inputs: in accordance with a determination that the first set of one or more inputs includes an input selecting the first selectable goal creation user interface object, enabling logging of the first type of user activity during the first subset of the recurring time period for a predetermined duration of time; and in accordance with a determination that the first set of one or more inputs includes an input selecting the second selectable goal creation user interface object, enabling logging of the second type of user activity during the second subset of the recurring time period for the predetermined duration of time.

In accordance with some embodiments, a computer system including a display generation component and one or more input devices is described. The computer system also includes: means for displaying, via the display generation component, a goal creation user interface with a set of one or more selectable goal creation user interface objects, the set of one or more selectable goal creation user interface objects includes: in accordance with a determination that a first type of user activity performed for a first subset of a recurring time period meets a first set of criteria, a first selectable goal creation user interface object that corresponds to the first type of user activity to be performed during the first subset of the recurring time period; and in accordance with a determination that a second type of user activity performed for a second subset of a recurring time period, different from the first subset of the recurring time period, meets a first set of criteria, a second selectable goal creation user interface object that corresponds to the second type of user activity to be performed during the second subset of the recurring time period; means for, while displaying the goal creation user interface, receiving a first set of one or more inputs; and means for, in response to the receiving the first set of one or more inputs: in accordance with a determination that the first set of one or more inputs includes an input selecting the first selectable goal creation user interface object, enabling logging of the first type of user activity during the first subset of the recurring time period for a predetermined duration of time; and in accordance with a determination that the first set of one or more inputs includes an input selecting the second selectable goal creation user interface object, enabling logging of the second type of user activity during the second subset of the recurring time period for the predetermined duration of time.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for logging user activities during a subset of a recurring time period, thereby increasing the effectiveness, efficiency, and user satisfaction with such devices. Such methods and interfaces may complement or replace other methods for logging user activities during a subset of a recurring time period.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 8A-8B are a flow diagram illustrating a method for logging user activities during a subset of a recurring time period, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for logging user activities during a subset of a recurring time period. Further, electronic devices should provide displays of logged user activities during a subset of a recurring time period along with other user data in order for a user to determine the effects of performing user activities. Such techniques can reduce the cognitive burden on a user who log user activities during a subset of a recurring time period, thereby enhancing productivity. Further, such techniques can reduce processor and battery power otherwise wasted on redundant user inputs.

Figure 6A:
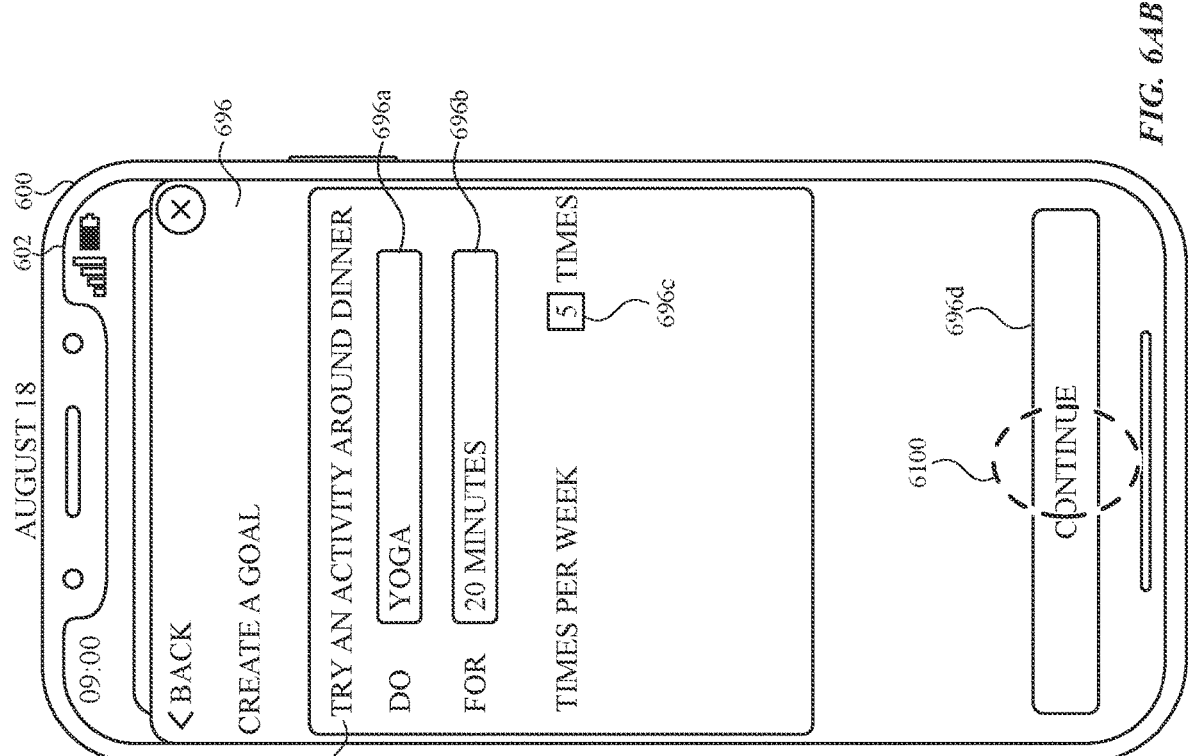
Figure 6A:
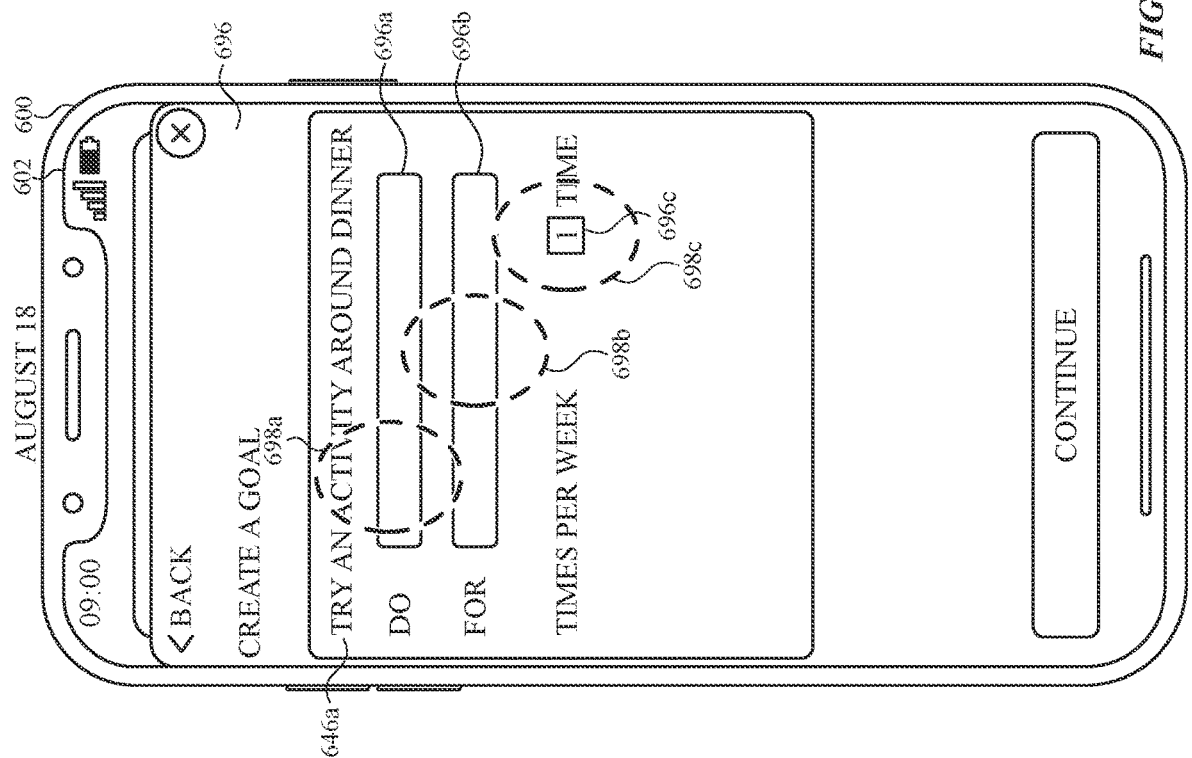
Figure 6A:
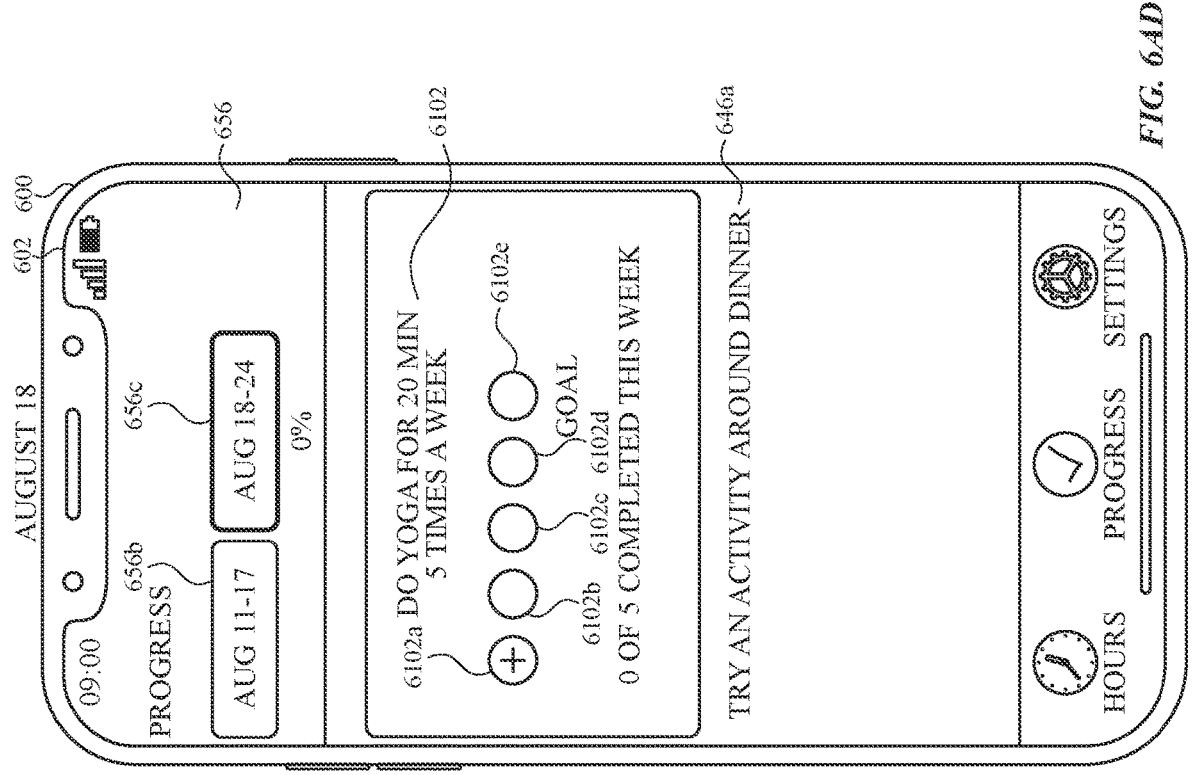
Figure 6A:
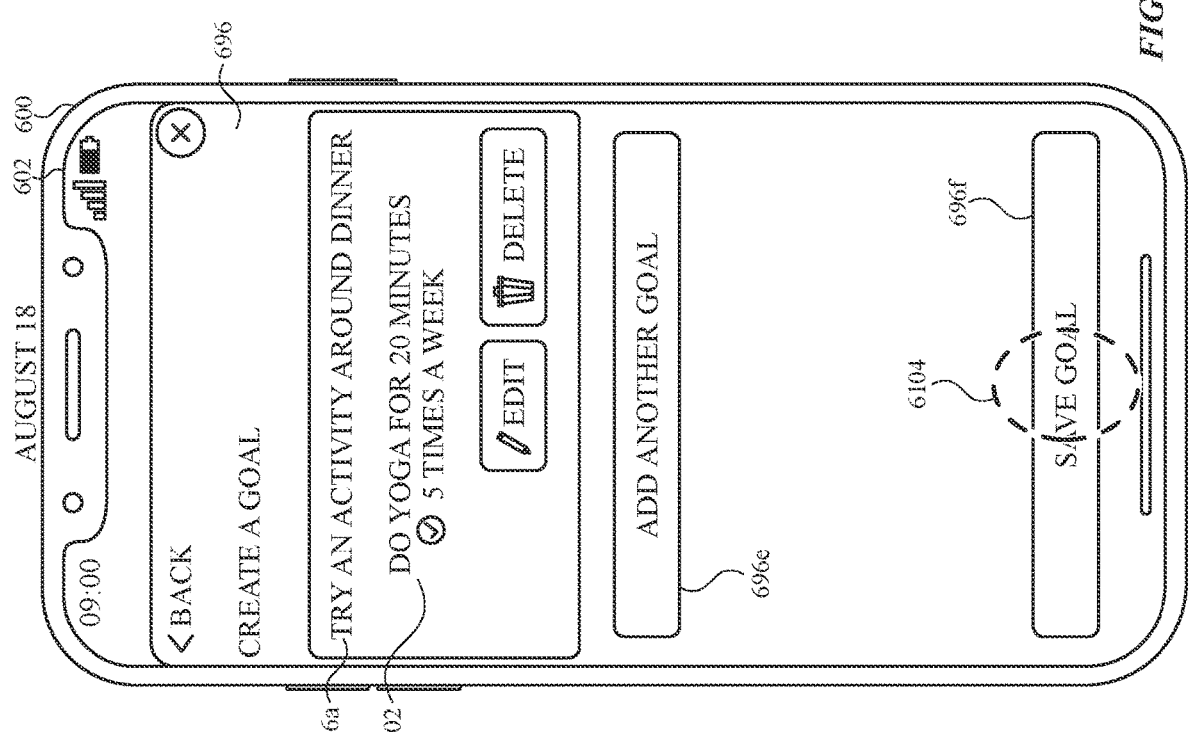
Figure 6A:
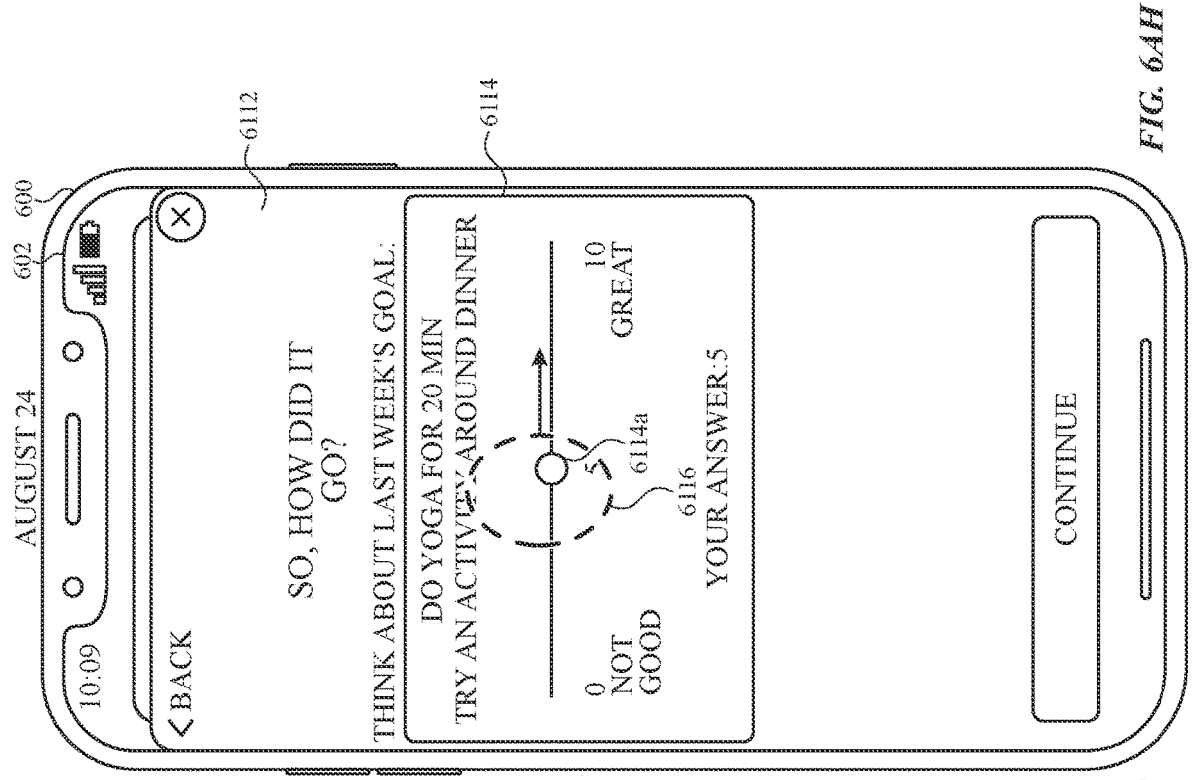
Figure 6A:
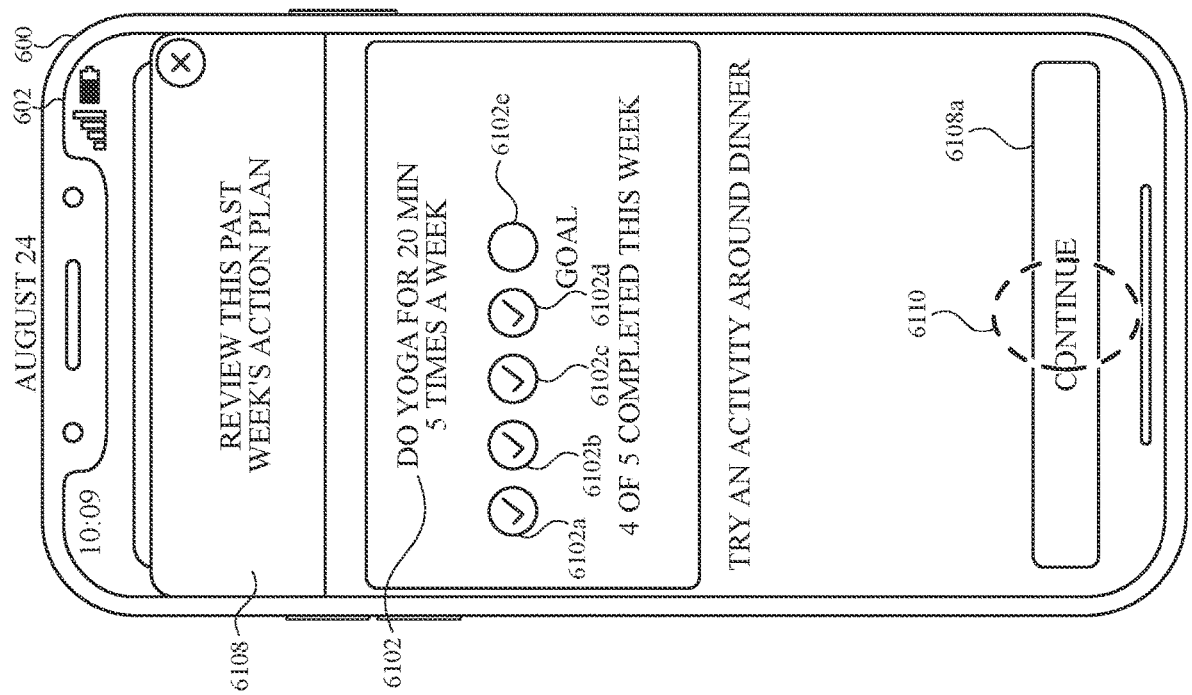
Figure 6A:
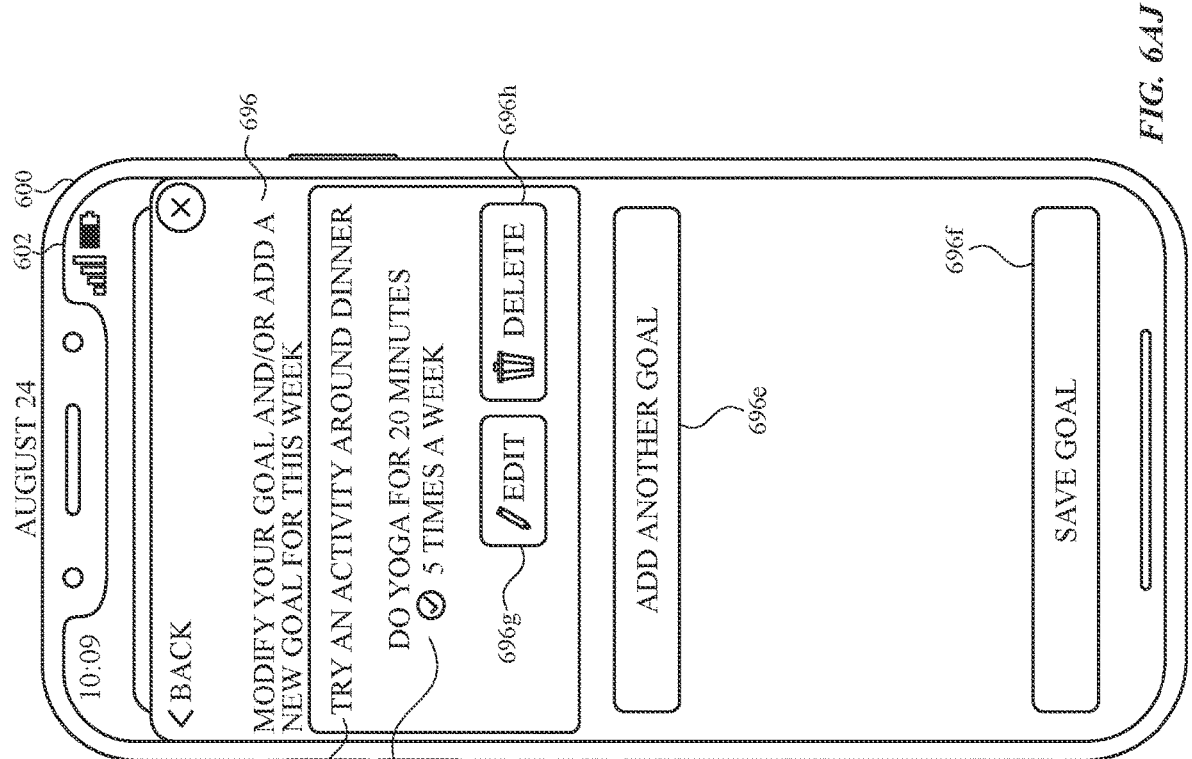
Figure 6A:
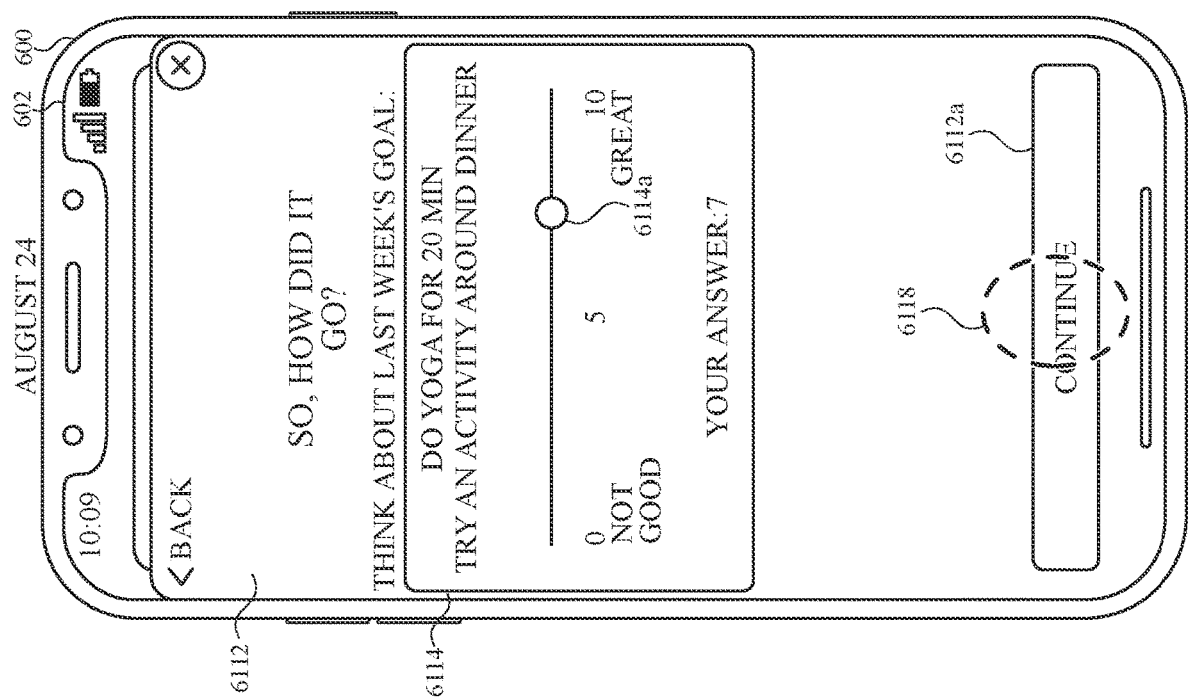
Figure 6A:
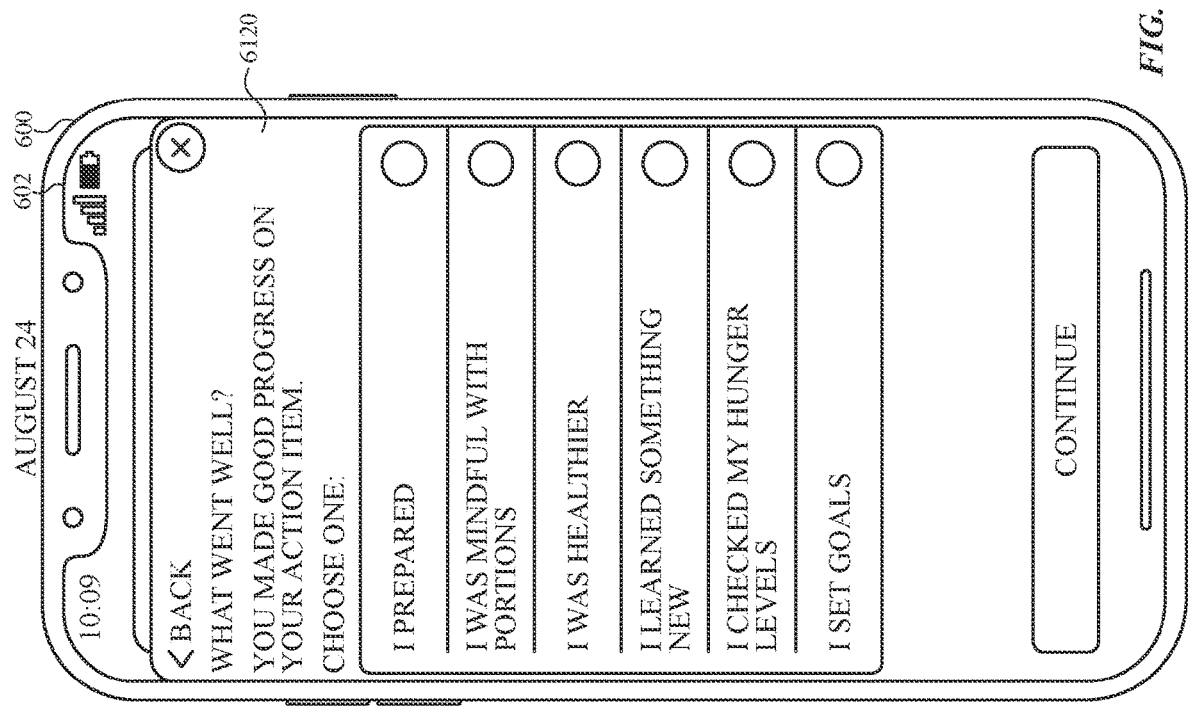
Figure 6A:
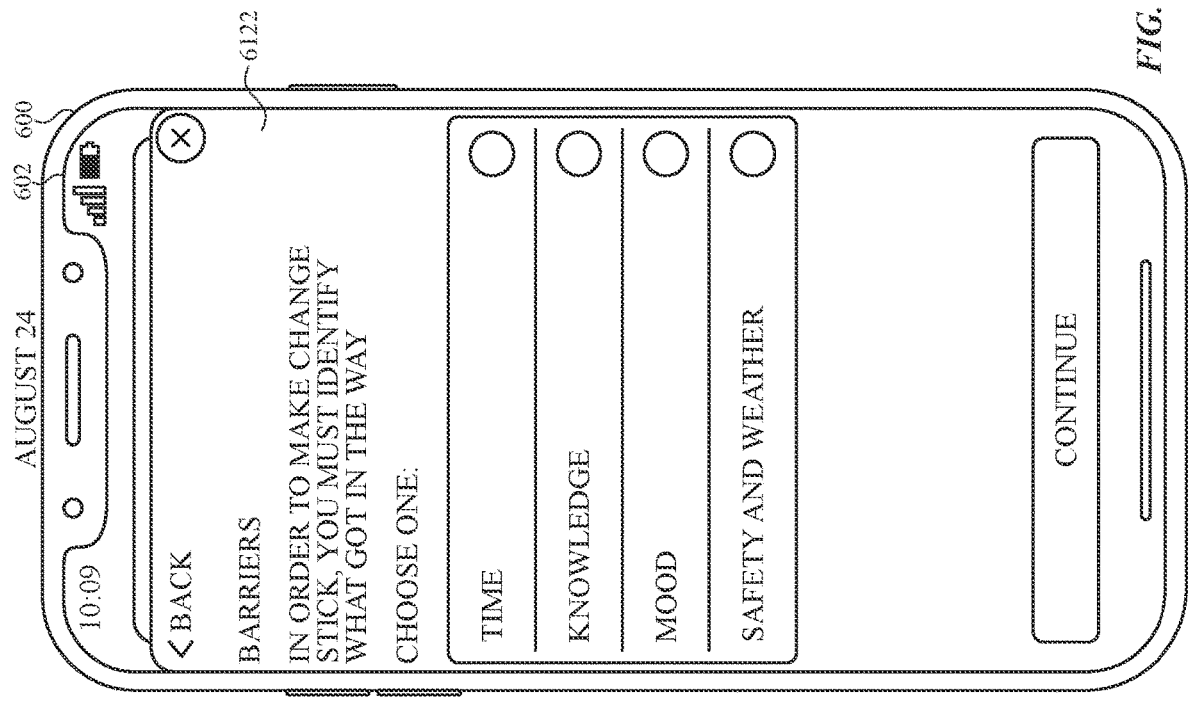
Figure 7:
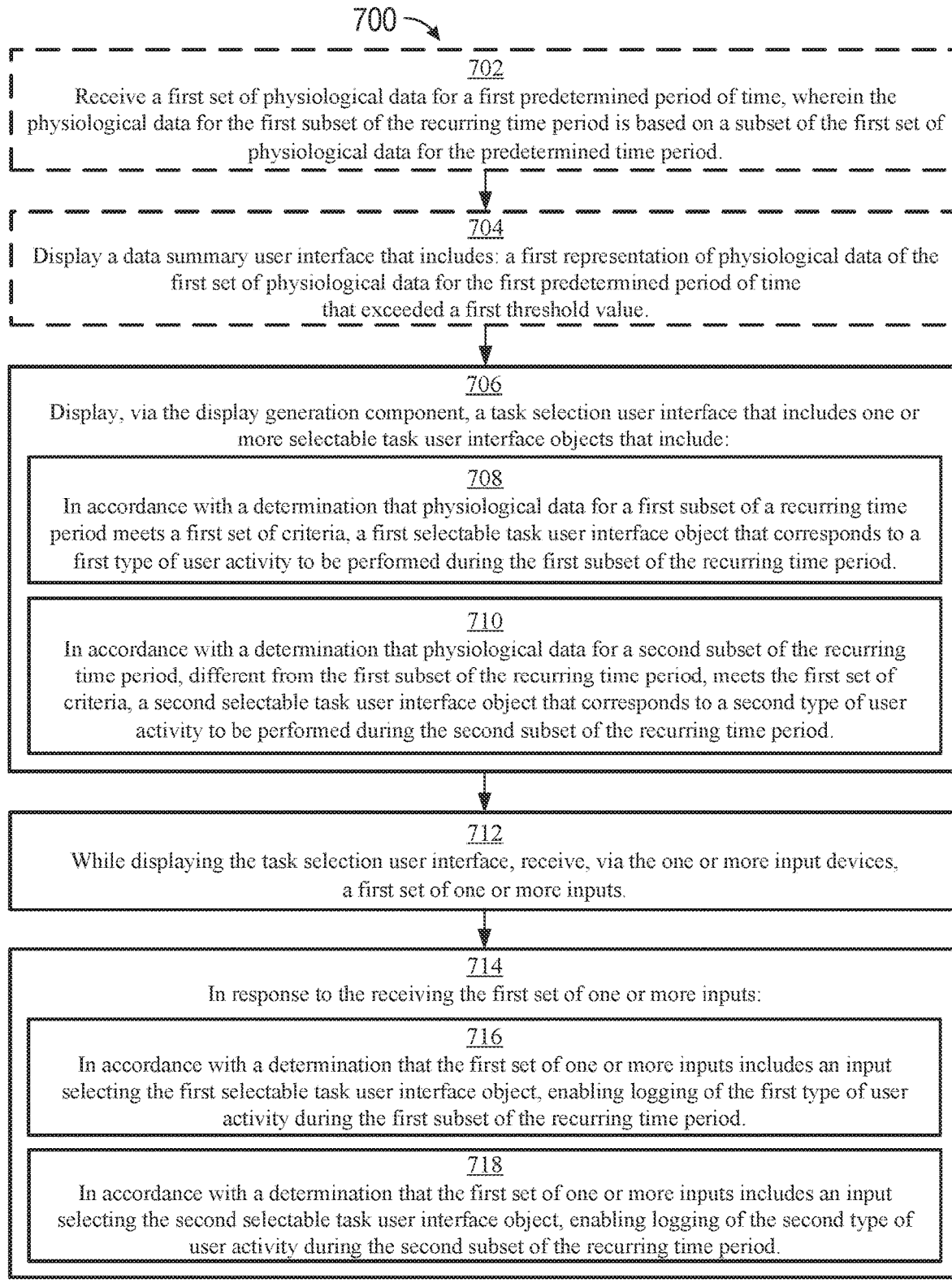
FIG. 7 is a flow diagram illustrating a method for logging user activities during a subset of a recurring time period, in accordance with some embodiments.
Figure 8B:
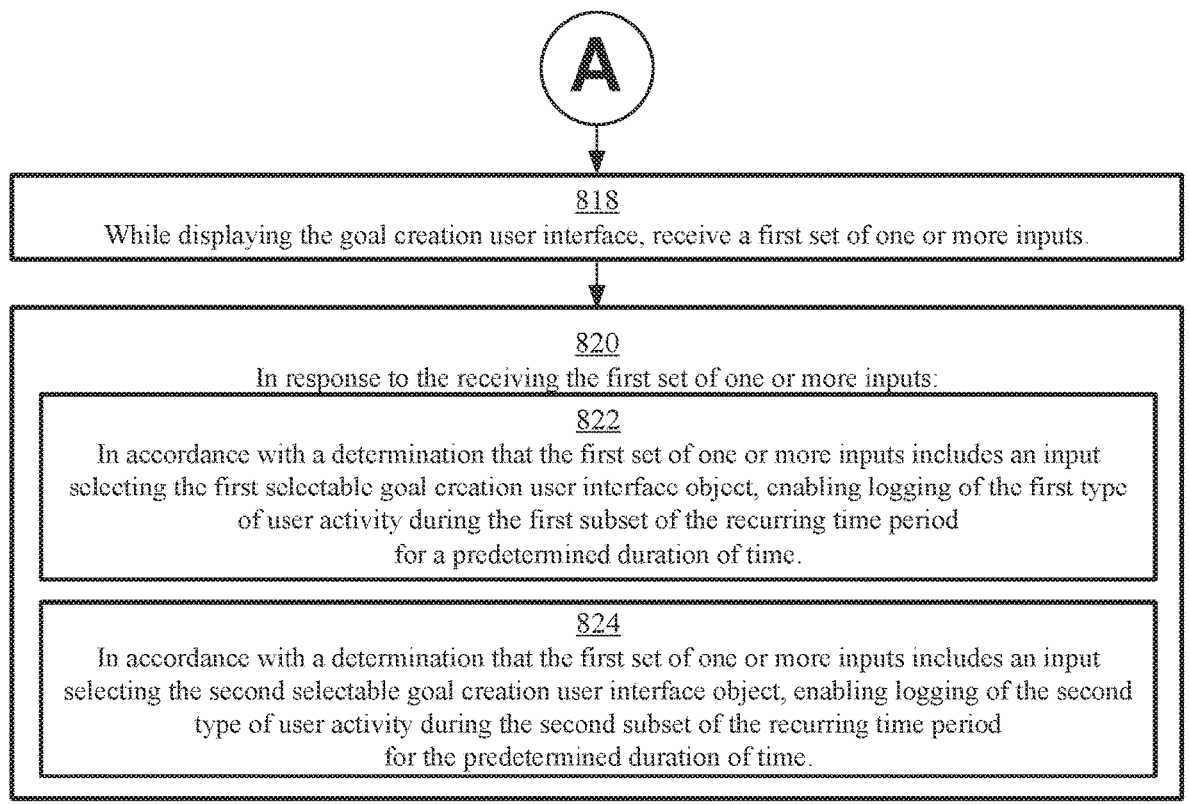

Below, FIGS. 1A-1B, 2, 3, 4A-4B, and 5A-5B provide a description of exemplary devices for performing the techniques for managing event notifications. FIGS. 6A-6AL illustrate exemplary user interfaces logging user activities during a subset of a recurring time period. FIG. 7 is a flow diagram illustrating methods of logging user activities during a subset of a recurring time period, in accordance with some embodiments. FIGS. 8A-8B are a flow diagram illustrating methods of logging user activities during a subset of a recurring time period, in accordance with some embodiments. The user interfaces in FIGS. 6A-6AL are used to illustrate the processes described below, including the processes in FIG. 7 and FIGS. 8A-8B.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
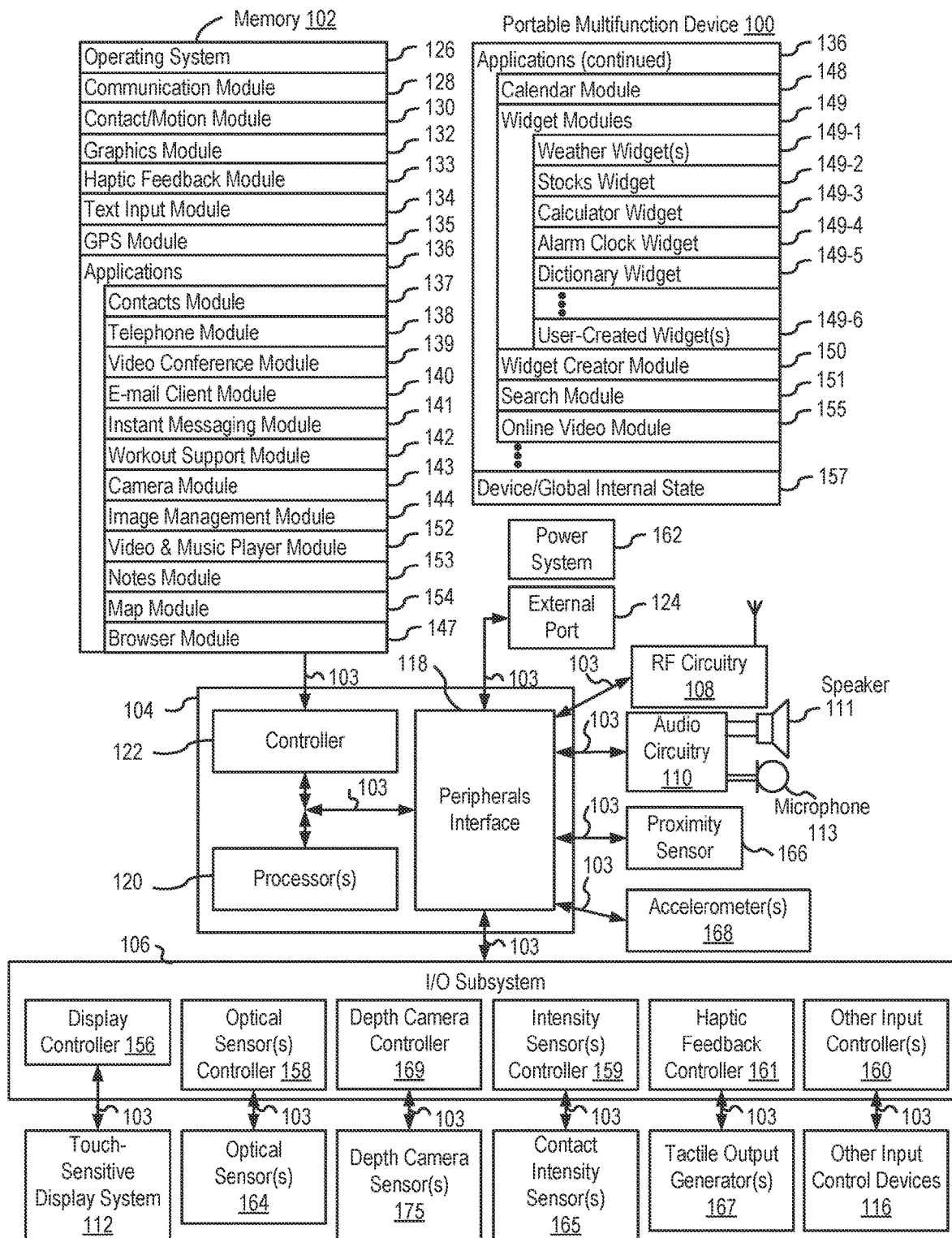
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user.

Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
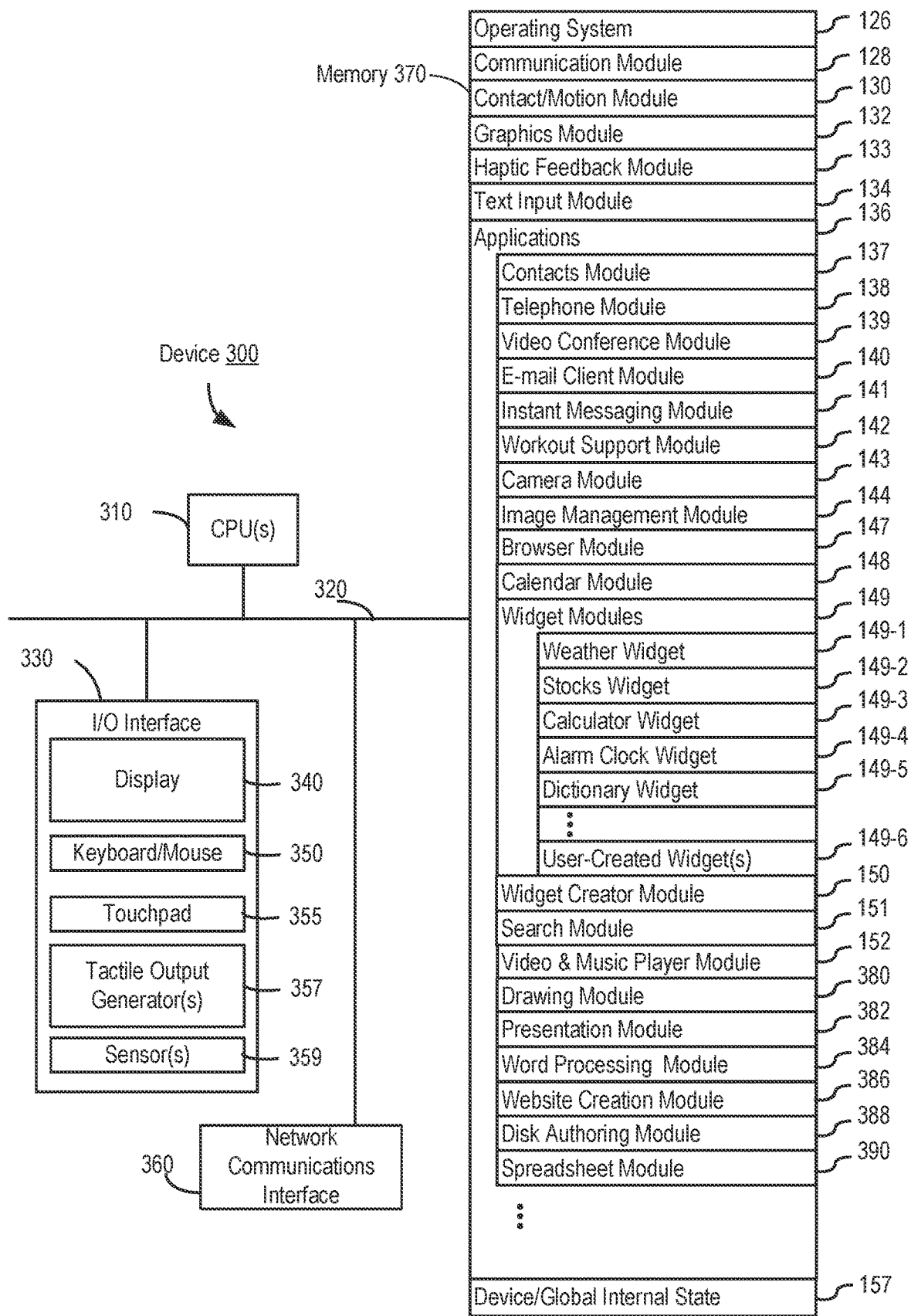
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are, optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
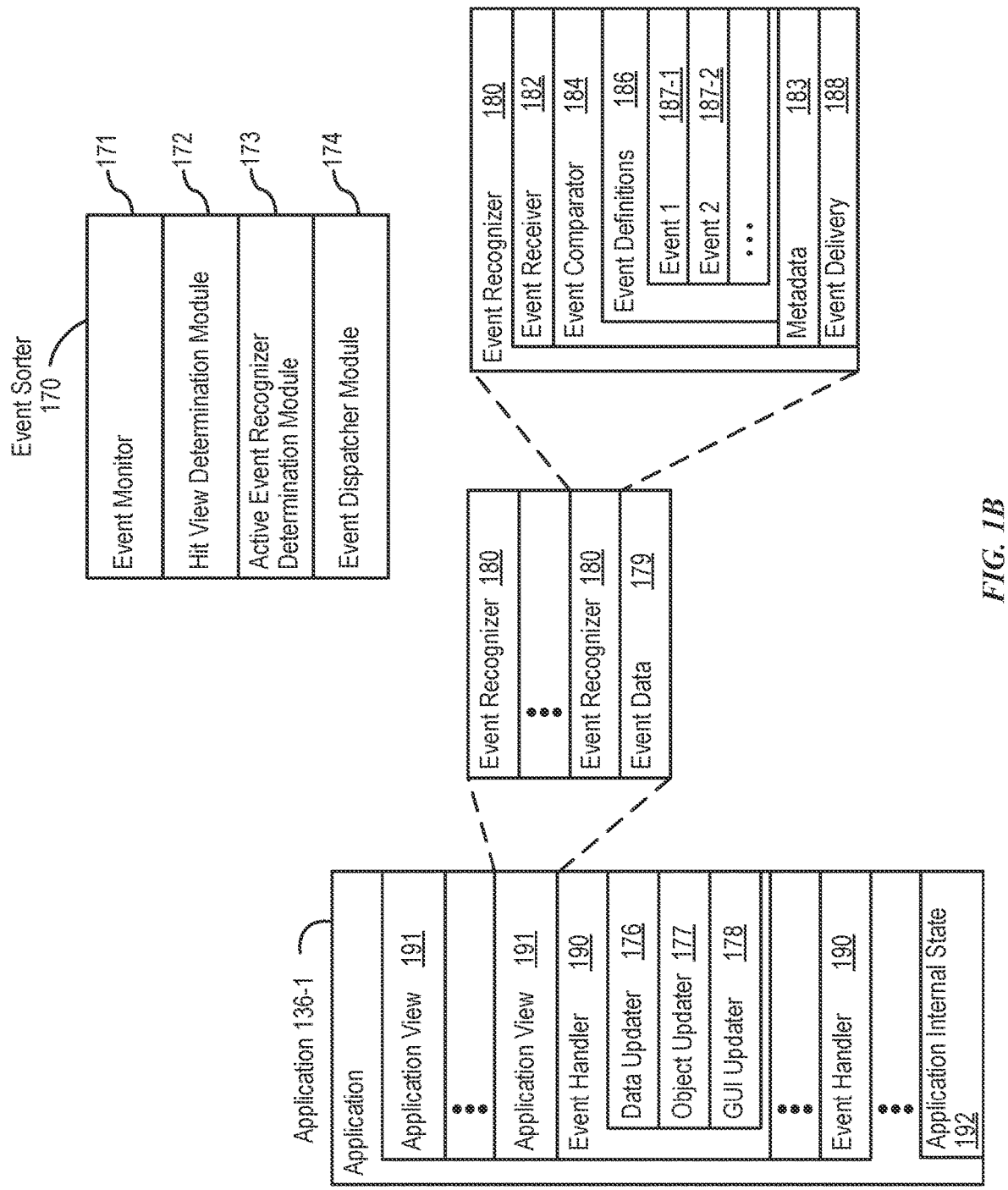
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
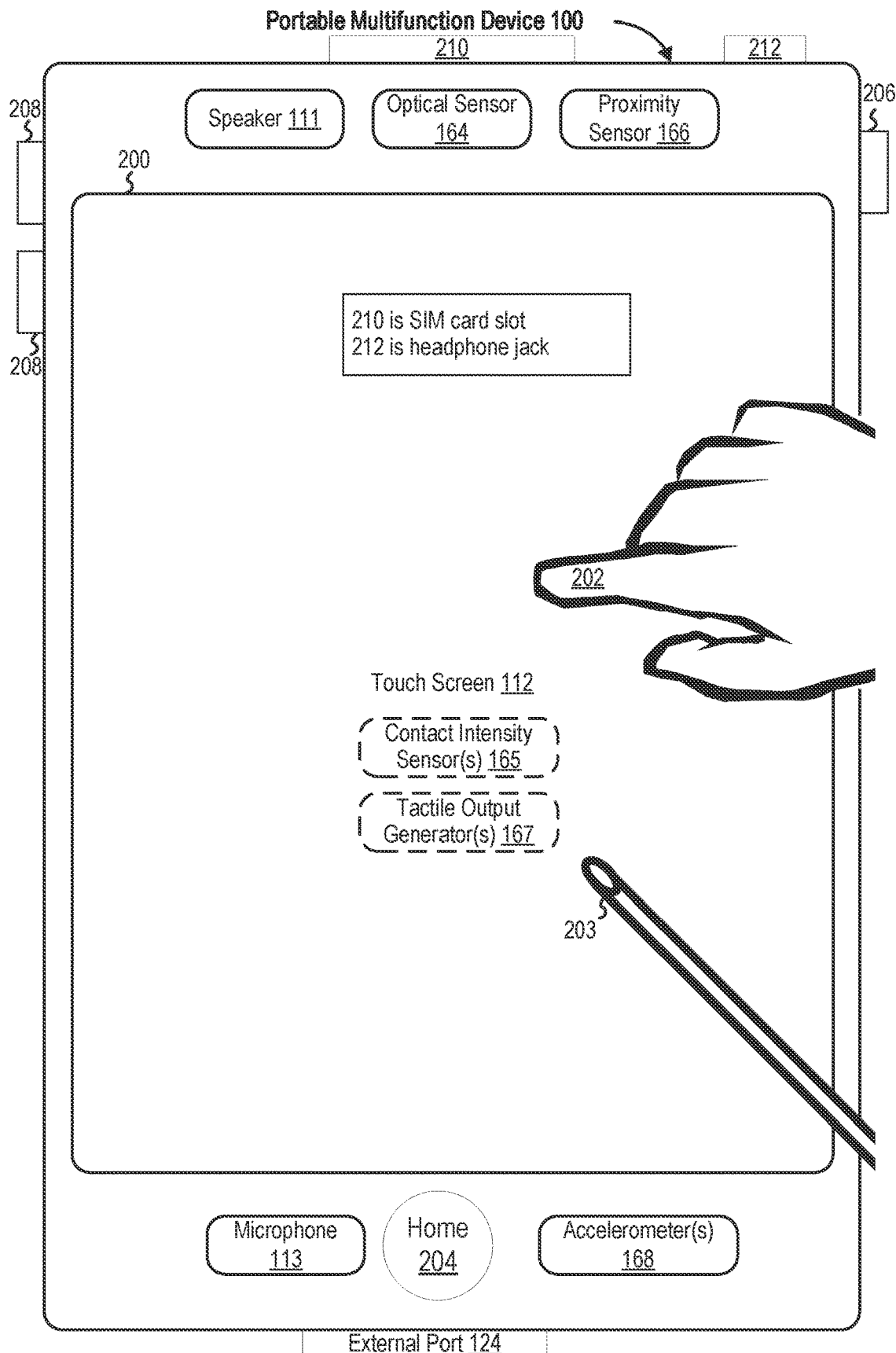
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
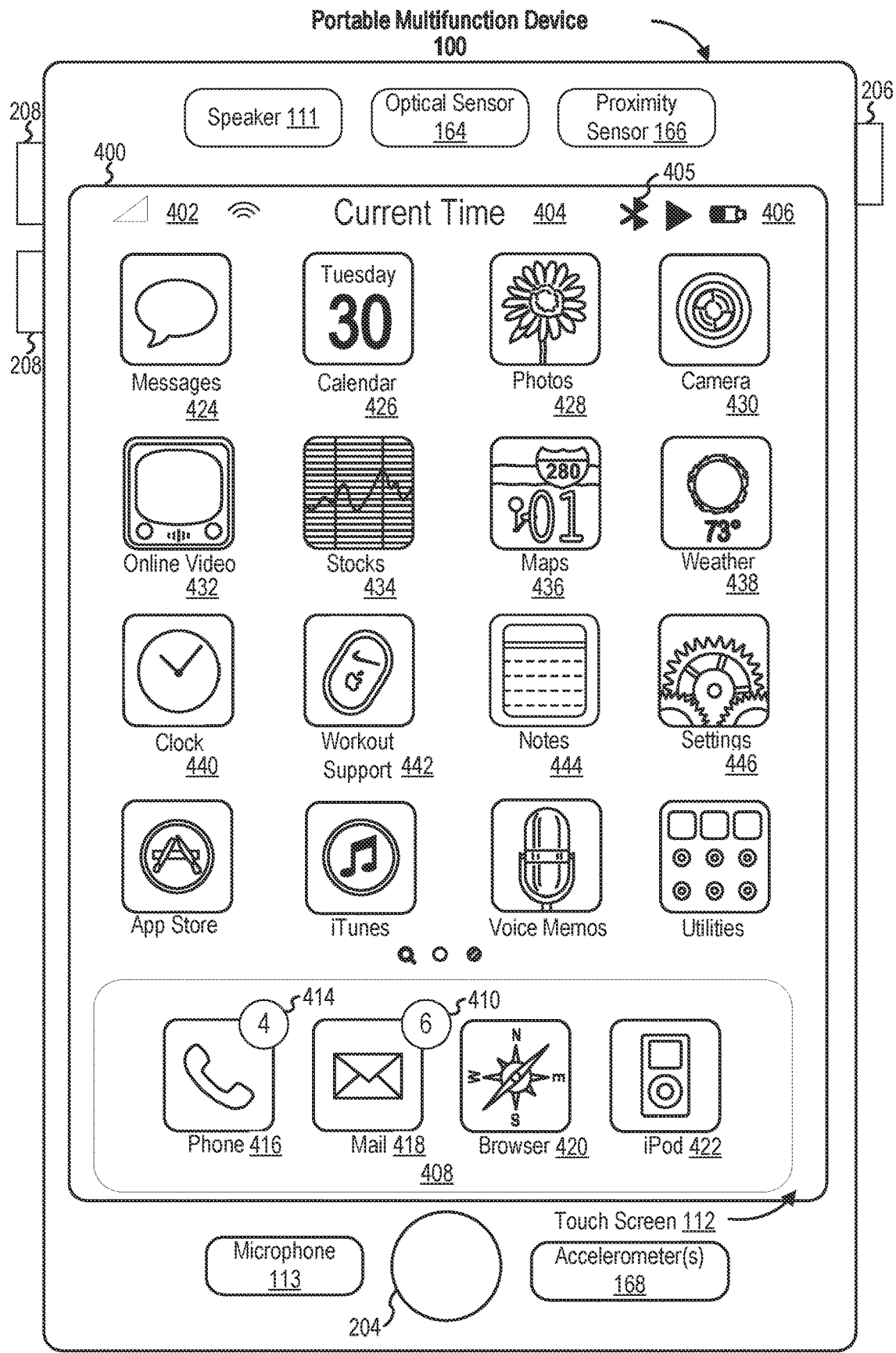
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
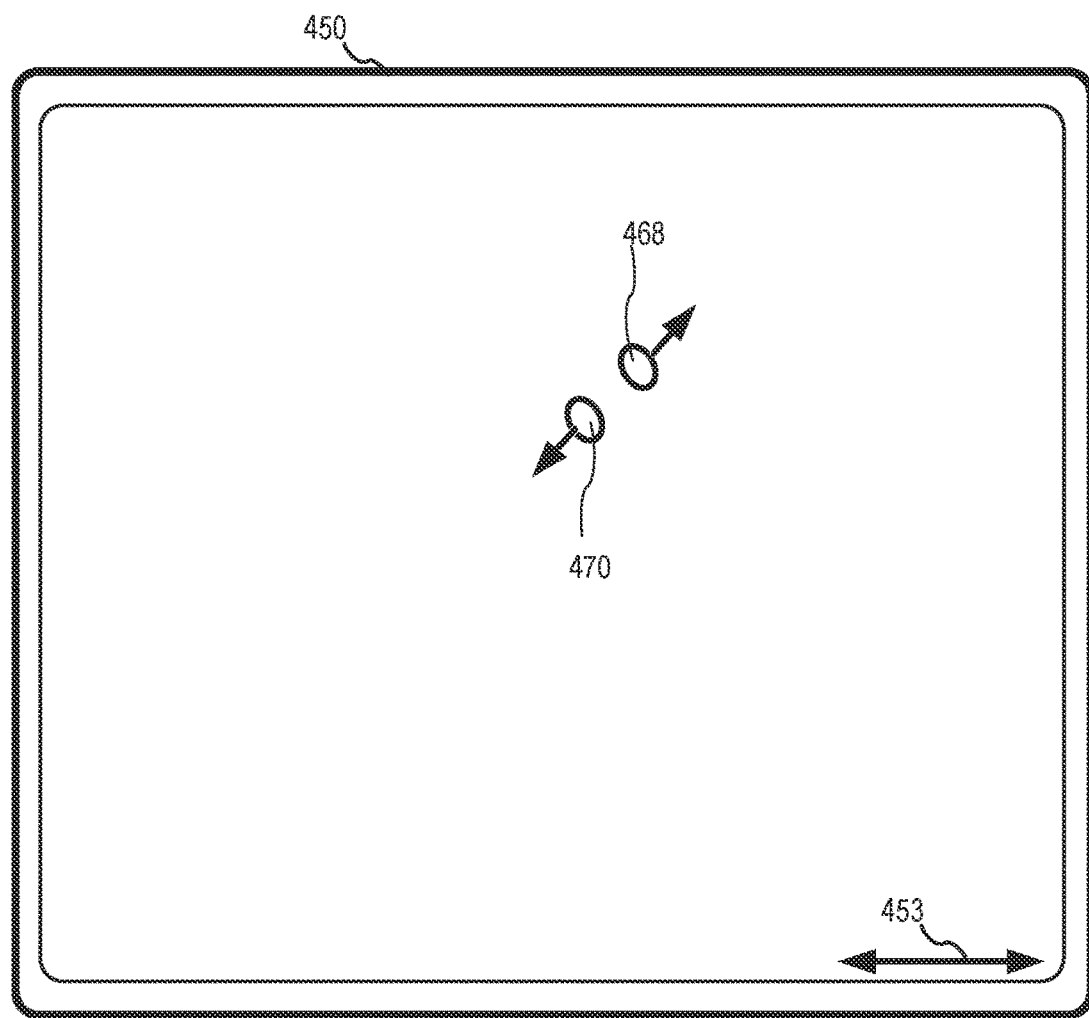
FIG. 4B illustrates an exemplary user interface for a multifunction device with a touch-sensitive surface that is separate from the display in accordance with some embodiments.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 4B:
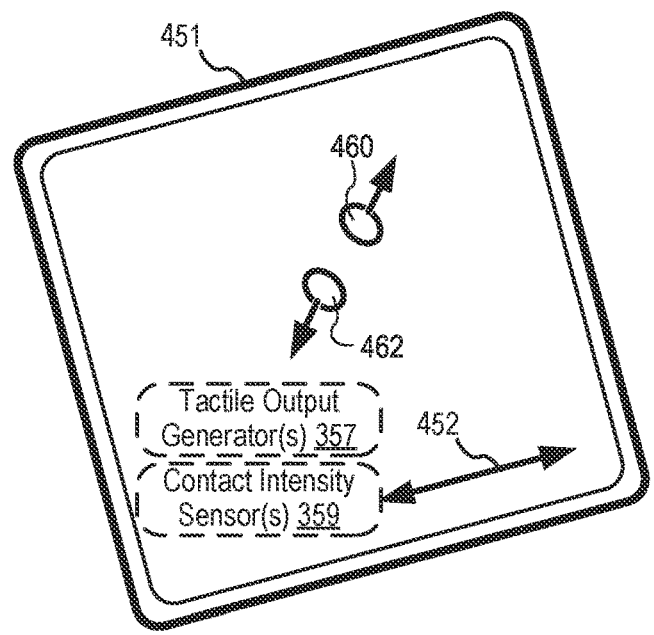
Figure 5A:
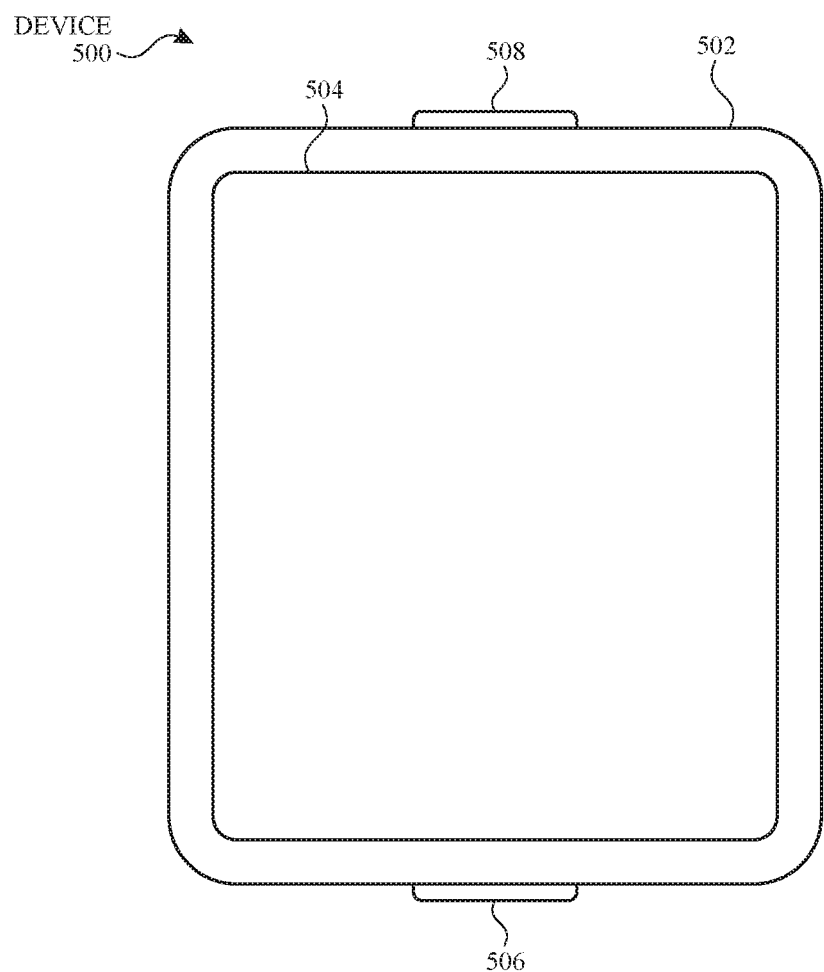
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
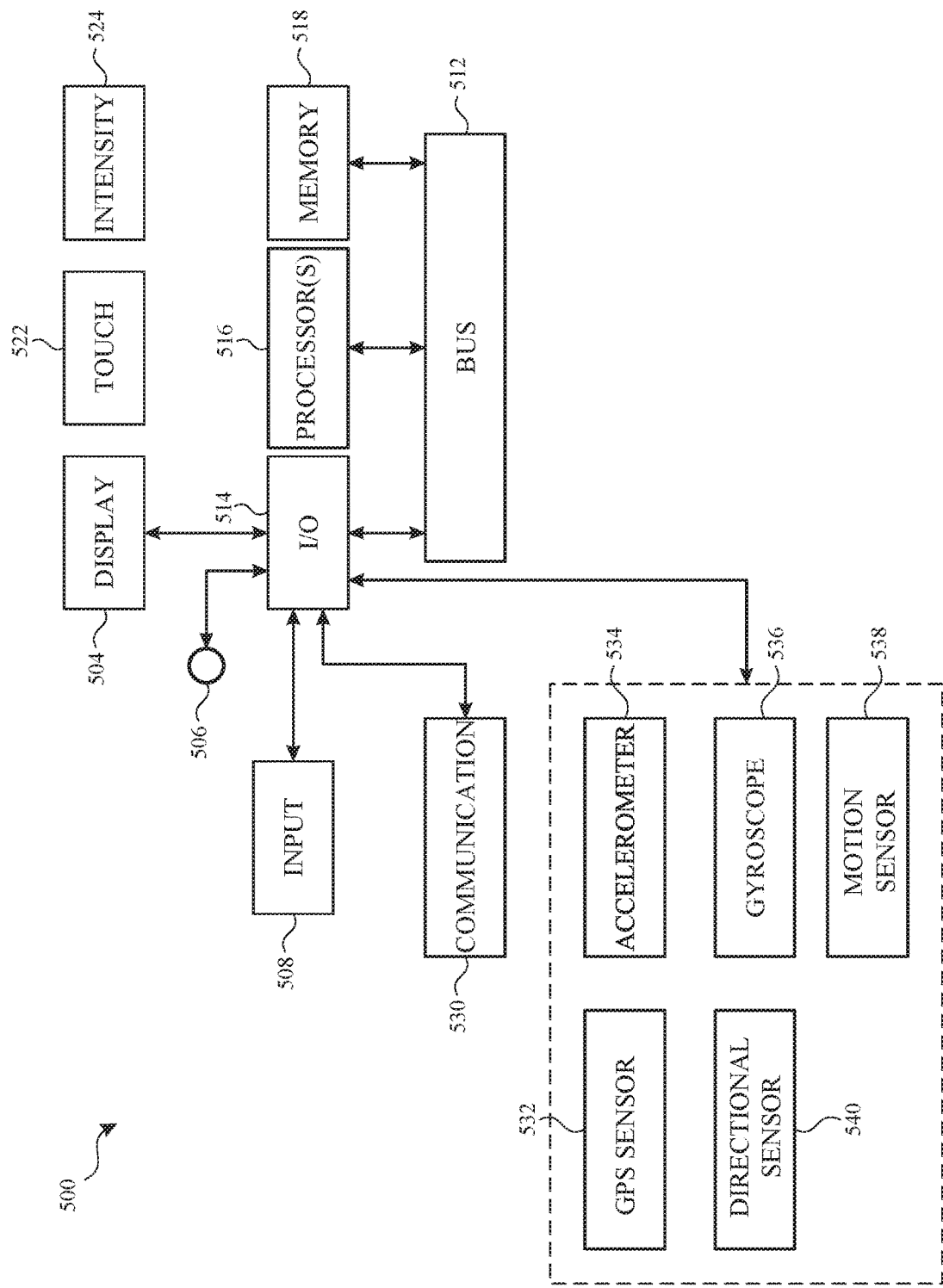
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700-800 (FIGS. 7, 8A-8B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6AL illustrate exemplary user interfaces for logging user activities during a subset of a recurring time period, in accordance with some embodiments. The user interfaces in these figures are used to illustrate the processes described below, including the processes in FIGS. 7 and 8A-8B.

FIG. 6A illustrates electronic device 600 (e.g., a smart phone) displaying introductory user interface 606 on touchscreen display 602. In some embodiments, device 600 includes one or more features of devices 100, 300, and/or 500. The current date is August 1, as indicated by the text (which is provided to improve understanding and is not part of the displayed interface) above device 600, and the current time is 08:00, as shown by time indication 604. Introductory user interface 606 introduces the glucose monitoring feature and includes continue affordance 606a. In some embodiments, introductory user interface 606 includes multiple, separate screens of content that describe the glucose monitoring feature in greater detail during onboarding. In some embodiments, device 600 receives one or more inputs to initiate and complete onboarding for the glucose monitoring feature. In this example, device 600 detects tap input 608 corresponding to selection of continue affordance 606a and, in response to receiving tap input 608, device 600 starts the baseline phase (e.g., an onboarding phase, initial phase, and/or sensor phase) and displays hourly log user interface 610, as shown in FIG. 6B.

FIG. 6B depicts device 600 displaying, on touchscreen display 602, hourly log user interface 610. Hourly log user interface 610 includes graph region 612, which includes day of the week indicators 612a (e.g., "S" for Sunday, "M" for Monday, and so forth) and chart region 612b, which currently reads "NO CHART DATA AVAILABLE." In some embodiments, once enough data has been received, day of the week indicators 612a can be selected, causing device 600 to display chart data for the selected day. In some embodiments, chart data becomes available after a predetermined amount of data (e.g., blood glucose data) has been received by device 600. In some embodiments, the blood glucose data is provided by a continuous blood glucose monitor, worn by a user of device 600, that is in communication with device 600.

Hourly log user interface 610 further includes log region 614. Log region 614 includes meal logging affordance 614a, activity logging affordance 614b, and mood logging affordance 614c. Hourly log user interface 610 also includes hours tab affordance 616a and settings tab affordance 616b. In some embodiments, selection of setting tab affordance 616b causes device 600 to display a settings user interface. In some embodiments, the settings user interface includes a variety of options, some of which could be reviewing collected data, adjusting time frames, viewing policies, customizing measurement units.

Figure 6D:
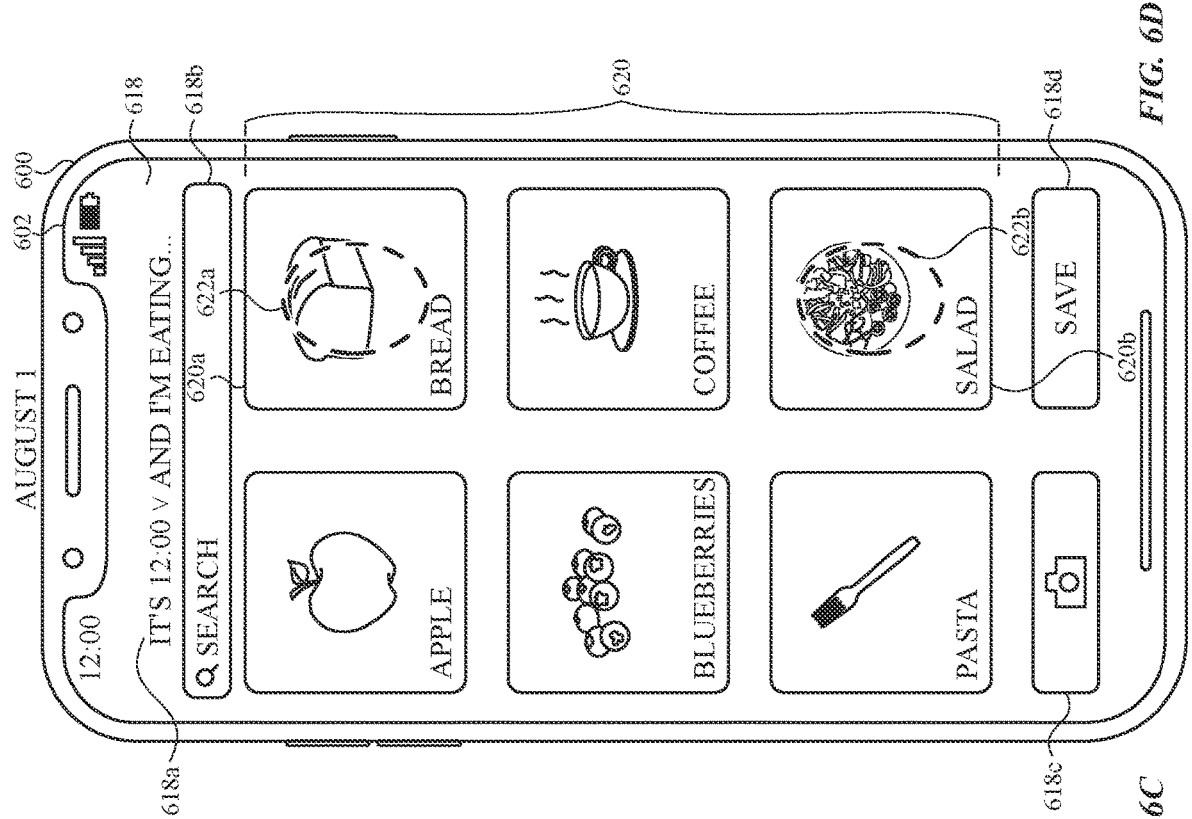
FIGS. 6A-6AL illustrate exemplary user interfaces for logging user activities during a subset of a recurring time period, in accordance with some embodiments.
Figure 6C:
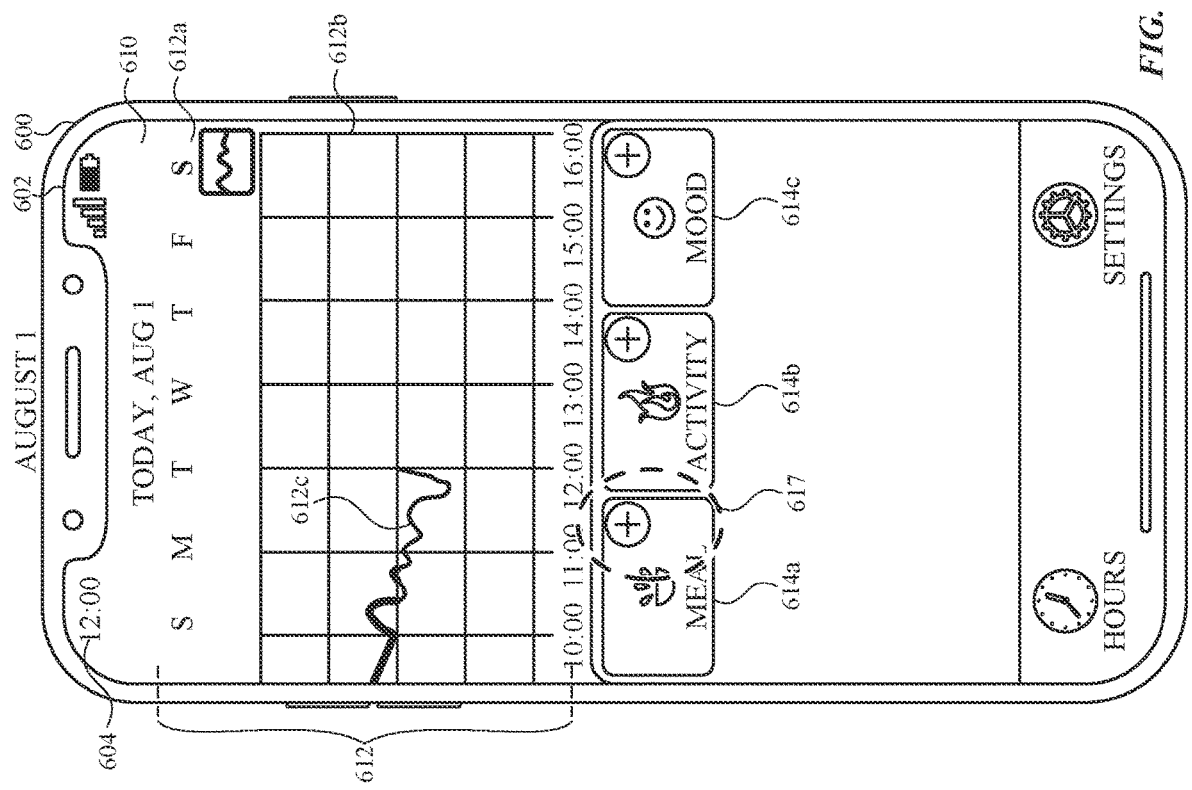

As shown by time indication 604 in FIG. 6C, 4 hours have passed (relative to FIG. 6B) and the current time is now 12:00. Device 600 has received blood glucose data to be displayed on touchscreen display 602 within hourly log user interface 610. The day of the week indicator 612a corresponding to Saturday, August 1 (e.g., "S") now includes a small chart icon indicating that data has been collected for the day. Chart region 612b now includes hours along the x-axis and blood glucose amount along the y-axis. Chart line 612c (e.g., corresponding to blood glucose measurements) shows the measurements of blood glucose at particular time periods. Chart line 612c stops at 12:00, indicating that data has been collected prior to 12:00. Chart line 612c shows standard blood glucose measurements and elevated blood glucose measurements. As illustrated, elevated measurements (e.g., measurements that exceed a predetermined threshold value (e.g., >130 mg/dL; >180 mg/dL)) are visually distinguished (e.g., in a different line weight, in a different color) from standard measurements. In some embodiments, chart line 612c does not visually distinguish elevated measurements from standard measurements. Device 600 receives tap input 617 corresponding to selection of meal logging affordance 614a. In response to detecting tap input 617 at meal logging affordance 614a, device 600 initiates creation of a log entry for a meal (e.g., consumption of food or beverage (e.g., breakfast, lunch, dinner, a snack)). In some embodiments, selection of activity logging affordance 614b initiates creation of a log entry for a physical activity (e.g., exercise, meditation). In some embodiments, selection of mood logging affordance 614c initiates creation of a log entry for a sentiment (e.g., happy, sad, lethargic, energized).

In FIG. 6D, device 600 displays, on touchscreen display 602, log entry creation user interface 618. Log entry creation user interface 618 includes a time selection affordance 618a. In some embodiments, selection of the time selection affordance 618a allows customization of the time corresponding to the log entry. In this example, time selection affordance 618a shows (e.g., defaults to) the current time of 12:00. Log entry creation user interface 618 also includes search bar 618b, which can be selected to initiate searching for a particular food. In some embodiments, when logging an activity or mood, search bar 618b can be used to find specific exercises or sentiment. Log entry creation user interface 618 further includes camera affordance 618c and save affordance 618d. In some embodiments, selection of camera affordance 618c opens the camera of device 600 and allows a user to capture a picture of their meal. In such embodiments, device 600 generates a log entry based on a photo of a meal (e.g., using image recognition software).

Log entry creation user interface 618 includes item selection region 620. In this example, item selection region 620 displays common foods that a user can select for logging. In some embodiments, when logging an activity, item selection region 620 includes selectable affordances corresponding to various activities (e.g., walking, biking, meditating). In some embodiments, when logging a mood, item selection region 620 includes selectable affordances corresponding to various moods/sentiments (e.g., feelings (e.g., anxious, excited, tired)). Device 600 receives tap inputs 622a and 622b corresponding to selection of bread affordance 620a and salad affordance 620b, respectively. In some embodiments, only one selectable affordance within the item selection region 620 can be selected while creating a log entry. In some embodiments, one or more selectable affordance within the item selection region 620 can be selected while creating a log entry. As shown in FIG. 6E, in response to detecting tap inputs 622a and 622b, device 600 displays log entry creation user interface 618 with bread affordance 620a and salad affordance 620b visually different (e.g., bolded) than the other food affordances, indicating these two foods have been selected for logging.

In FIG. 6E, device 600 receives tap input 624 corresponding to selection of save affordance 618d. In response to detecting tap input 624, device 600 generates log entry 614d displayed in log region 614 of hourly log user interface 610, as shown in FIG. 6F.

Figure 6F:
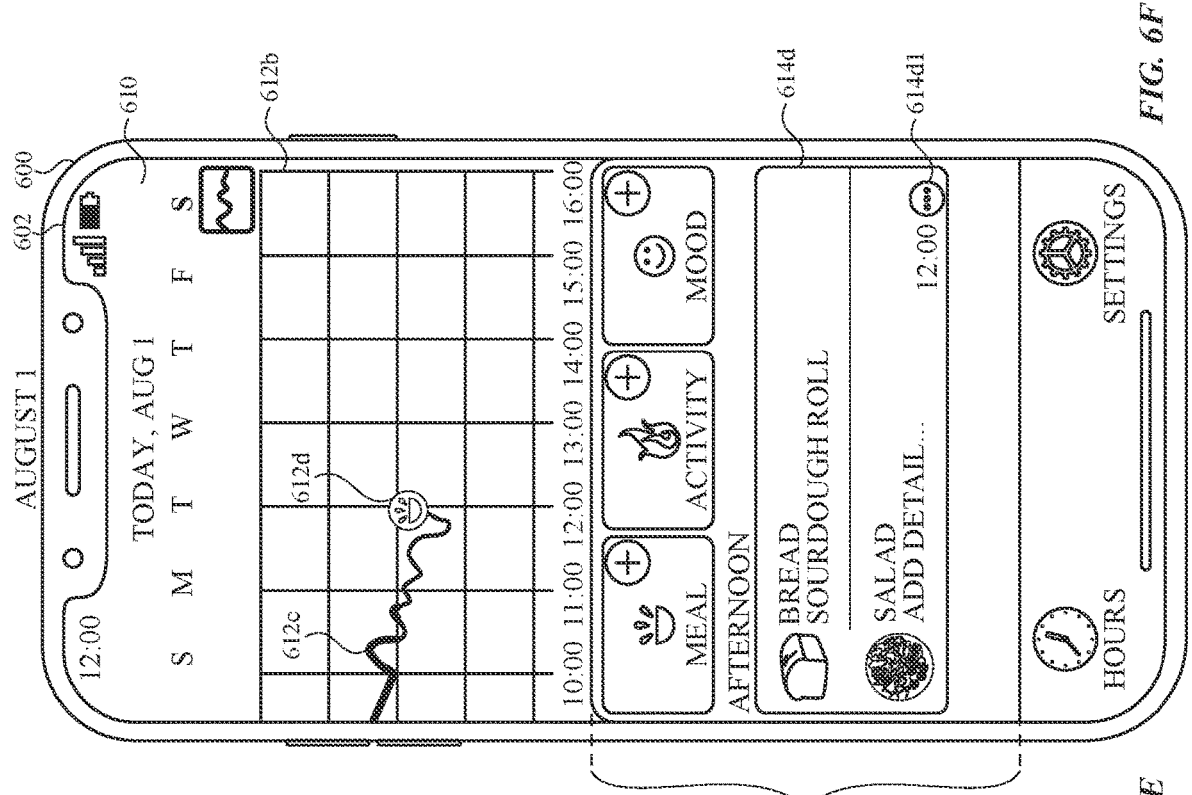
Figure 6E:
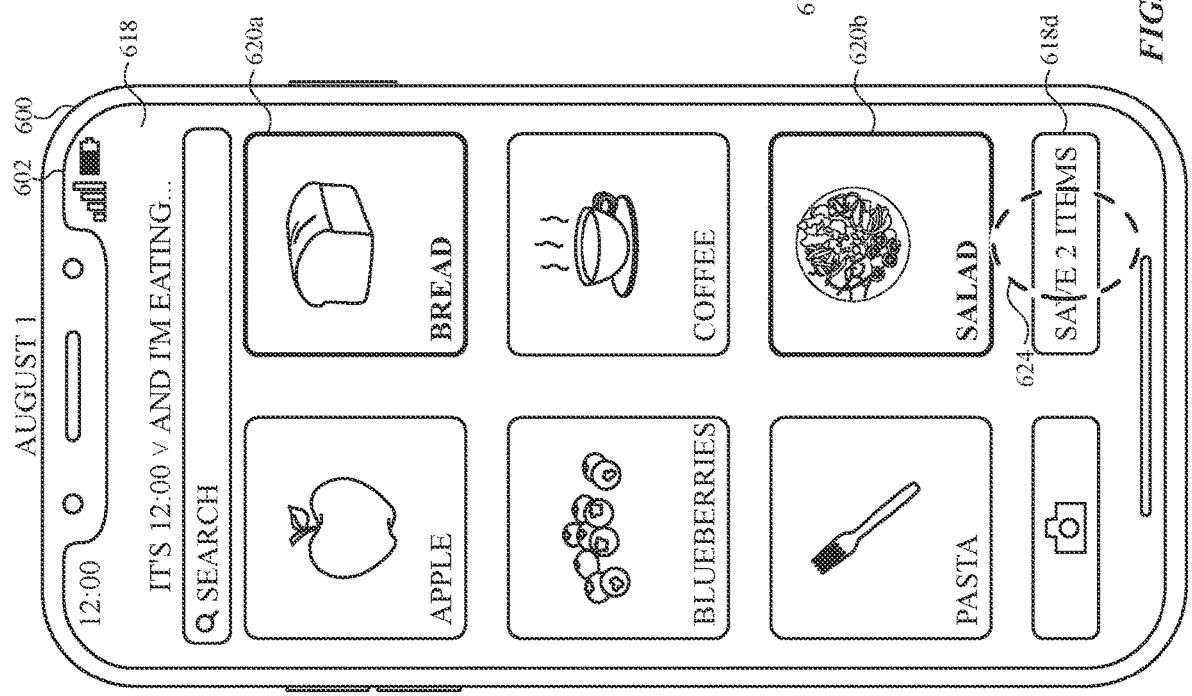
Figure 6H:
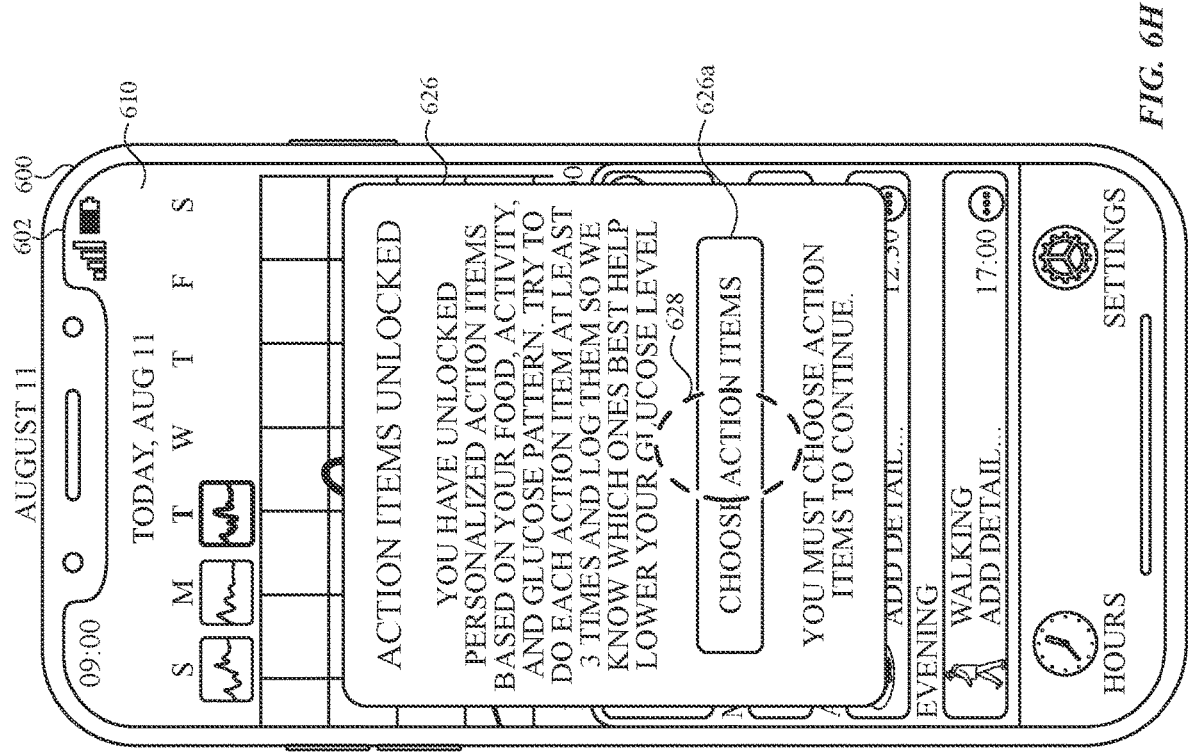

In FIG. 6F, hourly log user interface 610 now includes display of log entry 614d. Log entry 614d includes the foods consumed (e.g., bread and salad) and time indication (e.g., 12:00) corresponding to the time the foods were consumed. Log entry 614d is displayed below "AFTERNOON," which indicates the general time period that the meal was consumed. In this example, each day is divided into four recurring periods of time (e.g., quadrants), which include morning (04:00 to 10:00), afternoon (10:00 to 16:00), evening (16:00 to 22:00), and overnight (22:00 to 04:00). In some embodiments, the quadrants span different ranges of time. In some embodiments, the quadrants are not equal periods of time within a 24-hour period (e.g., two 5-hour periods and two 7-hour periods; longer period of time for the overnight quadrant). In some embodiments, the subsets of a recurring time period are different than quadrants (e.g., the day is divided into sextants or octants or a week is divided into individual days). In some embodiments, a full day is the recurring period of time, without further divisions. In some embodiments, the recurring periods of time are selected (e.g., customized) by the user. Log entry 614d further includes optional details that specify the type of food (e.g., "SOURDOUGH ROLL" is a type of "BREAD"). In this example, "SOURDOUGH ROLL" has been specified below "BREAD" and selectable "ADD DETAIL . . . " is displayed below "SALAD" as a prompt to add details (e.g., notes, specify the type of salad). In some embodiments, selecting "ADD DETAIL . . . " causes device 600 to display a text entry field and a keyboard. In some embodiments, after input of additional details, device 600 ceases display of "ADD DETAIL . . . " and displays the inputted text. Log entry 614d optionally includes a selectable affordance 614d1 (e.g., icon with the three dots) to view details and edit (e.g., add or remove types of food) or delete the log entry. In some embodiments, in response to selecting affordance 614d1 or log entry 614d, device 600 displays a log detail user interface containing specific details about the log entry (e.g., a glucose graph, date, time, and options to edit, duplicate, or delete the log entry).

In addition to generating log entry 614d, device 600 displays meal glyph 612d along chart line 612c. Meal glyph 612d is displayed at a time, e.g., 12:00, along chart region 612b, corresponding to the time that the meal was consumed. In some embodiments, if the log entry was an activity or mood log entry, a corresponding activity or mood glyph would be displayed along chart line 612c. In some embodiments, meal, activity, and mood glyphs are selectable user interface objects, that, when selected, causes device 600 to display a log detail user interface corresponding to the log entry.

Figure 6G:
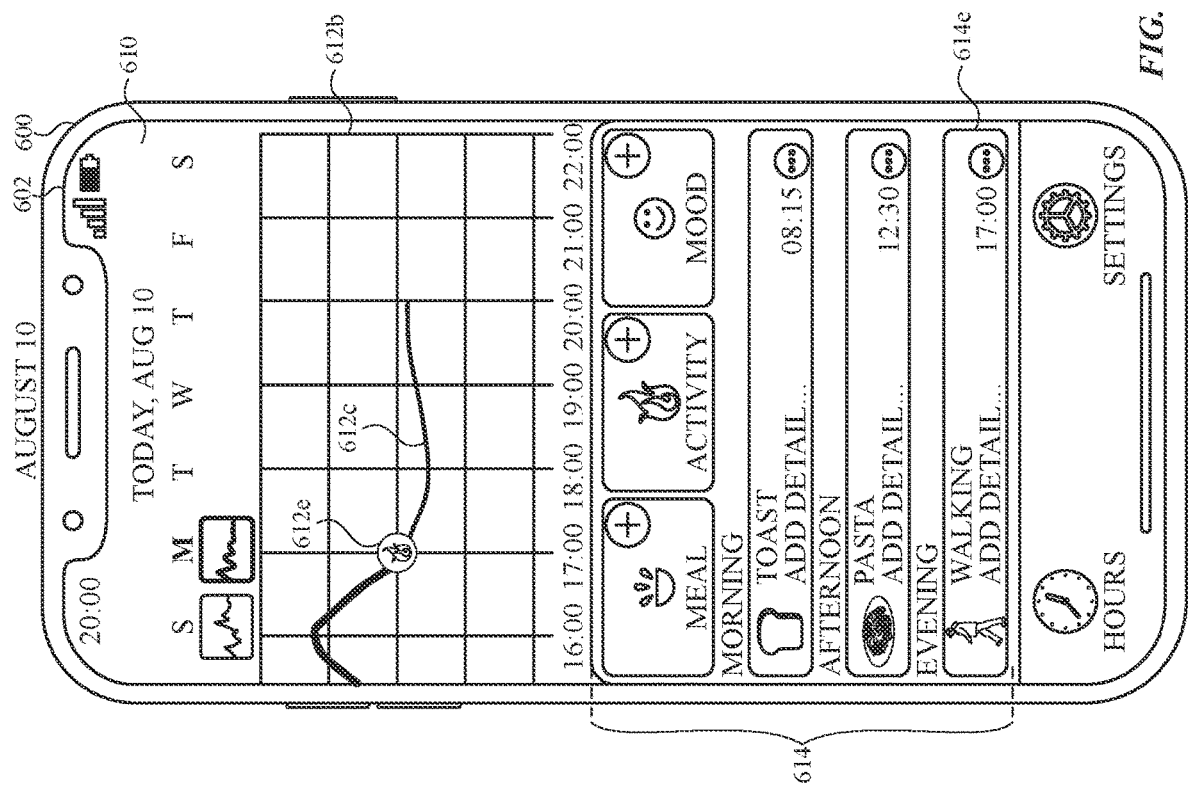

Turning now to FIG. 6G, the current date is August 10, as indicated above device 600. Device 600 displays, on touchscreen display 602, hourly log user interface 610. Hourly log user interface 610 includes chart region 612b with chart line 612e and activity glyph 614e displayed in log region 614. Activity glyph 612e corresponds to log entry 614e (e.g., walking). In some embodiments, device 600 can receive swipe inputs corresponding to chart region 612b to scroll (e.g., horizontally scroll) and view previously collected data. In some embodiments, previously collected data within chart region 612b includes meal glyphs along chart line 612c at the times corresponding to each log entry for a morning meal (e.g., toast) and an afternoon meal (e.g., pasta), as shown in log region 614.

Ten days after onboarding, on August 11, as shown in FIG. 6H, device 600 displays action notification 626 over hourly log user interface 610. Action notification 626 indicates that the baseline phase is now complete and next phase (e.g., the action phase) of the glucose monitoring feature is available. In some embodiments, action notification 626 is displayed after a minimum amount of time has passed since the start of the baseline phase (e.g., starting data collection). In some embodiments, action notification 626 is displayed after enough physiological data (e.g., blood glucose measurements) have been received by device 600. In some embodiments, action notification 626 is displayed after enough elevated blood glucose measurements have been received by device 600. In some embodiments, the action phase is unavailable (e.g., locked) until a criteria, such as the ones described, have been met. Action notification 626 includes continue affordance 626a (e.g., "CHOOSE ACTION ITEMS"). Device 600 detects tap input 628 corresponding to selection of continue affordance 626a, and in response to tap input 628, device 600 initiates action phase set up.

Figure 6I:
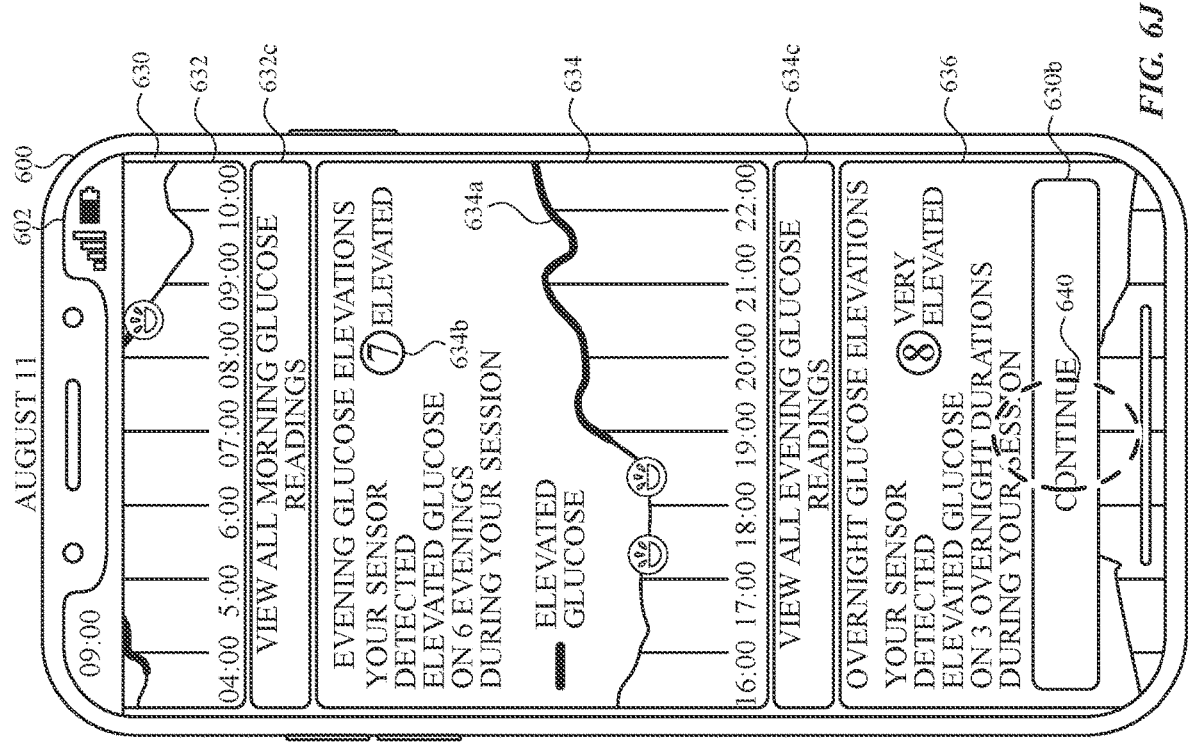

As shown in FIG. 6I, in response to detecting tap input 628, device 600 initiates action phase set up by displaying, on touchscreen display 602, baseline summary user interface 630. Baseline summary user interface 630 includes an informational affordance 630a, which details how physiological data (e.g., blood glucose data) received by device 600 is presented, and continue affordance 630b. Informational affordance 630a includes elevation values (e.g., one through ten) corresponding to the elevation level (e.g., no elevation, minor elevation, some elevation, elevated, very elevated) of a received blood glucose measurement. In some embodiments, elevation values are presented instead of concentration values (e.g., mg/dL). In some embodiments, elevation values are based on (e.g., derived from) blood glucose measurements over a period of time (e.g., from 10:00 to 16:00; a day; every day for seven days from 09:00 to 12:00).

Baseline summary user interface 630 of FIG. 6I further includes morning baseline affordance 632. Morning baseline affordance 632 shows morning baseline graph 632a, which is a visual representation of elevated data received by device 600 during morning quadrant (e.g., period of time in the morning (e.g., from 04:00 to 10:00)) during the baseline phase (e.g., onboarding phase, initial phase, sensor phase), and morning elevation value 632b. In some embodiments, morning baseline graph 632a depicts the instance (e.g., the single morning (e.g., the morning of August 8$^{th}$)) having the most elevated physiological data received by device 600 during the morning quadrant of the baseline phase. In some embodiments, morning baseline graph 632a is based on (e.g., derived from) all physiological data (e.g., displayed as an average) received by device 600 during the morning quadrant of the baseline phase (e.g., lasting 10 days; for a week). In some embodiments, baseline summary user interface 630 presents subsets of a recurring time period (e.g., a day; a week) different than quadrants (e.g., the day is divided into sextants or octants or a week is divided into individual days).

Figure 6J:
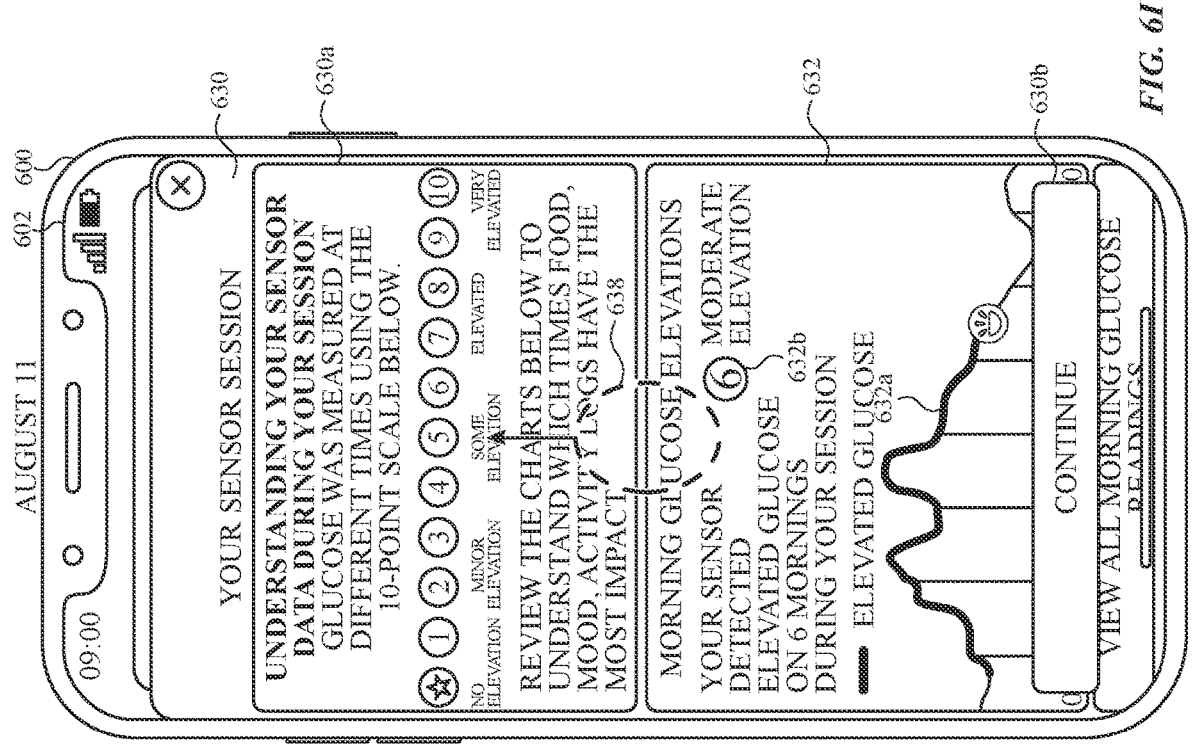
Figure 6P:
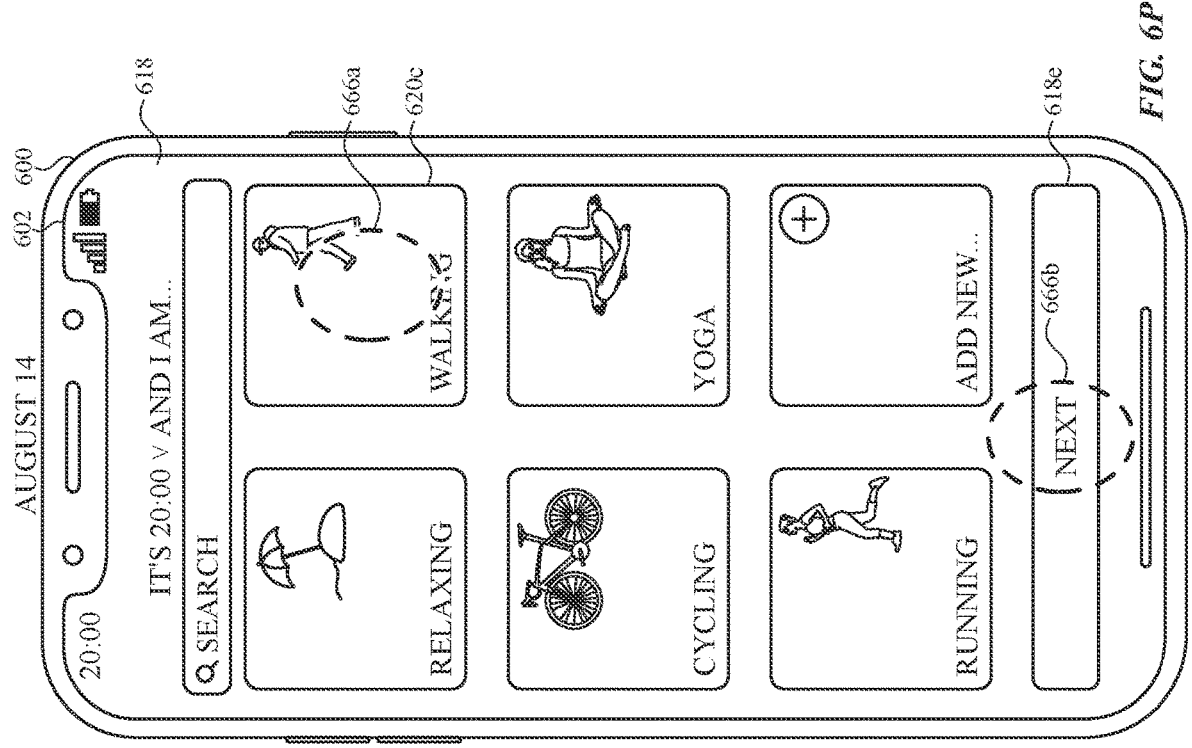

As shown in FIG. 6I, device 600 detects swipe input 638, corresponding to a request to scroll baseline summary user interface 630, on touchscreen display 602. In response to receiving swipe input 638, device 600 displays a second portion of baseline summary user interface 630, as shown in FIG. 6J. In FIG. 6J, baseline summary user interface 630 includes a portion of morning baseline affordance 632, along with a selectable view all morning data affordance 632c. In some embodiments, selection of view all morning data affordance 632c causes device 600 to display a user interface having one or more graphs, including morning baseline graph 632a, corresponding to physiological data (e.g., blood glucose measurements) received by device 600 during the morning quadrant (e.g., period of time in the morning (e.g., from 04:00 to 10:00)) of the baseline phase. In some embodiments, in response to selection of view all morning data affordance 632c, device 600 displays graphs corresponding to instances of receiving elevated physiological data (e.g., measurements above a threshold).

In FIG. 6J, baseline summary user interface 630 includes evening baseline affordance 634. Evening baseline affordance 634 is analogous to morning baseline affordance 632, however, evening baseline affordance 634 corresponds to physiological data (e.g., blood glucose measurements) received by device 600 during the evening quadrant (e.g., period of time during the evening (e.g., from 16:00 to 22:00)) of the baseline phase. Evening baseline affordance 634 includes evening baseline graph 634a, which shows the period of time during the evening (e.g., from 16:00 to 22:00) along the x-axis and blood glucose measurements received by device 600 along the y-axis. Portions of evening baseline graph 634a containing elevated measurements are visually distinct (e.g., having a thicker line weight) from non-elevated measurements. Evening baseline affordance 634 includes evening elevation value 632b. Baseline summary user interface 630 includes selectable view all evening data affordance 634c, which is analogous to selectable view all morning data affordance 632c.

Baseline summary user interface 630 further includes a portion of overnight baseline affordance 636, which in analogous to morning baseline affordance 632 and evening baseline affordance 634. Overnight baseline affordance 636 corresponds to physiological data (e.g., blood glucose measurements) received by device 600 during the overnight quadrant (e.g., period of time overnight (e.g., from 22:00 to 04:00)) of the baseline phase. In some embodiments, after receiving a scroll input, device 600 displays baseline summary user interface 630 showing the entire overnight baseline affordance 636 and a selectable view all overnight data affordance, analogous to selectable view all morning data affordance 632c and selectable view all evening data affordance 634c.

In the example described, device 600 displays affordances corresponding to physiological data received during the morning, evening, and overnight quadrants during the baseline phase (e.g., an initial period of time (e.g., ten days, a week)) and does not display an affordance corresponding to physiological data received during the afternoon quadrant (e.g., period of time in the afternoon (e.g., from 10:00 to 16:00)). In some embodiments, device 600 determines, based on the received physiological data, the one or more portions of the day having the most elevated blood glucose measurements (e.g., during the baseline phase) and displays baseline affordances accordingly. In some embodiments, the portions of the day having the most elevated blood glucose measurements, and therefore are displayed by device 600, contain the highest measurements (e.g., the three highest measurements as between the four quadrants of the day). In some embodiments, the portions of the day that are displayed by device 600 have the highest elevation values. In some embodiments, the portions of the day that are displayed by device 600 have more time spent in an elevated measurement state. Therefore, in some embodiments, device 600 displays a combination of the morning, afternoon, evening, and overnight quadrants. In some embodiments, device 600 displays affordances corresponding to each quadrant (e.g., morning, afternoon, evening, overnight).

As shown in FIG. 6J, device 600 receives tap input 640 corresponding to selection of continue affordance 630b. In response to detecting tap input 640, device 600 displays, on touchscreen display 602, task selection user interface 642, as shown in FIG. 6K. Task selection user interface 642 currently includes morning task affordance 644, evening task affordance 646, and a portion of overnight task affordance 648. Each task affordance (e.g., 644, 646, 648) includes a number of selectable tasks (e.g., three) to be chosen to be performed during the specified part of the day (e.g., morning, evening). The selectable tasks are to perform either a physical activity (e.g., "TRY AN ACTIVITY AROUND BREAKFAST") or consume or forgo consumption of a type of food (e.g., "EAT CARBS DURING DINNER"; "AVOID SNACKS AROUND DINNER") during the specified part of the day. In some embodiments, the tasks presented to affect elevated blood glucose measurements are the same for each user (e.g., standard tasks). In some embodiments, performance of these tasks has a positive effect on (e.g., reduces elevation of) blood glucose measurements. Device 600 receives swipe input 650 corresponding to a request to scroll task selection user interface 642.

In response to detecting swipe input 650, device 600 displays another portion of task selection user interface 642, as shown in FIG. 6L. Task selection user interface 642 shows a portion of morning task affordance 644, along with evening task affordance 646 and overnight task affordance 648. Evening task affordance 646 includes three selectable tasks 646a-646c to be performed to affect blood glucose measurements received by device 600 during the evening. Overnight task affordance 648 includes three selectable tasks 648a-648c to be performed to affect blood glucose measurements received by device 600 overnight. Selectable task 646a (which reads, "TRY AN ACTIVITY DURING DINNER") is a task to be performed during the evening quadrant (e.g., period of time during the evening (e.g., from 16:00 to 22:00)) to affect blood glucose measurements received by device 600 during the same period of time. Selectable task 648b (which reads, "TRY SMALLER PORTIONS OF HIGH RESPONSE FOODS AT DINNER") is a task to be performed at dinner, typically within the evening quadrant to affect blood glucose measurements received by device 600 during the overnight quadrant (e.g., period of time overnight (e.g., from 22:00 to 04:00)). In some embodiments, tasks are to be performed within the designated part of the day. In some embodiments, tasks can be performed near the designated part of the day. In some embodiments, tasks are to be logged within the designated part of the day.

In FIG. 6L, device 600 detects tap input 652a corresponding to selection of selectable task 646a and tap input 652b corresponding to selection of selectable task 648a. As shown in FIG. 6M, in response to receiving tap inputs 652a and 652b, device 600 displays, on touchscreen display 602, selectable task 646a and selectable task 648a having check marks as a confirmatory indication that each task has been selected. Upon selection of the tasks, device 600 displays selectable affordances "LEARN MORE" and "EXAMPLES" below selected tasks 646a and 648a. In some embodiments, selection of the "LEARN MORE" affordance causes device 600 to display additional information pertaining to the selected task. In some embodiments, selection of the "EXAMPLES" affordance causes device 600 to display one or more examples corresponding to the selected task (e.g., go for a walk after dinner; bike ride before dinner; opt for a low-carb dessert before bed; forgo dessert). Upon selecting tasks 646a and 648a, device 600 displays continue affordance 642a (which reads, "SELECT 2 ACTION ITEMS"). Device 600 detects tap input 654 corresponding to selection of continue affordance 642a, which completes action phase set up.

In response to receiving tap input 654 to complete action phase set up, device 600 displays progress user interface 656, as shown in FIG. 6N. Device 600 also displays progress tab affordance 616c for navigating to progress user interface 656. Progress user interface 656 includes counter 656a, which has a live count for the number of tasks completed (e.g., "ACTION ITEMS COMPLETED"), currently showing "0" and the number of days remaining, currently showing "7". The action phase for the glucose monitoring feature is a predetermined period of time (e.g., 7 days, 10 days), as indicated by the number of days remaining.

Progress user interface 656 of FIG. 6N also includes an evening region 658 and a portion of overnight region 660. Each region contains instructional text for when to perform the selected task. Evening region 658 shows selected task 646a "TRY AN ACTIVITY AROUND DINNER" along with instructions for tracking and selectable affordances "LEARN MORE" and "EXAMPLES". Overnight region 660 contains elements analogous to those of evening region 658. In some embodiments, device 600 detects a swipe input to scroll the displayed progress user interface 656 and displays the entire evening region 658. Device 600 detects tap input 662 corresponding to selection of hours tab affordance 616a and, in response, navigates to hourly log user interface 610 similar to that shown in FIG. 6G and FIG. 6O.

Figure 6O:
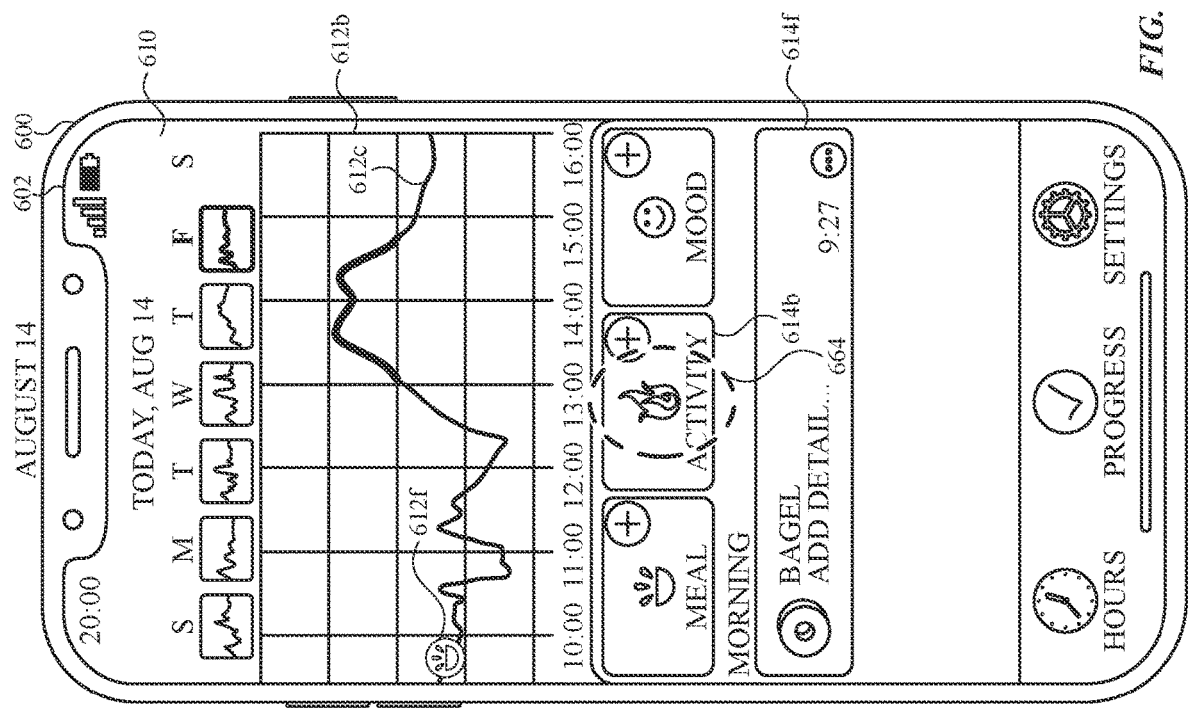
Figure 6R:
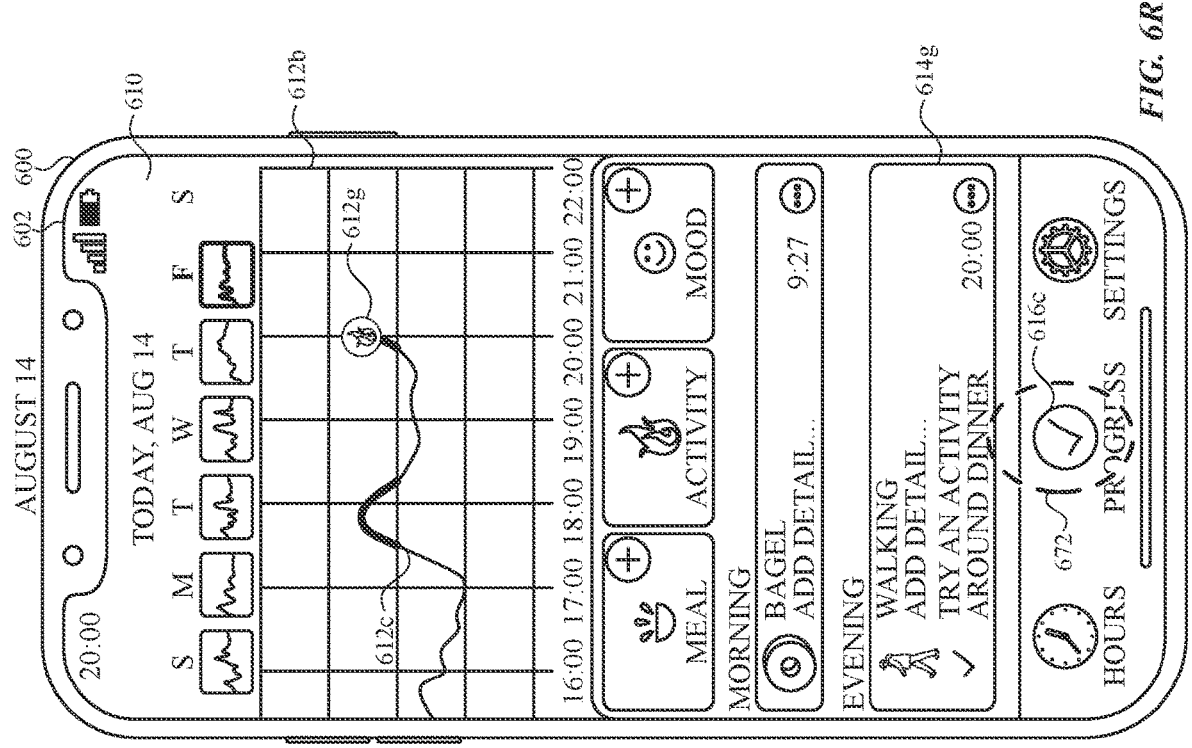

In FIG. 6O, a few days have passed and the current date is August 14, as indicated above device 600. In some embodiments, device 600 displays hourly log user interface 610 with chart region 612b including the current time (e.g., 20:00) along the x-axis. In some embodiments, device 600 detects a swipe input to scroll chart region 612b to display blood glucose data collected at an earlier time. In this example, device 600 displays hourly log user interface 610 with chart region 612b showing chart line 612c from approximately 09:30 to 16:00. Meal glyph 612f corresponds to "BAGEL" log entry 614f. Device 600 detects tap input 664 corresponding to selection of activity logging affordance 614b.

In response to receiving tap input 664 at activity logging affordance 614b, device 600 initiates logging of an activity, as shown by log entry creation user interface 618 in FIG. 6P. As discussed with reference to FIG. 6D, log entry creation user interface 618 includes selectable affordances corresponding to various activities (e.g., relaxing, walking, running). Device 600 detects tap input 666a at walking affordance 620c, followed by tap input 666b at next affordance 618e. In response to receiving tap inputs 666a and 666b, device 600 displays task confirmation user interface 668, as shown in FIG. 6Q.

Figure 6Q:
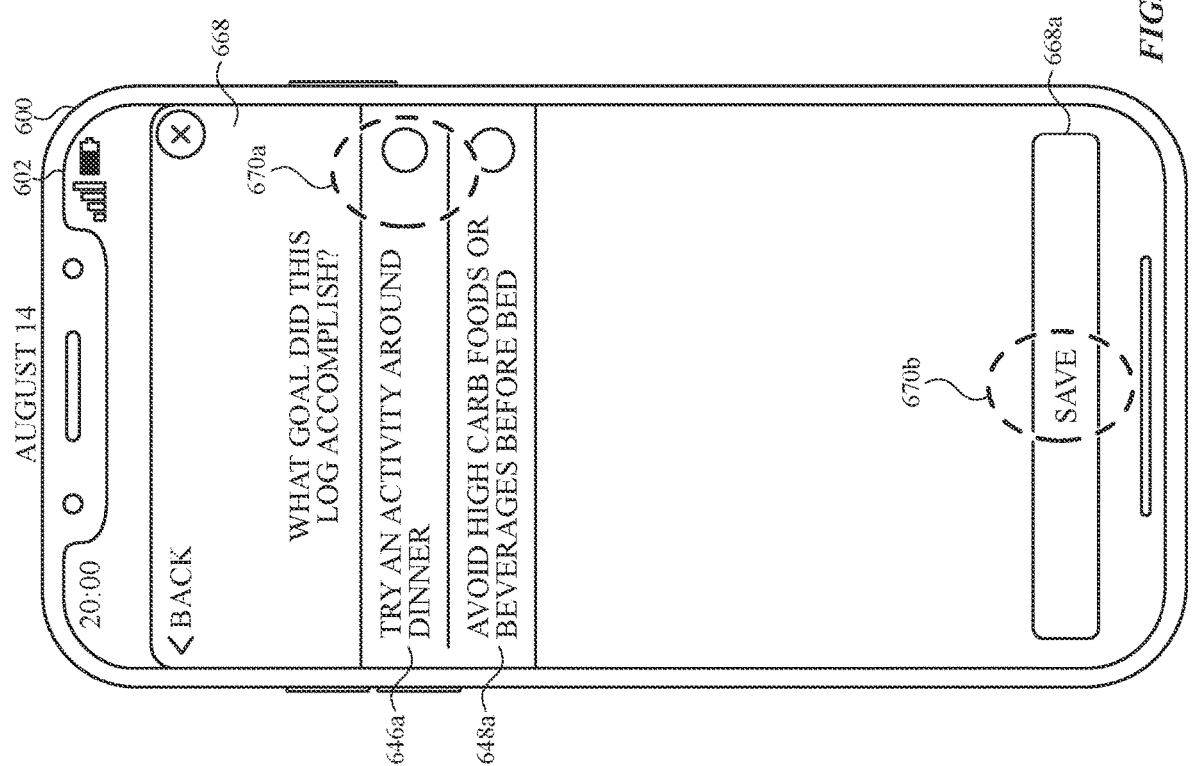

FIG. 6Q illustrates device 600 displaying, on touchscreen display 602, task confirmation user interface 668. Task confirmation user interface 668 is presented while creating a log entry after tasks to be performed during the action phase have been selected, as shown in FIGS. 6I-6N. Task confirmation user interface 668 includes task 646a (which reads, "TRY AN ACTIVITY DURING DINNER") and task 648a (which reads, "AVOID HIGH CARB FOODS OR BEVERAGES BEFORE BED"), both of which were selected during task selection described with reference to FIGS. 6I-6N. In some embodiments, multiple tasks (e.g., three or more) are presented in task confirmation user interface 668. In some embodiments, task confirmation user interface 668 presents the task corresponding to the time specified on log entry creation user interface 618 (e.g., present task 626a when the time specified on log entry creation user interface 618 is between 16:00 and 22:00) and does not present task(s) that do not correspond to the time specified. In some embodiments, device 600 forgoes displaying task confirmation user interface 618 when the time specified on log entry creation user interface 618 does not correspond to the part of the day for performing a selected task (e.g., do not display task confirmation user interface 618 for log entries that are not between 16:00 and 22:00 or 22:00 and 04:00). In some embodiments, device 600 displays task confirmation user interface 618 regardless of the time specified on log entry creation user interface 618 and tasks can be marked as completed outside of the part of the day designated for performing that task (e.g., create a log entry at 20:00 and select task 648a to be performed between 22:00 and 04:00). In some embodiments, in response to detecting an input selecting a task to be marked as completed outside of the part of the day designated for performing that task, device 600 displays an informative message that the effect of performing that selected task outside of the part of the day designated for performing that task is inconclusive to the physiological data collected (e.g., "The effects of your logged entry "avoid high carb foods or beverages before bed" at 20:00 are inconclusive for your overnight blood glucose measurements").

In the example detailed in FIG. 6Q, device 600 detects tap input 670a corresponding to selection of task 646a. In some embodiments, in response to selection of task 646a, task 646a is shown with a check mark indication. Device 600 also detects tap input 670b corresponding to selection of save affordance 668a. In response to receiving tap input 670b, device 600 saves the activity log entry and displays hourly log user interface 610.

As shown in FIG. 6R, device 600 displays, on touchscreen display 602, hourly log user interface 610 with an updated chart region 612b. The updated chart region 612b shows the period of time ranging from 15:30 to 22:00 with chart line 612c and activity glyph 612g. Activity glyph 612g corresponds to "WALKING" log entry 614g. "WALKING" log entry 614g includes an indication that task 646a was satisfied by walking at 20:00. In contrast, "BAGEL" log entry 614f does not satisfy a user-selected task, and therefore does not include an indication similar to that of "WALKING" log entry 614g. Device 600 receives tap input 672 corresponding to selection of progress tab affordance 616c, and in response, displays progress user interface 656, as shown in FIG. 6S.

As shown in FIG. 6S, device 600 displays, on touchscreen display 602, progress user interface 656, similar to that described with respect to FIG. 6N. While FIG. 6N illustrates progress user interface 656 on the first day of the action phase (e.g., after completing action phase set up, August 11), FIG. 6S shows progress user interface 656 during the action phase (e.g., on August 14). Counter 656a is updated to show that five action items (e.g., tasks) have been completed and there are three more days in the action phase to perform the tasks displayed on progress user interface 656.

In FIG. 6S, the evening region 658 includes selected task 646a, along with "WALKING" log entry 614g and "BIKING" log entry 614h, corresponding to log entries that satisfied task 646a of "TRY AN ACTIVITY AROUND DINNER." Log entries 614g and 614h include elevation values to indicate the impact of performing the activity (e.g., walking, biking) on blood glucose measurements received by device 600 during the evening period (e.g., from 16:00 to 22:00) of the day the activity was performed (e.g., walking on August 14, biking on August 13). In comparison to the typical evening elevation score of "7," received by device 600 during the baseline phase, walking and biking both caused a decrease in evening elevation score (e.g., to "3", to "2") for their respective days. Device 600 receives swipe input 674 corresponding to a request to scroll progress user interface 656 to view more of overnight region 660.

As shown in FIG. 6T, in response to swipe input 674, device 600 displays more of progress user interface 656, which now shows a portion of evening region 658 that includes "BIKING" log entry 614h and all of overnight region 660. Overnight region 660 includes information similar to that described with respect to in FIG. 6N, including task 648a, and further includes log entries (e.g., "SUGAR FREE CHEESECAKE," "LOW CARB OATMEAL COOKIE," "WATER WITH DINNER,") that correspond to performing task 648a.

Figure 6U:
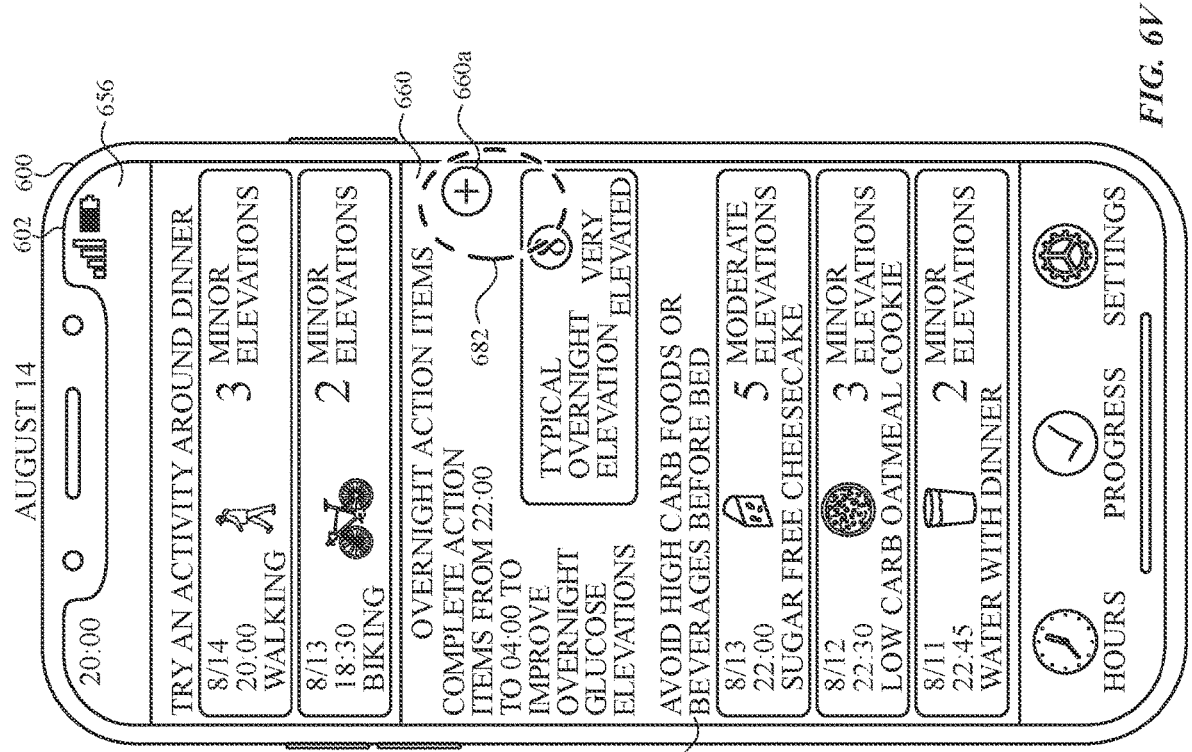

Device 600 receives tap input 676 corresponding to selection of "BIKING" log entry 614h. As shown in FIG. 6U, in response to detecting tap input 676, device 600 displays, on touchscreen display 602, log detail user interface 678. Log detail user interface 678 includes details about "BIKING" log entry 614h, including the date and time the activity was performed (e.g., 18:30 on August 13) and the elevation value for blood glucose measurements received by device 600 during the evening period (e.g., from 16:00 to 22:00) on August 13. Log detail user interface 678 also includes selected task 646a and the typical evening elevation score of "7."

In FIG. 6U, log detail user interface 678 shows comparison region 678a. Comparison region 678a includes a chart having evening baseline graph 634a overlaid on (e.g., superimposed onto, displayed concurrently with) biking graph 678b. As previously described with respect to FIG. 6J, evening baseline graph 634a is a graphical representation of blood glucose measurements received by device 600 during an evening period (e.g., from 16:00 to 22:00) during the baseline phase. Biking graph 678b is a graphical representation of blood glucose data received by device 600 during the evening period on August 13 and includes an activity glyph at 18:30 to show when task 646a was performed. Evening baseline graph 634a and biking graph 678b both include portions that are visually distinct (e.g., thicker line weight) from the rest of the graph. The visually distinct portions of each graph represent blood glucose measurements that are above a predetermined threshold and are considered to be elevated measurements.

Log detail user interface 678 includes selectable exit affordance 678c. Device 600 detects tap input 680 corresponding to selection of exit affordance 678c, and in response, device 600 ceases display of log detail user interface 678 and displays progress user interface 656, as shown in FIG. 6V.

Figure 6V:
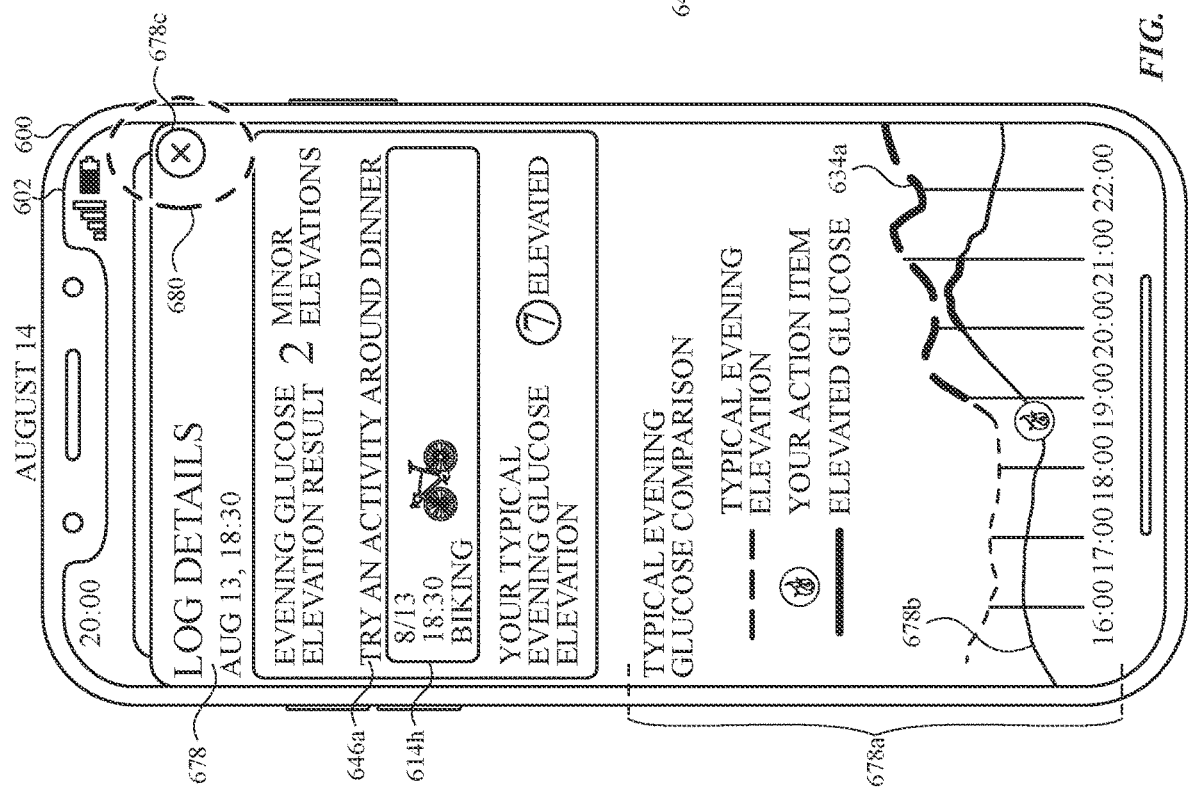

In FIG. 6V, device 600 returns to displaying progress user interface 656. Progress user interface includes selectable plus affordance 660a within overnight region 660. Device 600 detects tap input 682 corresponding to selection of plus affordance 660a and, in response, initiates a process for selecting a new task to be performed during the overnight period of time.

Figure 6W:
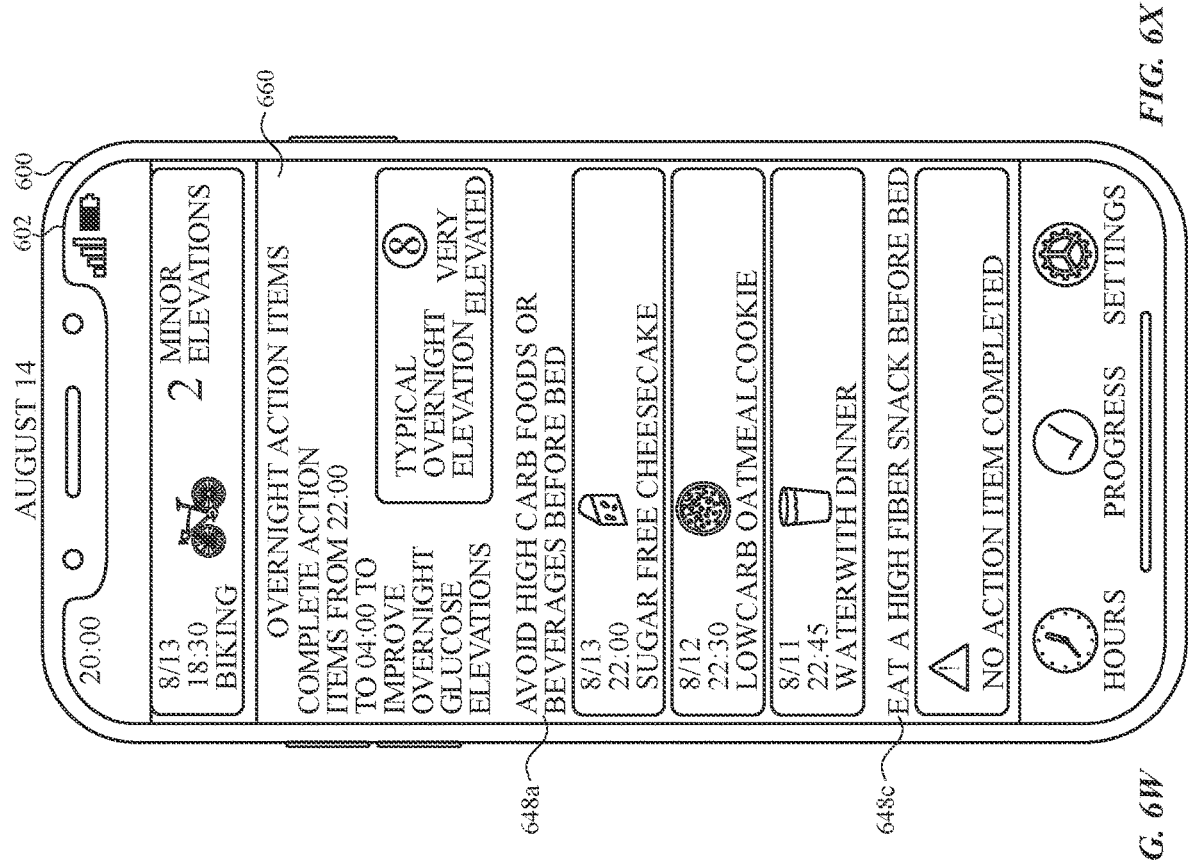

As shown in FIG. 6W, in response to receiving tap input 682, device 600 displays task addition user interface 684. Task addition user interface 684 includes selectable tasks 648b and 648c to be performed to affect blood glucose measurements received by device 600 overnight. Tasks 648b and 648c are the tasks that were not selected during action phase set up, described in further detail with reference to FIGS. 6I-6N. In some embodiments, plus affordance 660a is not displayed within overnight region 660, and therefore task addition user interface 684 is unavailable, until the current task (e.g., "AVOID HIGH CARB FOODS OR BEVERAGES BEFORE BED") has been completed (e.g., performed, logged) a number of times (e.g., three times). Device 600 detects tap input 686a corresponding to selection of task 648c (which reads, "EAT A HIGH FIBER SNACK BEFORE BED"). In some embodiments, in response to receiving tap input 686a, device 600 displays task 648c with an indication that it has been selected (e.g., with a check mark).

Figure 6X:
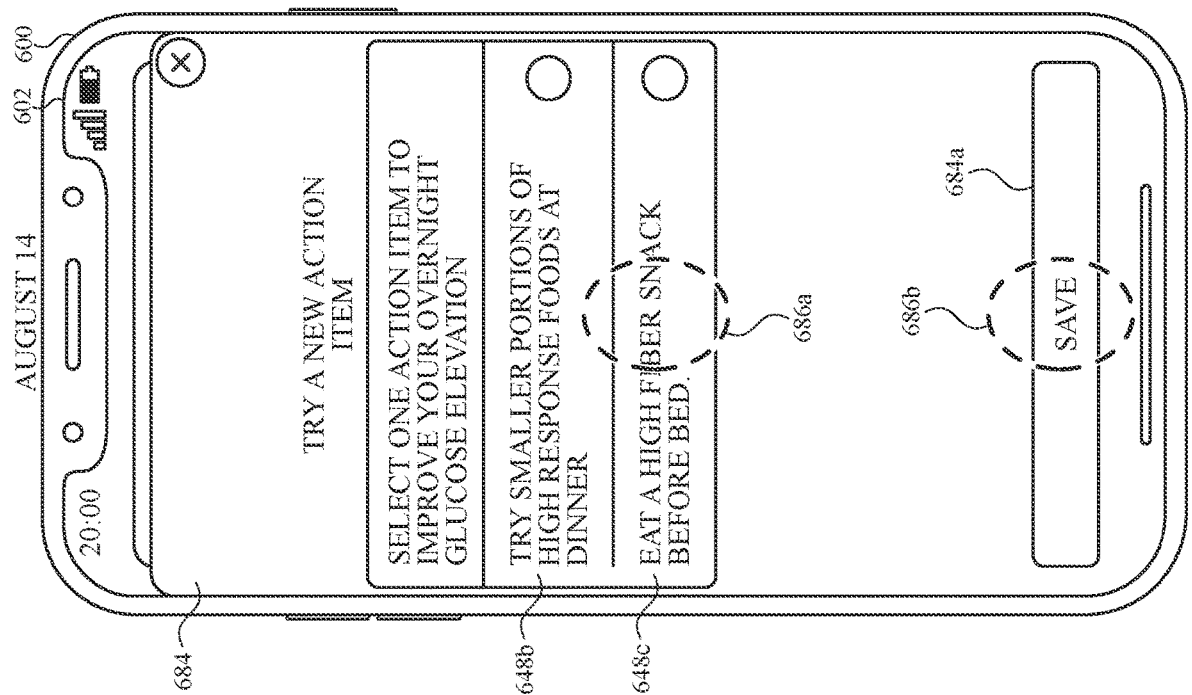

As shown in FIG. 6X, after receiving tap input 686a, device 600 detects tap input 686b corresponding to selection of save affordance 684a. In response to receiving tap input 686b, device 600 displays progress user interface 656 having newly selected task 648c listed in overnight region 660. Within overnight region 660, task 648a shows three log entries corresponding to performing "AVOID HIGH CARB FOODS OR BEVERAGES BEFORE BED" and task 648c shows that no log entries corresponding to performing "EAT A HIGH FIBER SNACK BEFORE BED" have been completed yet. In some embodiments, after adding a new task, task 648c is displayed as a selectable option on task confirmation user interface 668 while creating a new log entry.

Figure 6Y:
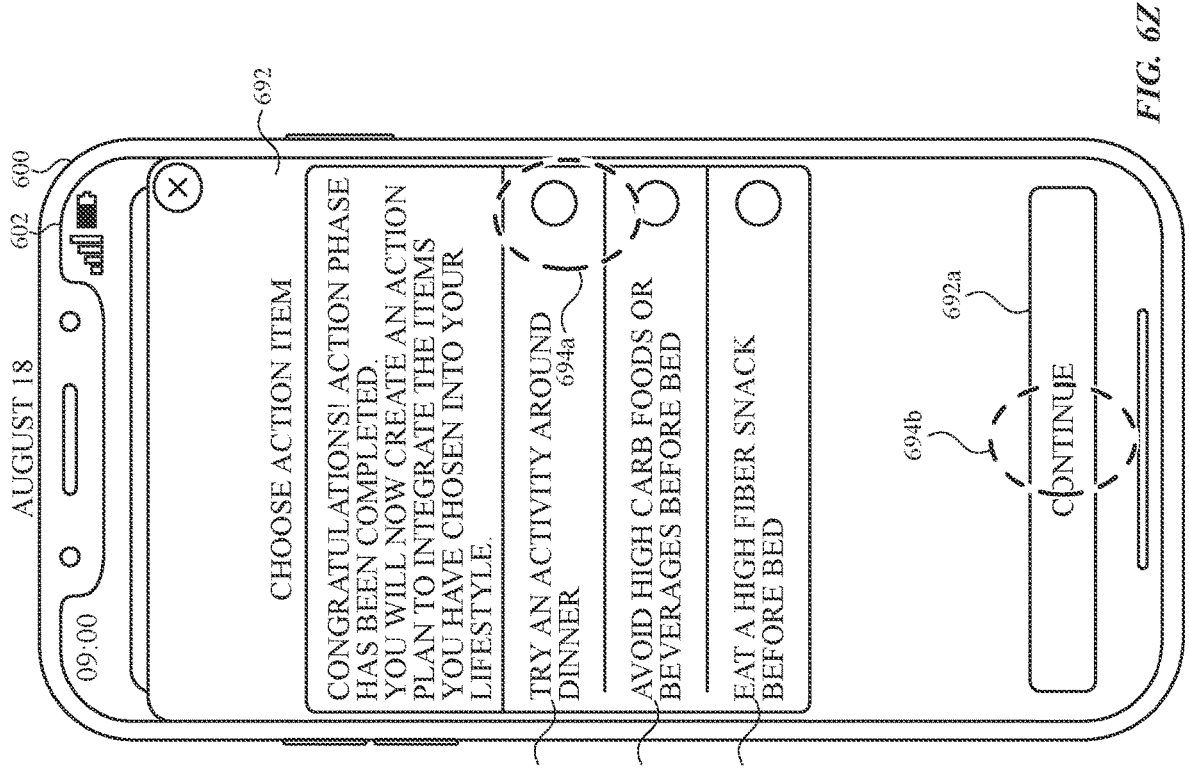

Turning now to FIG. 6Y, the date is currently August 18, seven days after starting the action phase, and the current time is 09:00. Device 600 displays off boarding notification 688 over hourly log user interface 610. In some embodiments, off boarding notification 688 is displayed over progress user interface. Off boarding notification 688 indicates that the action phase is now complete and the next phase (e.g., goal phase) of the glucose monitoring feature is available. Device 600 detects tap input 690 corresponding to selection of continue affordance 688a (e.g., "ADD A GOAL") within off boarding notification 688. In response to receiving tap input 690, device 600 initiates creating a goal in FIG. 6Z.

Figure 6Z:
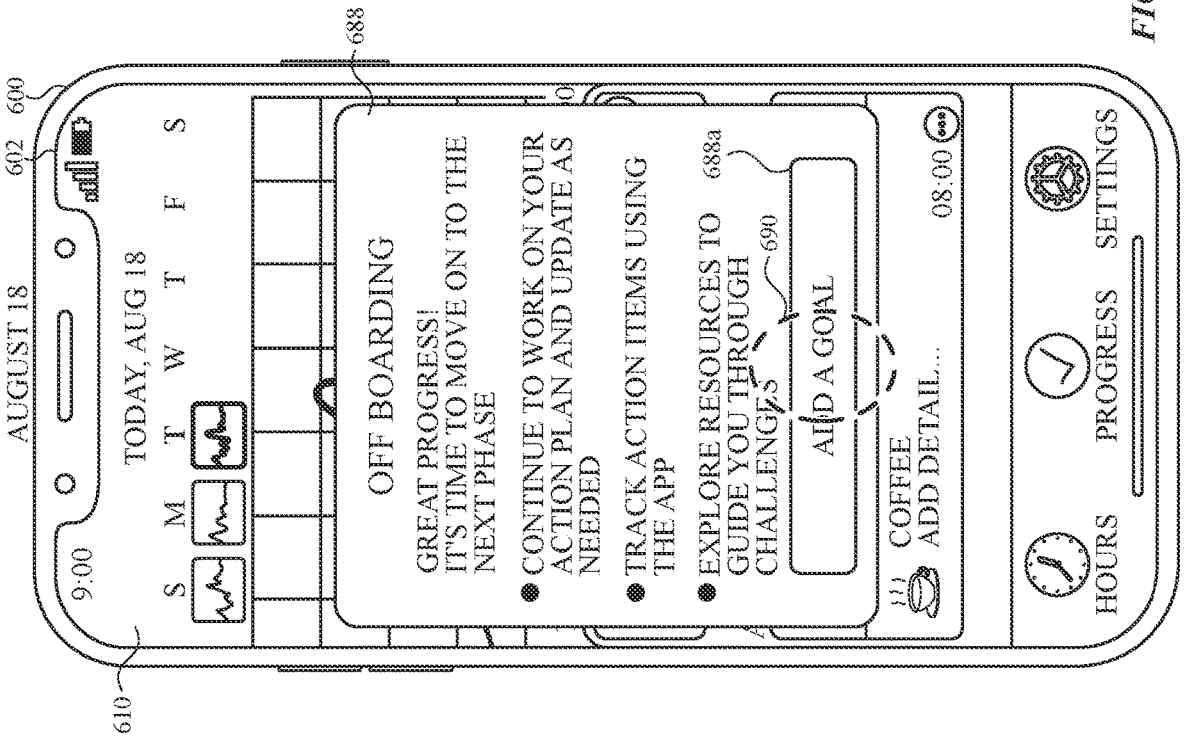

As shown in FIG. 6Z, device 600 displays, on touchscreen display 602, goal selection user interface 692. Goal selection user interface 692 includes selectable tasks 646a, 648a, and 648c, which were performed and tracked during action phase. In some embodiments, tasks are displayed on goal selection user interface 692 if the task was completed a number of times (e.g. three times) during the action phase. Device 600 detects tap input 694a corresponding to selection of task 646a "TRY AN ACTIVITY AROUND DINNER." In some embodiments, in response to receiving tap input 694a, device 600 displays task 646a with an indication that it was selected (e.g., with a check mark). After selection of task 694a, device 600 receives tap input 694b corresponding to selection of continue affordance 692a. In response to detecting tap input 694b, device 600 displays goal customization user interface 696, as shown in FIG. 6AA.

In FIG. 6AA, device 600 displays goal customization user interface 696. Goal customization user interface 696 includes task 646a along with selectable text fields 696a and 696b and day field 696c for customizing the goal based on task 646a. Text field 696a corresponds to specifying the activity to be performed (e.g., walking, yoga, running) and text field 696b corresponds to specifying the duration of time to perform the activity (e.g., 20 minutes, 60 minutes). Device 600 detects tap inputs 698a and 698b corresponding to selection of text fields 696a and 696b. In some embodiments, in response to receiving tap inputs 698a and 698b at text fields 696a and 696b for customizing the goal, device 600 displays a keyboard for entering the custom text. Device 600 also detects tap input 698c corresponding to selection of day field 696c. In some embodiments, in response to receiving tap input 698c at day field 696c, device 600 shows a list from one through seven, for selecting how many times per week to perform the goal. In some embodiments, goal customization user interface 696 includes a customization field for specifying when during the recurring subset of the recurring time period to perform customized goal based on task 646a (e.g., after eating dinner, before eating dinner, concurrently with a meal).

In FIG. 6AB, device 600 display goal customization user interface 696 having text fields 696a and 696b completed to read, "DO YOGA FOR 20 MINUTES" and day field 696c set to "5" times per week. Device 600 receives tap input 6100 corresponding to selection of continue affordance 696d. In response to detecting tap input 6100, device 600 saves customized goal 6102, as shown in FIG. 6AC.

In FIG. 6AC, device 600 continues displaying goal customization user interface 696 having customized goal 6102 based on task 646a. Goal customization user interface 696 now includes additional selectable affordances to "EDIT" and "DELETE" customized goal 6102. Goal customization user interface 696 further includes selectable add affordance 696e. In some embodiments, selecting add affordance 696e causes device 600 to display goal selection user interface 692, similar to that shown in FIG. 6Z. Device 600 receives tap input 6104 corresponding to selection of save affordance 696f. In response to detecting tap input 6104, device 600 displays progress user interface 656, as shown in FIG. 6AD.

In FIG. 6AD, device 600 displays, on touchscreen display 602, progress user interface 656 that is updated when in the goal phase. Progress user interface 656 includes selectable week affordances 656b and 656c. Week affordance 656c, corresponding to the current week of "August 18-24," is visually highlighted (e.g., in bold) to show that it is currently selected. Below week affordance 656c, device 600 displays "0%" to indicate that the goal has not been completed. In some embodiments, in response to selection of week affordance 656b for the week of "August 11-17," corresponding to the action phase, device 600 displays week affordance 656b as visually highlighted (e.g., in bold) and includes evening region 658 and overnight region 600 in progress user interface 656, as described with reference to FIGS. 6S-6V.

In this example, in FIG. 6AD, when week affordance 656c is selected, progress user interface 656 includes customized goal 6102 and selected task 646a. Customized goal 6102 includes progress indicators 6102a-6012e. Progress indicator 6102a is a plus sign that can be selected to confirm a completed instance of the customized goal. Progress indicator 6102e is reads "GOAL" beneath it, to indicate that upon the fifth completed instance of the customized goal, the goal has been met for the week.

Turning now to FIG. 6AE, the date is currently August 19 and the time is 20:00. Device 600 displays progress user interface 656 with customized goal 6102 and log entries 614i and 614j. In some embodiments, log entries 614i and 614j were created via selecting activity logging affordance 614b on hourly log user interface 610, similarly described with respect to FIG. 6O. "WALKING" log entry 614j satisfies task 646a "TRY AN ACTIVITY AROUND DINNER," however, it is not performing the activity of customized goal 6102. In contrast, "YOGA" log entry 614i satisfies task 646a and is performing the activity of customized goal 6102. In some embodiments, device 600 displays only the log entries that satisfy the customized goal (e.g., displays "YOGA" log entry 614i without displaying "WALKING" log entry 614j). In some embodiments, device 600 displays all log entries that satisfy task 646a "TRY AN ACTIVITY AROUND DINNER" performed during the week of August 18 to August 24. Device 600 detects tap input 6106 corresponding to selection of progress indicator 6102a.

As shown in FIG. 6AF, in response to receiving tap input 6106, device 600 updates progress indicator 6102a to show a check mark and updates progress indicator 6102b to the selectable plus sign. Below week affordance 656c, device 600 updates from "0%" to "20%," indicating that customized goal 6102 has been completed one of five times.

At the end of the week, on August 24 as shown in FIG. 6AG, device 600 displays goal review user interface 6108. Goal review user interface 6108 includes customize goal 6102 with progress indicators 6102a-6102d filled with a check mark and progress indicator 6102e empty, to show that customized goal 6102 was completed four of five times between August 18 and August 24. Device 600 detects tap input 6110 corresponding to selection of continue affordance 6108a. In response to receiving tap input 6110, device 600 displays rating user interface 6112, as shown in FIG. 6AH.

In FIG. 6AH, device 600 displays rating user interface 6112 that includes rating region 6114. Rating region 6114 includes a rating scale from "0 NOT GOOD" to "10 GREAT" and sliding affordance 6114a positioned at "5" to start. In some embodiments, sliding affordance 6114a is initially positioned at "0 NOT GOOD." Device 600 detects swipe input 6116 corresponding to selection and moving of sliding affordance 6114a.

As shown in FIG. 6AI, in response to receiving swipe input 6116, device 600 moves sliding affordance 6114a to the left and updates "YOUR ANSWER" to "7." Device 600 receives tap input 6118 corresponding to selection of continue affordance 6112a and, in response, proceeds to goal customization user interface 696.

In FIG. 6AJ, goal customization user interface 696 includes a prompt to modify customized goal 6102 based on task 646a using either the selectable edit affordance 696g or selectable delete affordance 696h. In some embodiments, selecting edit affordance 696g causes device 600 to display goal customization user interface 696 of FIG. 6AB. In some embodiments, while device 600 is displaying goal customization user interface 696 of FIG. 6AB for editing the customized goal, device 600 receives tap inputs to change (e.g., modify, edit, update) the customized goal to be performed during the subsequent period of time (e.g., next week, August 25 to August 31). In some embodiments, in response to selection of delete affordance 696h, device 600 ceases display of (e.g., deletes, removes) customized goal 6102. Goal customization user interface 696 also includes a prompt to add a new goal using selectable add affordance 696e. In some embodiments, selecting add affordance 696e causes device 600 to display goal selection user interface 692, similar to that shown in FIG. 6Z, having tasks 648a and 648b available for selection. In some embodiments, selection of either task 648a or 648b initiates goal creation similar to the process described with respect to FIGS. 6AA-6AD. In some embodiments, selecting save affordance 696f causes device 600 to display progress user interface 656, similar to the process described with respect to FIGS. 6AC-6AD.

As shown in FIG. 6AI, device 600 received a rating of "7" for customized goal 6102 performed from August 18 to August 24. In some embodiments, if the rating is a high range rating (e.g., seven or higher), device 600 displays goal customization user interface 696, such as in FIG. 6J. In some embodiments, if the rating of the customized goal is a mid-range rating (e.g., from four to six), device 600 displays feedback user interface 6120, as shown in FIG. 6AK. Feedback user interface 6120 of FIG. 6AK includes a questionnaire to evaluate success factors for completing the customized goal. In some embodiments, if the rating of the customized goal is a low range rating (e.g., three or below), device 600 displays barrier user interface 6122, as shown in FIG. 6AL. Barrier user interface 6122 of FIG. 6AL includes a questionnaire directed to determining barriers (e.g., obstacles) for completing the customized goal. In some embodiments, device 600 further displays examples (e.g., of time management, of ways to maintain motivation) for improving the success and rating of the customized goal. In some embodiments, device 600 further displays suggestions (e.g., tips) for improving the success and rating of the customized goal.

FIG. 7 is a flow diagram illustrating a method for logging user activities during a subset of a recurring time period using an electronic device in accordance with some embodiments. Method 700 is performed at a computer system (e.g., 100, 300, 500, 600) that is in communication with a display generation component (e.g., 602) (e.g., a display controller, a touch-sensitive display system; and/or a display (e.g., integrated or connected)) and one or more input devices (e.g., 112, 160, 602) (e.g. gyroscope, accelerometer, microphone, and/or a touch-sensitive surface). Some operations in method 700 are, optionally, combined, the orders of some operations are, optionally, changed, and some operations are, optionally, omitted.

In some embodiments, the electronic device (e.g., 600) is a computer system. The computer system is optionally in communication (e.g., wired communication, wireless communication) with a display generation component (e.g., 602) and with one or more input devices (e.g., 112, 160, 602). The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 700 provides an intuitive way for logging user activities during a subset of a recurring time period. The method reduces the cognitive burden on a user for logging user activities during a subset of a recurring time period, thereby creating a more efficient human-machine interface. For battery-operated computing devices, enabling a user to logging user activities during a subset of a recurring time period faster and more efficiently conserves power and increases the time between battery charges.

The computer system displays (706), via the display generation component (e.g., 602), a task selection user interface (e.g., 642) with a set of one or more selectable task user interface objects (e.g., 644, 646, 648). The set of one or more selectable task user interface objects includes, in accordance with a determination (708) that physiological data (e.g., 634a) (e.g., data pertaining to blood glucose levels (e.g., a quantification of elevated blood glucose levels for a duration of time); baseline blood glucose measurements) for a first subset of a recurring time period (e.g., the time of day that device 600 received data to display line chart 634a) (e.g., a particular quadrant of time each day (e.g., 6 hours of a day, morning, afternoon, evening, overnight); a day (e.g., Monday, Tuesday) within a week)) meets a first set of criteria (e.g., as illustrated by the elevation value scale of 630a, 634b). In some embodiments, the first set of criteria includes a criterion that is met when the physiological data exceeds a threshold value (e.g., a blood glucose level exceeds a threshold blood glucose level)), a first selectable task user interface object (e.g., 646a-646c) that corresponds to a first type of user activity (e.g., 646a ("TRY AN ACTIVITY"), 646b ("EAT CARBS"), 646c ("AVOID SNACKS")) to be performed during the first subset of the recurring time period (e.g., the time period specified in 658 of FIG. 6N) (e.g., physical activity (e.g., exercise); eating or drinking certain foods). In some embodiments, in accordance with a determination that physiological data for the first subset of the recurring time period does not meet the first set of criteria, the one or more selectable task user interface objects does not include the first selectable task user interface object. The set of one or more selectable task user interface objects includes: in accordance with a determination (710) that physiological data (e.g., the line chart displayed within 636) for a second subset of the recurring time period (e.g., the time of day that device 600 received data to display the line chart within 636), different from the first subset of the recurring time period, meets the first set of criteria (e.g., as illustrated by the elevation value scale of 630a, the elevation value within 636), a second selectable task user interface object (e.g., 648a-648c) that corresponds to a second type of user activity (e.g., 648a ("AVOID HIGH CARB FOODS"), 648b ("TRY SMALLER PORTIONS"), 648c ("EAT A HIGH-FIBER SNACK")) (e.g., a type of activity different than the first type of user activity) to be performed during the second subset of the recurring time period (e.g., the time period specified in 660 of FIG. 6N). In some embodiments, in accordance with a determination that physiological data for a second subset of the recurring time period meets the first set of criteria, the one or more selectable task user interface objects does not include the first selectable task user interface object.

The computer system, while displaying the task selection user interface (e.g., 642), receives (712), via the one or more input devices (e.g., 112, 160), a first set of one or more inputs (e.g., 652a, 652b, 654) (e.g., tap inputs).

The computer system, in response to the receiving (714) the first set of one or more inputs and in accordance with a determination that the first set of one or more inputs includes an input (e.g., 652a) selecting the first selectable task user interface object (e.g., 646a), enables (716) logging of (e.g., recording; tracking; logging via user inputs) the first type of user activity (e.g., 646a) during the first subset of the recurring time period (e.g., the time periods specified in 646 and 660 of FIG. 6N) (e.g., during future occurrences of the first subset of the recurring time period). The computer system, in response to the receiving (714) the first set of one or more inputs and in accordance with a determination that the first set of one or more inputs includes an input (e.g., 652b) selecting the second selectable task user interface object (e.g., 648a), enables (718) logging of the second type of user activity (e.g., 648a) during the second subset of the recurring time period (e.g., as specified in 660). In some embodiments, without enabling logging of the first type of user activity during the first subset of the recurring time period. Displaying first or second selectable task user interface objects that correspond to first or second user activities based on whether physiological data for different subsets of a recurring time period meet a set of criteria provides the user with feedback about the physiological data for the different subsets of the recurring time period. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, prior to displaying the task selection user interface (e.g., 642), receives (702) (e.g., via one or more physiological sensors in communication with the computer system (e.g., integrated into the computer system; in communication with the computer system); a data transfer from another computer system)) a first set of physiological data (e.g., as represented by 612c) for a first predetermined period of time (e.g., from August 1 to August 10 as described with reference to FIGS. 6A-6G) (e.g., 10 days, 14 days, 30 days), wherein the physiological data for the first subset of the recurring time period (e.g., the recurring time period is the period from 12 PM to 6 PM of every day of the predetermined time period) is based on (e.g., derived from, extrapolated from, extracted from) a subset (e.g., 632a, 634a) of the first set of physiological data for the predetermined time period (e.g., as represented by 612c from August 1 to August 10). In some embodiments, the physiological data is blood glucose data for the period from 12 PM to 6 PM for a 10-day data collection period.

The computer system, after receiving the first set of physiological data for the first predetermined period of time (e.g., in response to completing receiving of the first set of physiological data for a predetermined period of time (e.g., at the end of the predetermined time period)), displays (704) a data summary user interface (e.g., 630) that includes a first representation (e.g., 632a, 632a) (e.g., a graphical user interface object; a representation in a graph; a numerical value) of physiological data of the first set of physiological data for the first predetermined period of time that exceeded a first threshold value (e.g., a value below 632a and 634b). In some embodiments, the first representation of physiological data includes an indication of the subset of a recurring time period (e.g., the 6-hour quadrant of the day) during which the physiological data was obtained). In some embodiments, the data summary user interface includes a second representation of physiological data of the first set of physiological data for the predetermined period of time that exceeded the threshold value. In some embodiments, the second representation of physiological data corresponds to data from a different subset of the recurring time period (e.g., from a different quadrant of the day) than the data that corresponds to the first representation of physiological data). Displaying a first representation of physiological data that exceeded a threshold value provides the user with additional feedback as a subset of the received data. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, wherein prior to receiving (e.g., prior to receiving all of) the first set of physiological data for the first predetermined period of time, the task selection user interface (e.g., 642) is not available for display (e.g., is locked; is not available for display at the request of a user), in response to receiving (e.g., receiving all of) the first set of physiological data for the first predetermined period of time, provides the task selection user interface (e.g., 642) for display (e.g., by displaying notification 626) (e.g., making the task selection user interface available for display (e.g., from a previously unavailable state)). In some embodiments, in response to receiving the first set of physiological data for the predetermined period of time, displaying at least a first interface of a set of user interfaces that includes the task selection user interface. Providing the task selection user interface for display in response to the receipt of data controls access to an interface that operates based on whether that data is available yet. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first type of user activity to be performed during the first subset of the recurring time period is performance of a physical activity (e.g., 614g, 614h) (e.g., exercise) or consumption of a food or beverage (e.g., the log entries listed below 648a in FIG. 6T) (e.g., eating a meal).

The computer system, after enabling logging of the first type of user activity during the first subset of the recurring time period and after enabling logging of the second type of user activity during the second subset of the recurring time period, displays a progress user interface (e.g., 656) (e.g., an interface that includes representations of completed user activity(s) that have been enabled for logging) that includes, in accordance with a determination that a first instance (e.g., "WALKING" of 614g, "BIKING" of 614h) of the first type of user activity (e.g., 646a) (e.g., physical activity (e.g., exercise); consumption of food or beverage (e.g., eating carbs last)) has been logged during the first subset of the recurring time period (e.g., the time period specified in 658 of FIG. 6S) (e.g., the recurring time period is the period from 12 PM to 6 PM of every day), displaying a representation (e.g., 614g, 614h) (e.g., a user interface object (e.g., a selectable interface object (e.g., an affordance)) that corresponds to the first instance of the first type of user activity within a first portion (e.g., 658) (e.g., a first third) of the progress user interface (e.g., a user interface containing all completed action items), wherein the first portion of the progress user interface corresponds to the first subset of the recurring time period (e.g., the portion dedicated to logged events from 12 PM to 6 PM of every day).

The computer system, after enabling logging of the first type of user activity during the first subset of the recurring time period and after enabling logging of the second type of user activity during the second subset of the recurring time period, displays a progress user interface (e.g., 656) (e.g., an interface that includes representations of completed user activity(s) that have been enabled for logging) that includes, in accordance with a determination that a first instance (e.g., "SUGAR FREE CHEESECAKE" of FIG. 6T) of the second type of user activity (e.g., 648a) (e.g., physical activity (e.g., exercise); consumption of food or beverage (e.g., eating carbs last)) has been logged during the second subset of the recurring time period (e.g., the time period specified in 660 of FIG. 6T) (e.g., the recurring time period is the period from 12 PM to 6 PM of every day), displaying a representation (e.g., the log entry below 648a in FIG. 6T) (e.g., a user interface object (e.g., a selectable interface object (e.g., an affordance)) that corresponds to the first instance of the second type of user activity within a second portion (e.g., 660) (e.g., a first third) of the progress user interface (e.g., a user interface containing all completed action items), wherein the second portion of the progress user interface corresponds to the second subset of the recurring time period (e.g., the portion dedicated to logged events from 12 PM to 6 PM of every day). In some embodiments, the representation of the completed user activity includes an elevation score. In some embodiments, each portion of the progress user interface includes the baseline measurement elevation score. In some embodiments, a representation of a second instance of first type of user activity is displaying within the first portion of the progress user interface. Displaying a user interface with representations of completed instances of the user activities organized by subsets of the recurring time period provides the user with improved feedback as to what logged activities have been received by the computer system during the specific subsets of the recurring time period. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity during the first subset of the recurring time period, displays a first representation (e.g., 614h) (e.g., a user interface object (e.g., a selectable interface object (e.g., an affordance)) of a logged instance (e.g., "BIKING" at 18:30) of the first type of user activity (e.g., 646a).

The computer system receives a first input (e.g., 676) (e.g., a tap) that corresponds to the representation of the logged instance of the first type of user activity.

The computer system, in response to receiving the first user input, displays a comparison user interface (e.g., 678) that includes the first representation (e.g., a graphical user interface object; a representation in a graph; a numerical value) of physiological data of the first set of physiological data for the first predetermined period of time that exceeded the first threshold value (e.g., 634a).

The computer system, in response to receiving the first user input, displays a comparison user interface (e.g., 678) that includes a second representation (e.g., a graphical user interface object; a representation in a graph) of physiological data of a second set of physiological data (e.g., data collected during the action phase; data different than the first set of physiological data) that corresponds to (e.g., that was collected in a period of time during which the logged instance of the first type of activity was performed) the logged instance of the first type of user activity (e.g., 678b).

The computer system, in response to receiving the first user input, displays a comparison user interface (e.g., 678) that includes a second representation (e.g., that is graphical similar or identical to the first representation) of the logged instance of the first type of user activity (e.g., the activity glyph along 678b of FIG. 6U). Displaying a user interface with first and second representations of physiological data for the same subset of a recurring time period provides the user with feedback as to the state of the data for the same subset of time received by the computer system. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after the first type of user activity has been logged a number of times that exceeds a second threshold value (e.g., the three logged entries listed below 648a in FIG. 6V) (e.g., performing the activity three or more times), displays a first selectable user interface object (e.g., 660a) (e.g., a plus button for adding a new user activity).

The computer system receives, via the one or more input devices (e.g., 112, 160), a second set of one or more inputs (e.g., 682, 686a, 686b) (e.g., tap inputs), wherein the second set of one or more inputs includes an input (e.g., 682) corresponding to the first selectable user interface object (e.g., a tap on the plus button). In some embodiments, the second set of one or inputs includes one or more inputs identifying a type of user activity to be performed during the first subset of the recurring time period.

The computer system, in response to receiving the second set of one or more inputs, enables logging of a third type of user activity (e.g., 648c) during the first subset of the recurring time period (e.g., the time period specified in 660 of FIG. 6X). In some embodiments, an action phase is initiated with two action items to be performed in different subsets of the recurring time period, then add a third action item to one of the subsets, so that two or more action items can be performed for one subset of the recurring time period. In some embodiments, add a third action item for a third subset of the recurring time period (e.g., the recurring time period is the period from 6 PM to 12 AM of every day). In some embodiments, user activities (e.g., action items) are the same for all users (e.g., not personalized). Displaying a selectable user interface object after a condition is met provides the user with feedback that additional operations can be performed. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity during the first subset of the recurring time period, receives a third set of one or more inputs (e.g., 664, 666a, 666b, 670a, 670b), wherein the third set of one or more inputs includes an input (e.g., 664) to initiate a log entry (e.g., in response to 664 at 614b in FIG. 6O) (e.g., an entry corresponding to performance of a user activity (e.g., a physical activity (e.g., exercise); consumption of a food or drink); an entry corresponding to a current mood or sentiment of a user). In some embodiments, the third set of one or more inputs includes one or more inputs selecting or identifying additional details (e.g., the type of activity performed, a time at which it was performed; a current mood) of the log entry.

The computer system, after receiving the input to initiate the log entry, displays a selectable confirmation user interface object (e.g., 646a, 648a as shown on 668 of FIG. 6Q) for the first type of user activity.

The computer system, after receiving the input to initiate the log entry and in response to receiving the third set of one or more inputs, in accordance with a determination that the third set of one or more inputs includes selection (e.g., 670a) of the selectable confirmation user interface object for the first type of user activity, logs an instance of the first type of user activity (e.g., 614g).

The computer system, after receiving the input to initiate the log entry and in response to receiving the third set of one or more inputs, in accordance with a determination that the third set of one or more inputs does not include selection selectable confirmation user interface object for the first type of user activity, logs an event that is not an instance of the first type of user activity (e.g., similar to the "BAGEL" log entry of FIG. 6R). In some embodiments, logging an instance of the first type of user activity includes displaying a selectable user interface object having an indication that the first type of user activity was completed. In some embodiments, logging an event includes displaying a selectable user interface object that does not include an indication that the first type of user activity was completed. In some embodiments, the selectable user interface objects corresponding to instances and events are editable. In some embodiments, the selectable user interface objects corresponding to events are only displayed in the Hours tab and not displayed on the Progress tab. In some embodiments, the selectable user interface objects corresponding to instances of the first type of user activity are displayed on both the Hours tab and the Progress tab. In some embodiments, initiating a log entry includes documenting the time of day. In some embodiments, if the first type of user activity is performed during a time that is not the designated subset of a recurring time period, log an instance of the first type of user activity that includes an indication that the impact of performing the first type of user activity is inconclusive (e.g., action impacts glucose measurements for the specified subset of recurring time).

In some embodiments, enabling logging of the first type of user activity during the first subset of the recurring time period includes enabling logging of the first type of user activity during the first subset of the recurring time period for a second predetermined period of time (e.g., as represented by "DAYS REMAINING" in 656a, from August 11 to August 18 as described with reference to FIGS. 6H-6X) (e.g., 7 days, 14 days). In some embodiments, after the second predetermined period of time, at least one function for logging the first type of activity becomes disabled.

The computer system, after the second predetermined time period ends, provides a goal creation user interface (e.g., 692) for display (e.g., making a goal creation user interface available for display (e.g., from a previously unavailable state)), wherein the goal creation user interface is unavailable for display prior to completion of the second predetermined period of time. In some embodiments, the goal creation user interface is an interface that corresponds to method 800. Providing a goal creation user interface for display after a predetermined time period ends permits access to the interface at a point in time when the function of the interface is relevant. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

Note that details of the processes described above with respect to method 700 (e.g., FIG. 7) are also applicable in an analogous manner to the methods described below. For example, method 800 optionally includes one or more of the characteristics of the various methods described above with reference to method 700. For example, the goal creation user interface of method 800 displays a set of one or more selectable goal creation user interface objects, wherein the set of one or more selectable goal creation user interface objects are based on the logging of the type of user activity during the first subset of the recurring time period as in method 700. For brevity, these details are not repeated below.

FIGS. 8A-8B are a flow diagram illustrating a method for logging user activities during a subset of a recurring time period using an electronic device in accordance with some embodiments. Method 800 is performed at a computer system (e.g., 100, 300, 500, 600) (e.g., a smart phone, a smart watch) that is in communication with a display generation component (e.g., 602) (e.g., a display controller, a touch-sensitive display system; and/or a display (e.g., integrated or connected)) and one or more input devices (e.g., 160) (e.g. gyroscope, accelerometer, microphone, and/or a touch-sensitive surface). Some operations in method 800 are, optionally, combined, the orders of some operations are, optionally, changed, and some operations are, optionally, omitted.

As described below, method 800 provides an intuitive way for logging user activities during a subset of a recurring time period. The method reduces the cognitive burden on a user for logging user activities during a subset of a recurring time period, thereby creating a more efficient human-machine interface. For battery-operated computing devices, enabling a user to logging user activities during a subset of a recurring time period faster and more efficiently conserves power and increases the time between battery charges.

The computer system displays (802), via the display generation component (e.g., 602), a goal creation user interface (e.g., 692, 696) with a set of one or more selectable goal creation user interface objects (e.g., 646a, 648a, 648c).

The set of one or more selectable user interface objects includes, in accordance with a determination (804) that a first type of user activity (e.g., the activity described with respect to 646*a*) (e.g., physical activity (e.g., exercise); eating or drinking certain foods) performed for a first subset of a recurring time period (e.g., the time period specified in 658 of FIG. 6S) (e.g., a particular quadrant of time each day (e.g., 6 hours of a day, morning, afternoon, evening, overnight); a day (e.g., Monday, Tuesday) within a week)) meets a first set of criteria (e.g., the criteria discussed at FIG. 6Z), a first selectable goal creation user interface object (e.g., 646*a*) that corresponds to the first type of user activity to be performed during the first subset of the recurring time period. In some embodiments, the first set of criteria includes a criterion that is met when the first type of user activity was performed more than a threshold number of times. In some embodiments, the first set of criteria includes a criterion that is met when the first type of user activity is determined to have had a positive effect on physiological data. In some embodiments, in accordance with a determination that the first type of user activity performed for the first subset of the recurring time period did not meet the first set of criteria, the one or more selectable goal creation user interface objects does not include the first selectable goal creation user interface object. In some embodiments, the first type of user activity performed for the first subset of the recurring time period was logged according to the method of 700. In some embodiments, the first set of criteria includes a criterion that is met when the first type of user activity has been available for a predetermined time period (e.g., a week, the duration of the action phase). In some embodiments, the goal creation user interface becomes available after the predetermined time period ends. The set of one or more selectable user interface objects includes, in accordance with a determination (806) that a second type of user activity (e.g., the activity described with respect to 648*a*) performed for a second subset of a recurring time period (e.g., the time period specified in 660 of FIG. 6T), different from the first subset of the recurring time period, meets a first set of criteria (e.g., the criteria discussed at FIG. 6Z), a second selectable goal creation user interface object (e.g., 648*a*) that corresponds to the second type of user activity (e.g., a type of activity different than the first type of user activity) to be performed during the second subset of the recurring time period.

The computer system, while displaying the goal creation user interface (e.g., 692), receives (818) a first set of one or more inputs (e.g., 694*a*, 694*b*, 698*a*, 698*b*, 698*c*) (e.g., taps).

The computer system, in response to the receiving (820) the first set of one or more inputs and in accordance with a determination that the first set of one or more inputs includes an input (e.g., 646*a*) selecting the first selectable goal creation user interface object (e.g., 646*a*), enables (822) logging (e.g., recording; tracking; logging via user inputs) of the first type of user activity during the first subset of the recurring time period (e.g., during future occurrences of the first subset of the recurring time period) for a predetermined duration of time (e.g., 656*c*) (e.g., a week, 10 days).

The computer system, in response to the receiving (820) the first set of one or more inputs and in accordance with a determination that the first set of one or more inputs includes an input selecting the second selectable goal creation user interface object (e.g., a tap at 648*a* in FIG. 6Z), enables (824) logging of the second type of user activity during the second subset of the recurring time period for the predetermined duration of time (e.g., 656*c*). In some embodiments, without enabling logging of the first type of user activity during the first subset of the recurring time period. Displaying first or second selectable goal creation user interface objects based on whether a first or second type of activity was performed provides the user with feedback as to what types of activities were previously performed. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the goal creation user interface (e.g., 696) includes (808) (e.g., concurrently, non-concurrently) a set (810) of one or more selectable user interface objects (e.g., 696*a*) (e.g., a text field; selectable predefined options) that, when selected, configure (e.g., identify; detail; set) a subtype (e.g., "YOGA" as discussed at FIG. 6AB) of the first type of user activity (e.g., 646*a*). In some embodiments, the goal creation user interface (e.g., 696) includes (808) (e.g., concurrently, non-concurrently) a set (812) of one or more selectable user interface objects (e.g., 698*b*) (e.g., a text field; selectable predefined options) that, when selected, configure (e.g., identify; detail; set) a time period (e.g., "AROUND DINNER" of 646*a*) (e.g., before a meal; after a meal; at the beginning or the end of the first subset of the recurring time period) within the first subset of the recurring time period (e.g., the time period specified in 658 of FIG. 6S) during which the first type of user activity is to be performed. In some embodiments, the goal creation user interface (e.g., 696) includes (808) (e.g., concurrently, non-concurrently) a set (814) of one or more selectable user interface objects (e.g., 696*b*) (e.g., a text field; selectable predefined options) that, when selected, configure (e.g., identify; detail; set) a duration (e.g., 20 minutes as discussed at FIG. 6AB) (e.g., 30 minutes; 60 minutes) for which the first type of user activity is to be performed. Displaying selectable user interface objects that configure the goal provides the user with additional control options for customizing the first type of user activity. Providing additional control options enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the goal creation user interface includes (808) a set (816) of one or more selectable user interface objects (e.g., 696*c*) (e.g., a text field; selectable predefined options) that, when selected, configure (e.g., identify; detail; set) a target number of times (e.g., "5 TIMES" as discussed at FIG. 6AB) (e.g., a goal) that the first type of user activity is to be performed (e.g., logged as performed) during the first subset of the recurring time period for the predetermined duration of time. Displaying selectable user interface objects that configure the goal provides the user with more control of the device. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first set of criteria is satisfied when a user activity of a given type has been performed (e.g., performed and logged) at least once during a preceding predetermined period of time (e.g., 614g, 614h, the log entries listed within 660) (e.g., an action phase). In some embodiments, the first set of criteria are met when physiological data indicates that a user activity of a given type had a target (e.g., positive) effect on a physiological parameter (e.g., blood glucose levels). In some embodiments, the goal creation user interface (e.g., 692) includes, for each given type of activity that met the first set of criteria, a selectable goal creation user interface object (e.g., 646a, 648a, 648c as discussed at FIG. 6Z) for the given type of activity that met the first set of criteria. In some embodiments, the goal creation user interface provides goal creation user interface objects for all activity types that were performed during an action phase. Displaying a selectable goal creation user interface object for the given types of activity that met the first set of criteria provides the user with additional feedback as specific activities that were performed. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity (e.g., 6102) during the first subset of the recurring time for the predetermined duration of time, displays a representation (e.g., 6102a-6102e) (e.g., an indication; a graphical user interface object) of the target number of times (e.g., "5 TIMES" as discussed at FIG. 6AB) (e.g., a minimum number of times) that the first type of user activity (e.g., 6102) is to be performed during the first subset of the recurring time period for the predetermined duration of time. In some embodiments, the representation includes an indication of the number of times that first type of user activity has already been completed during the predetermined time period. In some embodiments, the representation is seven empty circles, each representing a day, that are filled is as the first type of user activity is completed. Displaying an indication (e.g., a progress indicator) of progress towards a target number of times that the first type of user activity is to be performed during the first subset of the recurring time period for the predetermined duration of time provides the user with feedback as to what is required to meet the target. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity (e.g., 6102) during the first subset of the recurring time for the predetermined duration of time and after the end of the predetermined duration of time (e.g., on August 24 at FIG. 6AG), receives a second set of one or more user inputs (e.g., 6110, 6116, 6118) that correspond to feedback (e.g., 6114a along the rating scale at FIGS. 6AH-6AI) regarding the first type of user activity (e.g., feedback indicating a user's sentiment and/or assessment of performance of the first type of user activity during the predetermined duration of time).

The computer system, after receiving the first set of one or more user inputs (e.g., after selection of 696g) and, in some embodiments, in accordance with a determination that the feedback regarding the first type of user activity satisfies a first set of feedback criteria (e.g., the feedback is of a first type (e.g., negative feedback), displays a set of one or more selectable user interface objects (e.g., analogous to 696a, 696b, and 696c at FIG. 6AB) (e.g., a text field; selectable predefined options) that, when selected, modify one or more characteristics (e.g.; a target number of times the activity is to be performed; a duration for which the activity is to be performed) of the first type of user activity (e.g., modify for logging during a second, upcoming predetermined period of time). Displaying a set of one or more selectable user interface objects to modify one or more characteristics of the first type of user activity provides the user with more control of the device. Providing additional control of the device enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity during the first subset of the recurring time for the predetermined duration of time and after the end of the predetermined duration of time (e.g., on August 24 at FIG. 6AG), receives the second set of one or more user inputs (e.g., 6110, 6116, 6118) that correspond to feedback regarding the first type of user activity (e.g., feedback indicating a user's sentiment and/or assessment of performance of the first type of user activity during the predetermined duration of time).

The computer system, after receiving the second set of one or more user inputs (e.g., after selection of 696e) and, in some embodiments, in accordance with a determination that the feedback regarding the first type of user activity satisfies a first set of feedback criteria (e.g., the feedback is of a first type (e.g., negative feedback), displays a set of one or more selectable user interface objects (e.g., analogous to 648a and 648b at FIG. 6Z) (e.g., a text field; selectable predefined options) that, when selected, enables logging of a third type of user activity, different from the first type of user activity, during the first subset of the recurring time period for a second predetermined duration of time (e.g., a subsequent period of 7 days), after the first predetermined period of time. In some embodiments, display different questions based on selection of ranking affordance (e.g., what went well? What could go better?). In some embodiments, for selection of a low ranking affordance (e.g., 4 or lower), provide tips for overcoming barriers. In some embodiments, display 6 tips per action item category. In some embodiments, for selection of a high ranking affordance (e.g., 7 or higher), do not display tips and proceed to option to modify goal. Displaying a set of one or more selectable user interface objects to enable logging of a third type of user activity provides the user with more control of the device. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system, after enabling logging of the first type of user activity during the first subset of the recurring time for the predetermined duration of time, displays a progress user interface (e.g., 656) (e.g., an interface that includes representations of completed user activity(s) that have been enabled for logging), wherein the progress user interface includes: a first selectable user interface object (e.g., 656*b*) that corresponds to the preceding predetermined period of time (e.g., the action phase), that when selected, displays representations of logged instances of the first type of user activity for the preceding predetermined period of time (e.g., 614*g*, 614*h*, the log entries listed within 660 at FIGS. 6S-6V) (e.g., the first type of user activity performed during the first subset of the recurring time period); and a second selectable user interface object (e.g., 656*c*) that corresponds to the predetermined duration of time, that when selected, displays representations of logged instances (e.g. 614*i*, 614*j*) of the first type of user activity for the predetermined period of time (e.g., the first type of user activity performed during the first subset of the recurring time period). Displaying a user interface with selectable user interface objects to view logged activities for a predetermined period of time provides the user with improved feedback as to what logged activities have been received by the computer system. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of logged user activities during a subset of a recurring time period or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content based on the logged user activities during a subset of a recurring time period that is of greater interest to the user. Accordingly, use of such personal information data enables users to have calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of logging user activities during a subset of a recurring time period, the present technology can be configured to allow users to select to "opt in" or "opt out" of participation in the collection of personal information data during registration for services or anytime thereafter. In another example, users can select not to provide data for logging user activities during a subset of a recurring time period. In yet another example, users can select to limit the length of time data is maintained or entirely prohibit the development of a baseline profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

What is claimed is:

1. A computer system, comprising:
   a display generation component;
   one or more input devices;
   one or more processors; and
   memory storing one or more programs configured to be executed by the one or more processors, the one or more programs including instructions for:
   displaying, via the display generation component, a task selection user interface with a set of one or more selectable task user interface objects, the set of one or more selectable task user interface objects includes:
   in accordance with a determination that physiological data for a first subset of a recurring time period meets a first set of criteria, a first selectable task user interface object that corresponds to a first type of user activity to be performed during the first subset of the recurring time period; and
   in accordance with a determination that physiological data for a second subset of the recurring time period, different from the first subset of the recurring time period, meets the first set of criteria, a second selectable task user interface object that corresponds to a second type of user activity to be performed during the second subset of the recurring time period;
   while displaying the task selection user interface, receiving, via the one or more input devices, a first set of one or more inputs; and
   in response to receiving the first set of one or more inputs:
   in accordance with a determination that the first set of one or more inputs includes an input selecting the first selectable task user interface object, enabling logging of the first type of user activity during the first subset of the recurring time period; and
   in accordance with a determination that the first set of one or more inputs includes an input selecting the second selectable task user interface object, enabling logging of the second type of user activity during the second subset of the recurring time period.

2. The computer system of claim 1, the one or more programs further including instructions for:
   prior to displaying the task selection user interface, receiving a first set of physiological data for a first predetermined period of time,
   wherein the physiological data for the first subset of the recurring time period is based on a subset of the first set of physiological data for the first predetermined period of time.

3. The computer system of claim 2, the one or more programs further including instructions for:
   after receiving the first set of physiological data for the first predetermined period of time, displaying a data summary user interface that includes:
   a first representation of physiological data of the first set of physiological data for the first predetermined period of time that exceeded a first threshold value.

4. The computer system of claim 3, the one or more programs further including instructions for:
   after enabling logging of the first type of user activity during the first subset of the recurring time period, displaying a first representation of a logged instance of the first type of user activity;
   receiving a first input that corresponds to the representation of the logged instance of the first type of user activity;
   in response to receiving the first input, displaying a comparison user interface that includes:
   the first representation of physiological data of the first set of physiological data for the first predetermined period of time that exceeded the first threshold value; and
   a second representation of physiological data of a second set of physiological data that corresponds to the logged instance of the first type of user activity; and
   and a second representation of the logged instance of the first type of user activity.

5. The computer system of claim 2, wherein prior to receiving the first set of physiological data for the first predetermined period of time, the task selection user interface is not available for display,
   the one or more programs further including instructions for:
   in response to receiving the first set of physiological data for the first predetermined period of time, providing the task selection user interface for display.

6. The computer system of claim 1, wherein the first type of user activity to be performed during the first subset of the recurring time period is performance of a physical activity or consumption of a food or beverage.

7. The computer system of claim 1, the one or more programs further including instructions for:
   after enabling logging of the first type of user activity during the first subset of the recurring time period and after enabling logging of the second type of user activity during the second subset of the recurring time period, displaying a progress user interface, wherein the progress user interface includes:
   in accordance with a determination that a first instance of the first type of user activity has been logged during the first subset of the recurring time period, displaying a representation that corresponds to the first instance of the first type of user activity within a first portion of the progress user interface, wherein the first portion of the progress user interface corresponds to the first subset of the recurring time period; and in accordance with a determination that a first instance of the second type of user activity has been logged during the second subset of the recurring time period, displaying a representation that corresponds to the first instance of the second type of user activity within a second portion of the progress user interface, wherein the second portion of the progress user interface corresponds to the second subset of the recurring time period.

8. The computer system of claim 1, the one or more programs further including instructions for:

after the first type of user activity has been logged a number of times that exceeds a second threshold value, displaying a first selectable user interface object;

receiving, via the one or more input devices, a second set of one or more inputs, wherein the second set of one or more inputs includes an input corresponding to the first selectable user interface object; and in response to receiving the second set of one or more inputs:

enabling logging of a third type of user activity during the first subset of the recurring time period.

9. The computer system of claim 1, the one or more programs further including instructions for:

after enabling logging of the first type of user activity during the first subset of the recurring time period, receiving a third set of one or more inputs, wherein the third set of one or more inputs includes an input to initiate a log entry;

after receiving the input to initiate the log entry:

displaying a selectable confirmation user interface object for the first type of user activity; and in response to receiving the third set of one or more inputs:

in accordance with a determination that the third set of one or more inputs includes selection of the selectable confirmation user interface object for the first type of user activity, logging an instance of the first type of user activity; and in accordance with a determination that the third set of one or more inputs does not include selection selectable confirmation user interface object for the first type of user activity, logging an event that is not an instance of the first type of user activity.

10. The computer system of claim 1, wherein enabling logging of the first type of user activity during the first subset of the recurring time period includes enabling logging of the first type of user activity during the first subset of the recurring time period for a second predetermined period of time.

11. The computer system of claim 10, the one or more programs further including instructions for:

after the second predetermined period of time ends, providing a goal creation user interface for display, wherein the goal creation user interface is unavailable for display prior to completion of the second predetermined period of time.

12. A non-transitory computer-readable storage medium storing one or more programs configured to be executed by one or more processors of a computer system that is in communication with a display generation component and one or more input devices, the one or more programs including instructions for:

displaying, via the display generation component, a task selection user interface with a set of one or more selectable task user interface objects, the set of one or more selectable task user interface objects includes:

in accordance with a determination that physiological data for a first subset of a recurring time period meets a first set of criteria, a first selectable task user interface object that corresponds to a first type of user activity to be performed during the first subset of the recurring time period; and in accordance with a determination that physiological data for a second subset of the recurring time period, different from the first subset of the recurring time period, meets the first set of criteria, a second selectable task user interface object that corresponds to a second type of user activity to be performed during the second subset of the recurring time period;

while displaying the task selection user interface, receiving, via the one or more input devices, a first set of one or more inputs; and in response to the receiving the first set of one or more inputs:

in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

13. The non-transitory computer-readable storage medium of claim 12, the one or more programs further including instructions for:

prior to displaying the task selection user interface, receiving a first set of physiological data for a first predetermined period of time, wherein the physiological data for the first subset of the recurring time period is based on a subset of the first set of physiological data for the first predetermined period of time.

14. The non-transitory computer-readable storage medium of claim 13, the one or more programs further including instructions for:

after receiving the first set of physiological data for the first predetermined period of time, displaying a data summary user interface that includes:

a first representation of physiological data of the first set of physiological data for the first predetermined period of time that exceeded a first threshold value.

15. The non-transitory computer-readable storage medium of claim 14, the one or more programs further including instructions for:

after enabling logging of the first type of user activity during the first subset of the recurring time period, displaying a first representation of a logged instance of the first type of user activity;

receiving a first input that corresponds to the representation of the logged instance of the first type of user activity;

in response to receiving the first input, displaying a comparison user interface that includes:

the first representation of physiological data of the first set of physiological data for the first predetermined period of time that exceeded the first threshold value; and a second representation of physiological data of a second set of physiological data that corresponds to the logged instance of the first type of user activity; and and a second representation of the logged instance of the first type of user activity.

16. The non-transitory computer-readable storage medium of claim 13, wherein prior to receiving the first set of physiological data for the first predetermined period of time, the task selection user interface is not available for display, the one or more programs further including instructions for:
in response to receiving the first set of physiological data for the first predetermined period of time, providing the task selection user interface for display.

17. The non-transitory computer-readable storage medium of claim 12, wherein the first type of user activity to be performed during the first subset of the recurring time period is performance of a physical activity or consumption of a food or beverage.

18. The non-transitory computer-readable storage medium of claim 12, the one or more programs further including instructions for:
after enabling logging of the first type of user activity during the first subset of the recurring time period and after enabling logging of the second type of user activity during the second subset of the recurring time period, displaying a progress user interface, wherein the progress user interface includes:
in accordance with a determination that a first instance of the first type of user activity has been logged during the first subset of the recurring time period, displaying a representation that corresponds to the first instance of the first type of user activity within a first portion of the progress user interface, wherein the first portion of the progress user interface corresponds to the first subset of the recurring time period; and
in accordance with a determination that a first instance of the second type of user activity has been logged during the second subset of the recurring time period, displaying a representation that corresponds to the first instance of the second type of user activity within a second portion of the progress user interface, wherein the second portion of the progress user interface corresponds to the second subset of the recurring time period.

19. The non-transitory computer-readable storage medium of claim 12, the one or more programs further including instructions for:
after the first type of user activity has been logged a number of times that exceeds a second threshold value, displaying a first selectable user interface object;
receiving, via the one or more input devices, a second set of one or more inputs, wherein the second set of one or more inputs includes an input corresponding to the first selectable user interface object; and
in response to receiving the second set of one or more inputs:
enabling logging of a third type of user activity during the first subset of the recurring time period.

20. The non-transitory computer-readable storage medium of claim 12, the one or more programs further including instructions for:
after enabling logging of the first type of user activity during the first subset of the recurring time period, receiving a third set of one or more inputs, wherein the third set of one or more inputs includes an input to initiate a log entry;
after receiving the input to initiate the log entry:
displaying a selectable confirmation user interface object for the first type of user activity; and
in response to receiving the third set of one or more inputs:
in accordance with a determination that the third set of one or more inputs includes selection of the selectable confirmation user interface object for the first type of user activity, logging an instance of the first type of user activity; and
in accordance with a determination that the third set of one or more inputs does not include selection selectable confirmation user interface object for the first type of user activity, logging an event that is not an instance of the first type of user activity.

21. The non-transitory computer-readable storage medium of claim 12, wherein enabling logging of the first type of user activity during the first subset of the recurring time period includes enabling logging of the first type of user activity during the first subset of the recurring time period for a second predetermined period of time.

22. The non-transitory computer-readable storage medium of claim 21, the one or more programs further including instructions for:
after the second predetermined period of time ends, providing a goal creation user interface for display, wherein the goal creation user interface is unavailable for display prior to completion of the second predetermined period of time.

23. A method, comprising:
at a computer system that is in communication with a display generation component and one or more input devices:
displaying, via the display generation component, a task selection user interface with a set of one or more selectable task user interface objects, the set of one or more selectable task user interface objects includes:
in accordance with a determination that physiological data for a first subset of a recurring time period meets a first set of criteria, a first selectable task user interface object that corresponds to a first type of user activity to be performed during the first subset of the recurring time period; and
in accordance with a determination that physiological data for a second subset of the recurring time period, different from the first subset of the recurring time period, meets the first set of criteria, a second selectable task user interface object that corresponds to a second type of user activity to be performed during the second subset of the recurring time period;
while displaying the task selection user interface, receiving, via the one or more input devices, a first set of one or more inputs; and
in response to the receiving the first set of one or more inputs:
in accordance with a determination that the first set of one or more inputs includes an input selecting the first selectable task user interface object, enabling logging of the first type of user activity during the first subset of the recurring time period; and in accordance with a determination that the first set of one or more inputs includes an input selecting the second selectable task user interface object, enabling logging of the second type of user activity during the second subset of the recurring time period.

24. The method of claim 23, further comprising:
prior to displaying the task selection user interface, receiving a first set of physiological data for a first predetermined period of time,
wherein the physiological data for the first subset of the recurring time period is based on a subset of the first set of physiological data for the first predetermined period of time.

25. The method of claim 24, further comprising:
after receiving the first set of physiological data for the first predetermined period of time, displaying a data summary user interface that includes:
a first representation of physiological data of the first set of physiological data for the first predetermined period of time that exceeded a first threshold value.

26. The method of claim 25, further comprising:
after enabling logging of the first type of user activity during the first subset of the recurring time period, displaying a first representation of a logged instance of the first type of user activity;
receiving a first input that corresponds to the representation of the logged instance of the first type of user activity;
in response to receiving the first input, displaying a comparison user interface that includes:
the first representation of physiological data of the first set of physiological data for the first predetermined period of time that exceeded the first threshold value; and
a second representation of physiological data of a second set of physiological data that corresponds to the logged instance of the first type of user activity; and
and a second representation of the logged instance of the first type of user activity.

27. The method of claim 24, wherein prior to receiving the first set of physiological data for the first predetermined period of time, the task selection user interface is not available for display, the method further comprising:
in response to receiving the first set of physiological data for the first predetermined period of time, providing the task selection user interface for display.

28. The method of claim 23, wherein the first type of user activity to be performed during the first subset of the recurring time period is performance of a physical activity or consumption of a food or beverage.

29. The method of claim 23, further comprising:
after enabling logging of the first type of user activity during the first subset of the recurring time period and after enabling logging of the second type of user activity during the second subset of the recurring time period, displaying a progress user interface, wherein the progress user interface includes:
in accordance with a determination that a first instance of the first type of user activity has been logged during the first subset of the recurring time period, displaying a representation that corresponds to the first instance of the first type of user activity within a first portion of the progress user interface, wherein the first portion of the progress user interface corresponds to the first subset of the recurring time period; and
in accordance with a determination that a first instance of the second type of user activity has been logged during the second subset of the recurring time period, displaying a representation that corresponds to the first instance of the second type of user activity within a second portion of the progress user interface, wherein the second portion of the progress user interface corresponds to the second subset of the recurring time period.

30. The method of claim 23, further comprising:
after the first type of user activity has been logged a number of times that exceeds a second threshold value, displaying a first selectable user interface object;
receiving, via the one or more input devices, a second set of one or more inputs, wherein the second set of one or more inputs includes an input corresponding to the first selectable user interface object; and
in response to receiving the second set of one or more inputs:
enabling logging of a third type of user activity during the first subset of the recurring time period.

31. The method of claim 23, further comprising:
after enabling logging of the first type of user activity during the first subset of the recurring time period, receiving a third set of one or more inputs, wherein the third set of one or more inputs includes an input to initiate a log entry;
after receiving the input to initiate the log entry:
displaying a selectable confirmation user interface object for the first type of user activity; and
in response to receiving the third set of one or more inputs:
in accordance with a determination that the third set of one or more inputs includes selection of the selectable confirmation user interface object for the first type of user activity, logging an instance of the first type of user activity; and
in accordance with a determination that the third set of one or more inputs does not include selection selectable confirmation user interface object for the first type of user activity, logging an event that is not an instance of the first type of user activity.

32. The method of claim 23, wherein enabling logging of the first type of user activity during the first subset of the recurring time period includes enabling logging of the first type of user activity during the first subset of the recurring time period for a second predetermined period of time.

33. The method of claim 32, further comprising:
after the second predetermined period of time ends, providing a goal creation user interface for display, wherein the goal creation user interface is unavailable for display prior to completion of the second predetermined period of time.

* * * * *

UNITED STATES PATENT AND TRADEMARK OFFICE
CERTIFICATE OF CORRECTION

PATENT NO. : 12,001,648 B2  
APPLICATION NO. : 17/952053  
DATED : June 4, 2024  
INVENTOR(S) : Aneesha Narra et al.

Page 1 of 1

It is certified that error appears in the above-identified patent and that said Letters Patent is hereby corrected as shown below:

In the Claims

In Column 60, Line 40, Claim 7, delete "and a" and insert -- a --, therefor.

In Column 63, Line 5, Claim 19, delete "and a" and insert -- a --, therefor.

In Column 65, Line 40, Claim 26, delete "and a" and insert -- a --, therefor.

Signed and Sealed this  
Eleventh Day of February, 2025

Coke Morgan Stewart  
*Acting Director of the United States Patent and Trademark Office*